US011827435B2

(12) United States Patent
Sanders et al.

(10) Patent No.: US 11,827,435 B2
(45) Date of Patent: Nov. 28, 2023

(54) MODULAR SWIVELING STRAP TIE SYSTEM

(71) Applicant: FOOT INNOVATIONS, LLC, Tampa, FL (US)

(72) Inventors: Roy W. Sanders, Tampa, FL (US); Sergio Gutierrez, Tampa, FL (US)

(73) Assignee: FOOT INNOVATIONS, LLC, Tampa, FL (US)

( * ) Notice: Subject to any disclaimer, the term of this patent is extended or adjusted under 35 U.S.C. 154(b) by 932 days.

(21) Appl. No.: 16/557,727

(22) Filed: Aug. 30, 2019

(65) Prior Publication Data
US 2019/0382175 A1  Dec. 19, 2019

Related U.S. Application Data

(63) Continuation of application No. 15/589,631, filed on May 8, 2017, now Pat. No. 10,399,755, which is a
(Continued)

(51) Int. Cl.
*A61B 17/08* (2006.01)
*B65D 63/18* (2006.01)
(Continued)

(52) U.S. Cl.
CPC ............ *B65D 63/18* (2013.01); *A61B 17/08* (2013.01); *B65D 63/02* (2013.01);
(Continued)

(58) Field of Classification Search
CPC ... A61B 17/0466; A61B 17/08; A61B 17/083; A61B 17/085; A61B 2017/081;
(Continued)

(56) References Cited

U.S. PATENT DOCUMENTS 3,473,528 A   10/1969   Mishkin et al.
3,926,193 A   12/1975   Hasson
(Continued)

FOREIGN PATENT DOCUMENTS

GB  2 223 410 A   4/1990
WO  WO-94/26173   11/1994

OTHER PUBLICATIONS

European Office Action on EP Appl. No. 16733243.6 dated Dec. 9, 2019 (5 pages).
(Continued)

*Primary Examiner* — Diane D Yabut
*Assistant Examiner* — Christian D. Knauss
(74) *Attorney, Agent, or Firm* — Foley & Lardner LLP

(57) ABSTRACT

A strap tie includes a body including a receiving channel and a strap engagement member. The receiving channel extends through the body. The receiving channel is configured to receive a remote strap. The engagement member is configured to engage a movement restriction member of the remote strap to prevent translation of the remote strap away from the body. The strap extends from the body. The strap includes a proximal end attached to the body, a distal end opposite the proximal end, and a plurality of movement restriction members. The rotational element of the body is configured to removably couple to a base to allow the strap tie to rotate relative to the base.

20 Claims, 53 Drawing Sheets

Related U.S. Application Data continuation-in-part of application No. 15/175,867, filed on Jun. 7, 2016, now Pat. No. 9,757,131, and a continuation of application No. PCT/US2017/029415, filed on Apr. 25, 2017, which is a continuation of application No. 15/138,067, filed on Apr. 25, 2016, now abandoned, and a continuation of application No. 15/175,867, filed on Jun. 7, 2016, now Pat. No. 9,757,131, which is a continuation of application No. 15/138,067, filed on Apr. 25, 2016, now abandoned, which is a continuation-in-part of application No. 14/734,846, filed on Jun. 9, 2015, now Pat. No. 9,345,483.

(51) Int. Cl.
*B65D 63/02* (2006.01)
*B65D 63/10* (2006.01)

(52) U.S. Cl.
CPC .... *B65D 63/1063* (2013.01); *A61B 2017/081* (2013.01); *A61B 2017/086* (2013.01); *B65D 2563/00* (2013.01); *B65D 2563/107* (2013.01); *B65D 2563/108* (2013.01)

(58) Field of Classification Search
CPC ........ A61B 2017/086; A61B 2017/088; B65D 63/02; B65D 63/1063; B65D 63/18; B65D 2563/00; B65D 2563/10; B65D 2563/101; B65D 2563/102; B65D 2563/103; B65D 2563/105; B65D 2563/106; B65D 2563/107; B65D 2563/108
See application file for complete search history.

(56) References Cited

U.S. PATENT DOCUMENTS

| | | | |
|---|---|---|---|
| 3,971,384 | A | 7/1976 | Hasson |
| 4,924,866 | A | 5/1990 | Yoon |
| D333,193 | S | 2/1993 | Archambault |
| 5,263,970 | A | 11/1993 | Preller |
| 5,562,705 | A | 10/1996 | Whiteford |
| 5,759,193 | A | 6/1998 | Burbank et al. |
| 5,893,879 | A | 4/1999 | Hirshowitz et al. |
| 6,051,007 | A | 4/2000 | Hogendijk et al. |
| 6,119,314 | A | 9/2000 | Freed |
| 6,176,868 | B1 | 1/2001 | Detour |
| 6,280,133 | B1 | 8/2001 | Haberle |
| 7,361,185 | B2 | 4/2008 | O'Malley et al. |
| 7,591,835 | B2 | 9/2009 | Warren |
| 7,686,829 | B2 | 3/2010 | Elliott et al. |
| 7,972,347 | B2 | 7/2011 | Garvin et al. |
| 7,972,362 | B2 | 7/2011 | Wilke et al. |
| 7,981,136 | B2 | 7/2011 | Weiser |
| D652,145 | S | 1/2012 | Topaz |
| 8,764,792 | B2 | 7/2014 | Weiser |
| 8,864,796 | B2 | 10/2014 | Elliott et al. |
| 8,916,741 | B2 | 12/2014 | Fischell et al. |
| 9,068,674 | B1 | 6/2015 | Mangone, Jr. |
| 10,029,835 | B1* | 7/2018 | Cuddy .................... F16L 3/137 |
| 2002/0104196 | A1* | 8/2002 | Geiger ............... B65D 63/1072 24/16 PB |
| 2004/0204740 | A1 | 10/2004 | Weiser |
| 2004/0267309 | A1 | 12/2004 | Garvin |
| 2006/0095076 | A1 | 5/2006 | Elliott et al. |
| 2007/0038247 | A1 | 2/2007 | Lebner et al. |
| 2009/0036922 | A1 | 2/2009 | Riskin et al. |
| 2014/0236227 | A1 | 8/2014 | Nash et al. |
| 2015/0088195 | A1 | 3/2015 | Moustafa |

OTHER PUBLICATIONS

European Office Action on EP Appl. No. 16733243.6 dated Mar. 26, 2019 (4 pages).
International Preliminary Report on Patentability on PCT Appl. No. PCT/US2016/036234 dated Dec. 21, 2017 (12 pages).
International Preliminary Report on Patentability on PCT Appl. No. PCT/US2017/029415 dated Nov. 8, 2017 (6 pages).
International Search Report and Written Opinion on PCT Appl. No. PCT/US2016/036234 dated Oct. 21, 2016 (19 pages).
International Search Report and Written Opinion on PCT Appl. No. PCT/US2017/029415 dated Jul. 13, 2017 (13 pages).
U.S. Final Office Action on U.S. Appl. No. 15/175,867 dated Sep. 30, 2016 (24 pages).
U.S. Final Office Action on U.S. Appl. No. 15/589,631 dated Jan. 30, 2018 (14 pages).
U.S. Non-Final Office Action on U.S. Appl. No. 15/589,631 dated Jul. 19, 2017 (16 pages).
U.S. Non-Final Office Action on U.S. Appl. No. 14/734,846 dated Aug. 26, 2015 (20 pages).
U.S. Non-Final Office Action on U.S. Appl. No. 15/138,067 dated Sep. 30, 2016 (24 pages).
U.S. Non-Final Office Action on U.S. Appl. No. 15/589,631 dated Sep. 5, 2018 (16 pages).
U.S. Notice of Allowance on U.S. Appl. No. 14/734,846 dated Jan. 22, 2016 (12 pages).
U.S. Notice of Allowance on U.S. Appl. No. 15/175,867 dated May 10, 2017 (9 pages).
U.S. Notice of Allowance on U.S. Appl. No. 15/589,631 dated Apr. 24, 2019 (8 pages).

* cited by examiner

MODULAR SWIVELING STRAP TIE SYSTEM

CROSS-REFERENCE TO RELATED APPLICATIONS

This application is a continuation of U.S. patent application Ser. No. 15/589,631, filed May 8, 2017, entitled "Modular Swiveling Strap Tie System," which is a continuation of International Patent Application No. PCT/US2017/029415, filed Apr. 25, 2017, which claims priority to U.S. patent application Ser. No. 15/138,067, entitled "Strap Tie System," filed Apr. 25, 2016, and claims priority to U.S. patent application Ser. No. 15/175,867, filed Jun. 7, 2016. U.S. patent application Ser. No. 15/589,631, filed May 8, 2017, entitled "Modular Swiveling Strap Tie System," is also a continuation-in-part of U.S. patent application Ser. No. 15/175,867, entitled "Strap Tie System," filed Jun. 7, 2016, which is a continuation of U.S. patent application Ser. No. 15/138,067, entitled "Strap Tie System," filed Apr. 25, 2016, which is a continuation-in-part of U.S. patent application Ser. No. 14/734,846, entitled "Strap Tie System," filed on Jun. 9, 2015. Each of the foregoing applications are herein incorporated by reference in their entirety.

TECHNICAL FIELD

The present disclosure relates generally to the field of strap ties, and more specifically to apparatuses, systems, and methods relating to strap ties.

BACKGROUND

Wounds, such as cuts and lacerations in skin and flesh, are often difficult to close in order to properly treat and heal the wound. Bandages may be used to cover a wound. Wounds may be approximated (i.e., edges of wounds drawn together) using sutures, staples, clips, or topical adhesives. Over time, a wound and/or tissue associated with the wound may retract, reopen, or otherwise lose structural integrity. In some cases, clinical/surgical facilities are not readily accessible for treating a wound.

SUMMARY

According to an aspect of the present disclosure, a strap tie assembly includes a first strap tie including a first base, a first body, and a first strap extending from the first body. The first base is configured to be disposed adjacent to a first portion of skin. The first body includes a first opening and a first engagement member disposed within the first opening. The first strap includes a first proximal end attached to the first body, a first distal end opposite the first proximal end, and a plurality of first movement restriction members disposed along a surface of the first strap. The strap tie assembly also includes a second strap tie including a second base, a second body, and a second strap extending from the second body. The second base is configured to be disposed adjacent to a second portion of skin. The second body includes a second opening and a second engagement member disposed within the second opening. The second strap includes a second proximal end attached to the second body, a second distal end opposite the second proximal end, and a plurality of second movement restriction members disposed along a surface of the second strap. The first opening is configured to receive the second strap, and the first engagement member is configured to engage at least one of the plurality of second movement restriction members of the second strap to prevent translation of the second strap away from the first body. The second opening is configured to receive the first strap, and the second engagement member is configured to engage at least one of the plurality of first movement restriction members of the first strap to prevent translation of the first strap away from the second body.

According to another aspect of the present disclosure, a method of attaching a strap tie system includes detachably securing a first strap tie adjacent to a first portion of skin. The first strap tie includes a first body, a first strap extending from the first body, and a first base extending from the first body. The first body includes a first opening configured to receive a strap and a first engagement member disposed within the first opening. The first strap includes a plurality of first movement restriction members. The method includes detachably securing a second strap tie adjacent to a second portion of skin. The second strap tie includes a second body, a second strap extending from the second body, and a second base extending from the second body. The second body includes a second opening configured to receive a strap and a second engagement member disposed within the second opening. The second strap includes a plurality of second movement restriction members. The method includes receiving the first strap in the second opening. The method includes receiving the second strap in the first opening. The method includes engaging the first engagement member with a candidate second movement restriction member of the second plurality of movement restriction members to prevent translation of the second strap away from the first body. The method includes engaging the second engagement member with a candidate first movement restriction member of the first plurality of movement restriction members to prevent translation of the first strap away from the second body. The candidate first movement restriction member and the candidate second movement restriction member are selected to apply an even amount of force on either side of a wound between the first portion of skin and the second portion of skin.

According to yet another aspect of the present disclosure, a strap tie for securing a wound includes a body, an engagement member, a strap extending from the body, and a base extending from the body. The body includes an opening configured to receive a strap of a remote strap tie. The engagement member is disposed within the opening and configured to engage one of a plurality of movement restriction members of a remote strap tie in order to prevent translation of the remote strap tie away from the body. The strap includes a proximal end attached to the body, a distal end opposite the proximal end, and a plurality of movement restriction members configured to be engaged by an engagement member of a remote strap tie. The base is configured to be disposed adjacent to a portion of skin.

According to yet another aspect of the present disclosure, a strap tie assembly includes a first strap tie and a second strap tie. The first strap tie includes a first base configured to be disposed adjacent to a first portion of skin. The first base can define a first plurality of openings. The first strap tie includes a first body including a first receiving channel and a first engagement member. The first strap tie includes a first strap extending from the first body, the first strap including a first proximal end attached to the first body, a first distal end opposite the first proximal end, and a plurality of first movement restriction members disposed along a surface of the first strap. The first strap defines a first longitudinal axis. The second strap tie includes a second base configured to be disposed adjacent to a second portion of skin. The second base can define a second plurality of openings. The second strap tie includes a second body including a second receiving channel and a second engagement member. The second strap tie includes a second strap extending from the second body, the second strap including a second proximal end attached to the second body, a second distal end opposite the second proximal end, and a plurality of second movement restriction members disposed along a surface of the second strap. The second strap defines a second longitudinal axis. The first receiving channel is configured to receive the second strap. The first engagement member is configured to be rotated about a first rotational axis parallel to the second longitudinal axis to engage at least one of the plurality of second movement restriction members of the second strap to prevent translation of the second strap away from the first body. The second receiving channel is configured to receive the first strap. The second engagement member is configured to be rotated about a second rotational axis parallel to the first longitudinal axis to engage at least one of the plurality of first movement restriction members of the first strap to prevent translation of the first strap away from the second body.

According to yet another aspect of the present disclosure, a strap tie includes a base configured to be disposed adjacent to a portion of skin. The base can define a plurality of openings. The strap tie includes a body including a channel and an engagement member. The strap tie includes a strap extending from the body. The strap include a proximal end attached to the body, a distal end opposite the proximal end, and a plurality of movement restriction members defining a longitudinal axis. The channel is configured to receive a remote strap. The engagement member is configured to be rotated about a rotational axis parallel to a longitudinal axis of the remote strap to engage a movement restriction member of the remote strap to prevent translation of the remote strap away from the body.

According to yet another aspect of the present disclosure, a strap tie assembly includes a first strap tie and a second strap tie. The first strap tie includes a first base configured to be disposed adjacent to a first portion of skin. The first base can define a first plurality of openings. The first strap tie includes a first body including a first receiving channel and a first engagement member. The first strap tie includes a first strap extending from the first body. The first strap defines a first longitudinal axis. The second strap tie includes a second base configured to be disposed adjacent to a second portion of skin. The second base can define a second plurality of openings. The second strap tie includes a second body including a second receiving channel and a second engagement member. The second strap tie includes a second strap extending from the second body. The second strap defines a second longitudinal axis. The first receiving channel is configured to receive the second strap. The first engagement member is configured to be rotated about a first rotational axis parallel to the second longitudinal axis to engage one the second strap to prevent translation of the second strap away from the first body. The second receiving channel is configured to receive the first strap. The second engagement member is configured to be rotated about a second rotational axis parallel to the first longitudinal axis to engage the first strap to prevent translation of the first strap away from the second body.

According to yet another aspect of the present disclosure, a strap tie includes a body including a receiving channel and a strap engagement member. The receiving channel extends through the body. The receiving channel is configured to receive a remote strap. The engagement member is configured to engage a movement restriction member of the remote strap to prevent translation of the remote strap away from the body. The strap extends from the body. The strap includes a proximal end attached to the body, a distal end opposite the proximal end, and a plurality of movement restriction members. The rotational element of the body is configured to removably couple to a base to allow the strap tie to rotate relative to the base.

According to yet another aspect of the present disclosure, a strap tie assembly includes a base and a strap tie. The base includes a base component configured to be disposed adjacent to a portion of skin on a first base side of the base component and a first body coupler coupled to a second base side of the base component opposite the first base side. The strap tie includes a body including a receiving channel and a strap engagement member. The receiving channel extends through the body. The receiving channel is configured to receive a remote strap. The engagement member is configured to engage a movement restriction member of the remote strap to prevent translation of the remote strap away from the body. The strap extends from the body. The strap includes a proximal end attached to the body, a distal end opposite the proximal end, and a plurality of movement restriction members. The rotational element of the body is configured to removably couple to the first body coupler of the base to allow the strap tie to rotate relative to the base.

Some or all of the systems, components, and subcomponents of the present disclosure can be single-use or disposable. Also some or all of the systems, components, and subcomponents of the present disclosure can be made of a unitary construction (formed from a single piece of metal, plastic, or other material) or unitary modular construction (plurality of components and/or subcomponents permanently connected by standard means, such as welding or soldering), or of modular construction (plurality of components and/or subcomponents removably connected by standard means, such as threading or snap-fitting).

These and other features of various embodiments can be understood from a review of the following detailed description in conjunction with the accompanying drawings.

It is to be understood that both the foregoing general description and the following detailed description are explanatory and are not restrictive of the present disclosure, as claimed.

DETAILED DESCRIPTION

Figure 1:
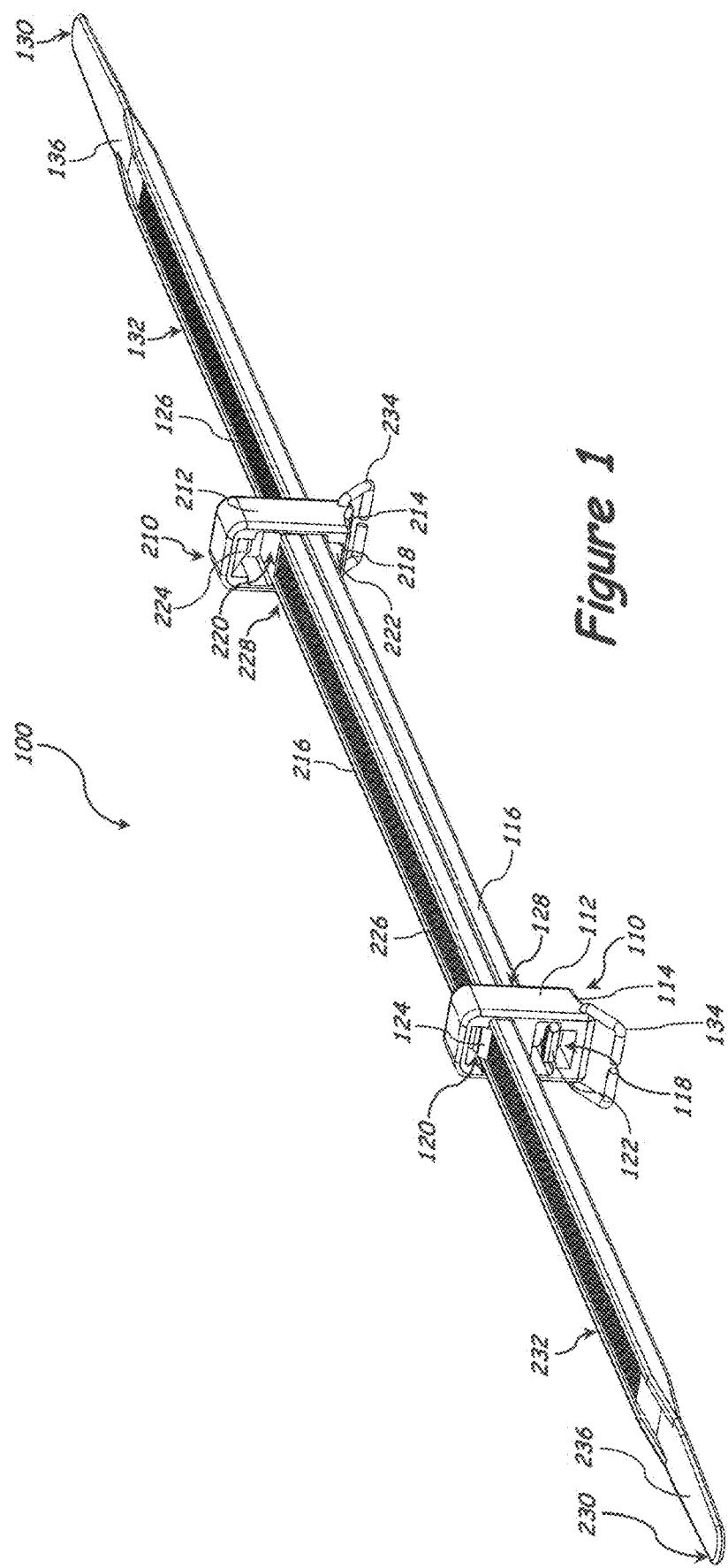
FIG. 1 is a perspective view of an embodiment of a strap tie assembly.

The following detailed description and the appended drawings describe and illustrate various strap tie systems, methods, and components. The description and drawings are provided to enable one of skill in the art to make and use one or more strap tie systems and/or components, and/or practice one or more methods. They are not intended to limit the scope of the claims in any manner.

The use of "e.g." "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "attached" and "coupled" and grammatically related terms refers to the fixed, releasable, or integrated association of two or more elements and/or devices with or without one or more other elements in between. Thus, the term "attached" or "coupled" and grammatically related terms include releasably attaching or fixedly attaching two or more elements and/or devices in the presence or absence of one or more other elements in between. As used herein, the terms "proximal" and "distal" are used to describe opposing axial ends of the particular elements or features being described in relation to anatomical placement.

In existing solutions to treat wounds, uneven forces applied across the wound limit the efficacy of wound healing, such as by causing scars to form. The present solution provides systems, methods, and apparatuses for applying an even amount of force across a wound in order to more effectively heal the wound and limit scar formation. The present solution includes a strap tie assembly including a first strap tie and a second strap tie. The first strap tie includes a first base configured to be disposed adjacent to a first portion of skin, a first body including a first opening and a first engagement member disposed within the first opening, and a first strap extending from the first body. The first strap includes a first proximal end attached to the first body, a first distal end opposite the first proximal end, and a plurality of first movement restriction members disposed along a surface of the first strap. The second strap tie includes a second base configured to be disposed adjacent to a second portion of skin, a second body including a second opening and a second engagement member disposed within the second opening, and a second strap extending from the second body. The second strap includes a second proximal end attached to the second body, a second distal end opposite the second proximal end, and a plurality of second movement restriction members disposed along a surface of the second strap. The first opening is configured to receive the second strap, and the first engagement member is configured to engage one of the plurality of first movement restriction members of the first strap to prevent translation of the first strap away from the second body. The second opening is configured to receive the first strap, and the second engagement member is configured to engage one of the plurality of first movement restriction members of the first strap to prevent translation of the first strap away from the second body. In this way, the tie strap assembly can provide an even amount of force across a wound. The strap tie assembly may include features such as handles, grips, friction elements, etc., which facilitate manipulation of the strap tie assembly in environments where blood, oil (e.g., lipids), or other fluids could impair manipulation. While the present disclosure illustrates use of the strap tie assembly in the context of wound closure, in various embodiments, strap tie assemblies and components thereof may be used in various applications, including but not limited to general use for securing a surface or multiple surfaces; for drawing or pulling surfaces together; for securing homogenous or heterogeneous surfaces; for applying tension to a surface or multiple surfaces; etc.

Referring to FIG. 1, a perspective view of an embodiment of a strap tie assembly 100 is shown. The strap tie assembly 100 includes a first strap tie 110 and a second strap tie 210. The first strap tie 110 includes a first body 112, a first base 114, and a first strap 116. The first base 114 is configured to be disposed adjacent to a first portion of skin. Similarly, the second strap tie 210 includes a second body 212, a second base 214 configured to be disposed adjacent to a first portion of skin, and a second strap 216. In some embodiments, the second strap tie 210 can be identical to the first strap tie 110. In some embodiments, the first strap tie 110 and the second strap tie 210 are generally similar or identical, and configured to interact in a complementary fashion or an opposing fashion. Stated in another way, the components of the first strap tie 110 and the second strap tie 210 can be disposed or configured to engage each other in an identical manner and/or in a mirror image manner.

In some embodiments, the first body 112 includes a pair of first openings 118, 120. The first body 112 includes a pair of first engagement members 122, 124. The first engagement member 122 is disposed within the first opening 118 and the first engagement member 124 is disposed within the first opening 120. Similarly, the second body 212 includes a pair of second openings 218, 220. The second body 212 includes a pair of second engagement members 222, 224. The second engagement member 222 is disposed within the second opening 218 and the second engagement member 224 is disposed within the second opening 220. While the figures illustrate bodies such as first body 112 and second body 212 as including a pair of openings and a pair of engagement members, in various embodiments, various numbers of openings and engagement members may be used (e.g. 1 opening, more than 2 openings, 1 engagement member, more than 2 engagement members, etc.).

In some embodiments, an opening, such as first openings 118, 120 or second openings 218, 220, is disposed such that a path passing through the opening is generally parallel to a longitudinal axis defined by a strap, such as the first strap 116 or the second strap 216. In some embodiments, an opening, such as first openings 118, 120 or second openings 218, 220, is disposed such that a face of the opening is perpendicular to the longitudinal axis defined by the strap. For the sake of clarity, the two openings will be referred to as upper and lower openings (e.g. first lower opening 118, first upper opening 120, second lower opening 218, second upper opening 220), based on the frame of reference shown in FIG. 1, though the strap tie assembly 100 may be configured to be disposed in various orientations based on various frames of reference. For example, as shown in FIG. 1, the first lower opening 118 is disposed or otherwise defined within a first portion of the first body 112 proximate to the first base 114. Similarly, the second lower opening 218 is disposed within a second portion of the second body 212 proximate to the second base 214. The first upper opening 120 is disposed or otherwise defined within a second portion of the first body 112 farther away from the first base 114 relative to the first lower opening 118. Similarly, the second upper opening 220 is disposed or otherwise defined within a second portion of the second body 212 farther away from the second base 214 relative to the second lower opening 218. In some embodiments, the first strap 116 extends from a third portion of the first body 112 that is positioned between the first portion and the second portion of the first body 112. Similarly, in some embodiments, the second strap 216 extends from a third portion of the second body 212 that is positioned between the first portion and the second portion of the second body 212. In some embodiments, the third portion of the second body 212 separates the first portion of the second body 212 from the second portion of the second body 212.

In some embodiments, the plurality of movement restriction members (e.g., movement restriction members 126, movement restriction members 226, etc.) includes a plurality of ridges. The ridges may define a plurality of grooves (e.g., recesses, cavities, etc.). In some embodiments, the plurality of movement restriction members (e.g., movement restriction members 126, movement restriction members 226, etc.) includes a plurality of holes; a corresponding engagement member (e.g., engagement member 122, etc.) may include a hook or other structure configured to engage a hole.

Referring back to FIG. 1, the first strap 116 extends from the first body 112. The first strap 116 includes a first proximal end 128 attached to the first body 112 and a first distal end 130 opposite the first proximal end 128. The first strap 116 includes a plurality of first movement restriction members 126 disposed along a surface 132 of the first strap 116. Similarly, the second strap tie 210 includes a second strap 216 extending from the second body 212. The second strap 216 includes a second proximal end 228 attached to the second body 212 and a second distal end 230 opposite the second proximal end 228. The second strap 216 includes a plurality of second movement restriction members 226 disposed along a surface 232 of the second strap 216. Additional details pertaining to the interactions between the first engagement member and the first movement restriction members and the second engagement member and the second movement restriction members are provided below.

Each of the pair of first openings 118, 120 is configured to receive the second strap 216. Each of the pair of first engagement members 122, 124 is configured to engage one of the plurality of second movement restriction members 226 of the second strap 216. For example, as shown in FIG. 1, the second strap 216 has been received through the first opening 120. The first engagement member 124 has engaged one of the plurality of second movement restriction members 226.

The engagement between an engagement member and a movement restriction member, such as between the first engagement member 124 and the second movement restriction member 226, can prevent translation of the second strap 216 away from the first body 112. For example, the engagement may only allow the second strap 216 to move in a single direction relative to the first body 112, such that the second body 212 can only be drawn towards the first body 112 as the second strap 216 is received through one of the first openings 118, 120.

Each of the pair of second openings 218, 220 is configured to receive the first strap 116. Each of the pair of second engagement members 222, 224 is configured to engage one of the plurality of first movement restriction members 126 of the first strap 116. For example, as shown in FIG. 1, the first strap 116 has been received through the second opening 218. The second engagement member 222 has engaged one of the plurality of first movement restriction members 126.

In some embodiments, a strap (e.g., first strap 116, second strap 216, etc.) is received by a corresponding opening by first passing the distal end of the strap through the corresponding opening, followed by passing the length of the strap through the opening up to a particular movement restriction member.

Similar to the engagement between the first engagement members 122, 124 and the second movement restriction members 226, the engagement between the second engagement members 222, 224 and the first movement restriction members 126 can prevent translation of the first strap 116 away from the second body 212. For example, the engagement between the first engagement members 122, 124 and the second movement restriction members 226 may only allow the first strap 116 to move in a single direction relative to the second body 212. As such, the first body 112 can only be drawn towards the second body 212 as the first strap 116 is received through one of the second openings 218, 220. Stated in other words, such an engagement prevents translation of the first strap 116 away from the second body 212 by preventing a motion between the first strap 116 and the second body 212 in which the first strap tie 110 and the second strap tie 210 are separated and/or in which the first body 112 and the second body 212 are drawn away from each other.

Similarly, the engagement between the second engagement members 222,224 and the first movement restriction members 126 may only allow the second strap to move in a single direction relative to the second body 212. As such, the second body 212 can only be drawn towards the first body 112 as the second strap 216 is received through one of the first openings 118, 120. Stated in other words, such an engagement prevents translation of the second strap 216 away from the first body 112 by preventing a motion between the second strap 216 and the first body 112 in which the second strap tie 210 and the first strap tie 110 are separated and/or in which the first body 112 and the second body 212 are drawn away from each other.

In some embodiments, an engagement member such as engagement member 222 is configured to removably engage a corresponding movement restriction member 126. For example, the engagement member 222 may be mechanically coupled to a release member that disengages the engagement member 222 from the movement restriction member 126 when the release member is actuated.

In some embodiments, the first strap tie 110 includes a first handle 136 disposed at the first distal end 130 of the first strap 116. As shown in FIG. 1, the first handle 136 has a tapered shape (e.g., tapers to a thin shape at the first distal end 130), facilitating the passing of the first strap 116 through an opening such as the second opening 218. In some embodiments, the first handle 136 is detachably coupled to the first strap 116.

In some embodiments, similar to the first strap tie 110, the second strap tie 210 includes a second handle 236 disposed at the second distal end 230 of the second strap 216. As shown in FIG. 1, the second handle 236 has a tapered shape (e.g., tapers to a thin shape at the distal end 230), facilitating the passing of the second strap 216 through an opening such as the first opening 120. In some embodiments, the second handle 236 is detachably coupled to the second strap 216.

Handles, such as the first handle 136 and the second handle 236 may include a high-friction surface, such as a surface with ridges or other protrusions, facilitating gripping of the handles by a user. Handles may include a grip shaped to conform to the hand of a user, such as a pistol grip. Handles may be integrally formed with associated straps, such as being extruded as a single piece. Handles may be detachably coupled by having complementary mating features with associated straps. For example, a handle may include a male protrusion configured to engage a female receiver provided on a distal end of a corresponding strap, or vice versa. A strap may be provided with a universal receiver or a universal protrusion, allowing the strap to be engaged to a variety of handles.

In some embodiments, the first strap tie 110 includes an attachment member configured to attach the first strap tie 110 to a portion of skin (e.g., a first portion of skin along a first side of a wound), such as an attachment member 134 disposed proximate to the base 114. The attachment member 134 may secure the strap tie 110 to the portion of skin. In some embodiments, the attachment member 134 may detachably secure, attach, or otherwise couple the strap tie 110 to the portion of skin. For example, the attachment member 134 can be an adhesive or staple that is removable and therefore can detachably secure the strap tie 110 to the portion of the skin. The attachment member 134 can secure the strap tie 110 temporarily. In some embodiments, the strap tie 110 can be permanently secured to the portion of skin (e.g., detachably secured, removably secured, temporarily secured, permanently secured, etc.). As shown in FIG. 1, the attachment member 134 is provided as a staple. In various embodiments, the attachment member 134 may be provided using various implements (e.g., staples, hooks, adhesives, etc.).

Similar to the first strap tie 110, in some embodiments, the second strap tie 210 includes an attachment member configured to attach the second strap tie 210 to a portion of skin (e.g., a second portion of skin along a second side of a wound), such as an attachment member 234 disposed proximate to the base 214. The attachment member 234 may secure the strap tie 210 to the portion of skin. In some embodiments, the attachment member 234 may detachably secure, attach, or otherwise couple the strap tie 210 to the portion of skin. For example, the attachment member 234 can be an adhesive or staple that is removable and therefore can detachably secure the strap tie 210 to the portion of skin. The attachment member 234 can secure the strap tie 210 temporarily. In some embodiments, the strap tie 210 can be permanently secured to the portion of skin (e.g., detachably secured, removably secured, temporarily secured, permanently secured, etc.). As shown in FIG. 1, the attachment member 234 is provided as a staple. In various embodiments, the attachment member 234 may be provided using various implements (e.g., staples, hooks, adhesives, etc.).

In some embodiments, as shown in FIG. 1, when the first strap 116 has been received through the second opening 218 and the second strap 216 has been received through the first opening 120, the first strap 116 and the second strap 216 are disposed substantially parallel to each other. In some embodiments, straps are disposed substantially parallel when they follow a similar path while being disposed proximate to each other when the strap ties 110, 210 are engaged. For example, a plane passing through the first strap 116 that is perpendicular to the first movement restriction members 126 of the first strap 116 may be parallel to a plane passing through the second strap 216 that is perpendicular to the second movement restriction members 226 of the second strap 216. At the same time, any given movement restriction member of a strap has an adjacent movement restriction member of the other strap disposed above or below, depending on which strap has been received into an upper opening of the other strap. In some embodiments, straps are disposed substantially parallel to each other when the straps would be aligned and adjacent to each other when drawn taut. In some embodiments, the first strap 116 and the second strap 216 are disposed in contact with each other.

In some embodiments, the straps 116, 216 can be substantially parallel even when they include flexible material. For example, the strap tie assembly 100 may undergo transient perturbations in configuration, orientation, shape, etc. during use; nevertheless, over time the straps 116, 216 will remain substantially parallel as described above.

In some embodiments, the straps 116, 216 are drawn taut once received by an opening in an opposing strap tie (e.g. strap ties 110, 210), because the distance between the first body 112 and the second body 212 corresponds to the lengths of the segments of the straps 116, 216 that are disposed between the first body 112 and the second body 212 (e.g., in an inner/interior region of the strap tie assembly 100).

In some embodiments, the first body 112 and the second body 212 are disposed on a region of skin (e.g. a region of skin including a first portion of skin, a wound, and a second portion of skin) that includes a curved profile. The first strap 116 and the second strap 216 may be substantially parallel by maintaining straight paths (e.g., paths of shortest distance) between the first body 112 and the second body 212 once received by the appropriate opening in an opposing strap tie. In some embodiments, substantially parallel includes a tolerance of a small difference in angle between the vectors defined by two components (e.g. less than 30 degrees, less than 20 degrees, less than 10 degrees, less than 5 degrees, less than 1 degree, etc.).

Figure 2:
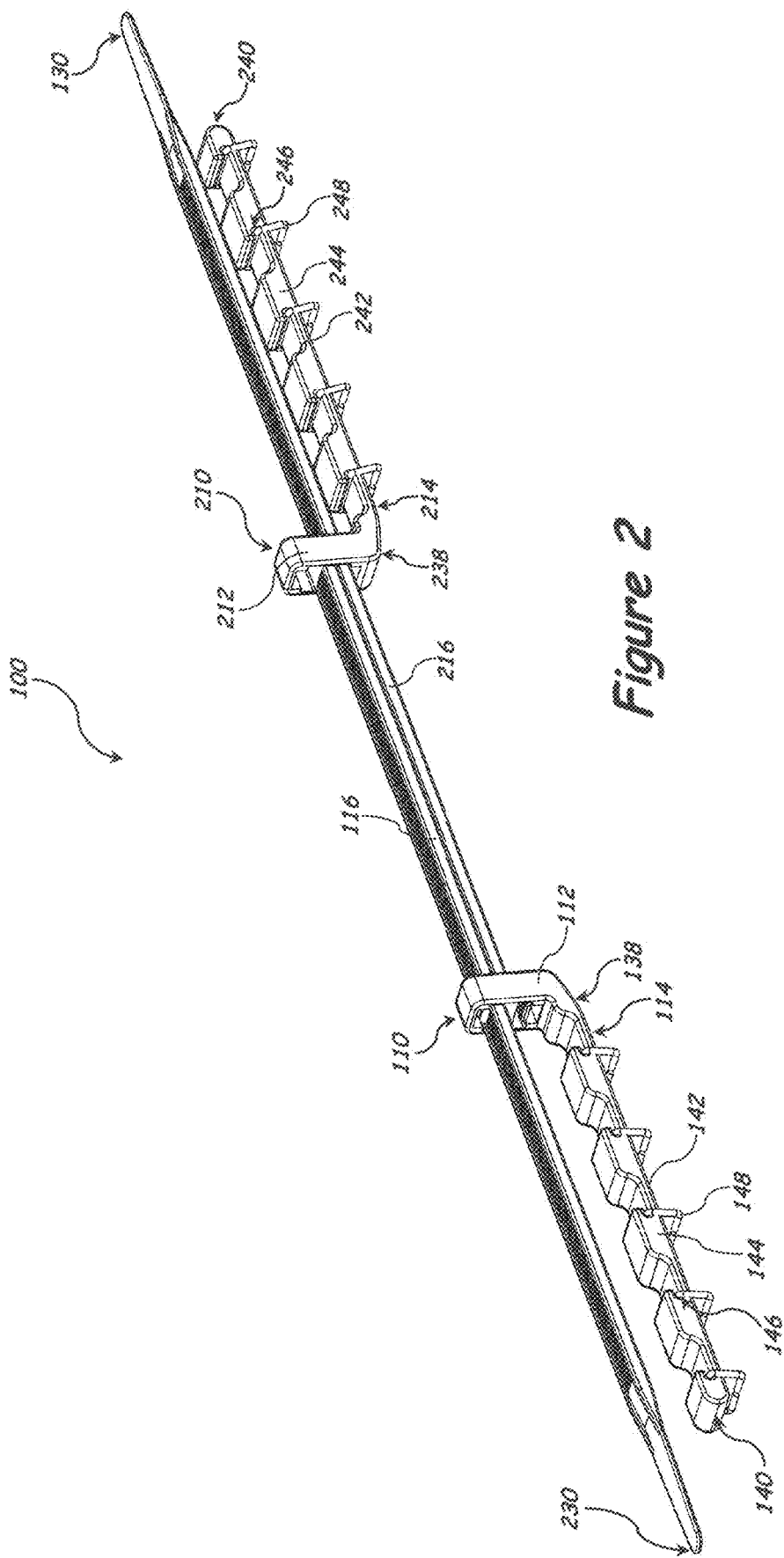
FIG. 2 is a perspective view of an embodiment of a strap tie assembly having an extended base portion.

Referring now to FIG. 2 a perspective view of an embodiment of the strap tie assembly 100 is shown with the first base 114 and the second base 214 having extended base sections. In some embodiments, the first base 114 includes a first base extension 142 extending between a first proximal base end 138 and a first distal base end 140. The first proximal base end 138 is disposed proximate to the first body 112 of the first strap tie 110. The first base 114 may include a first base holder 144 protruding from a length of the first base extension 142. The first base holder 144 includes a groove 146 configured to hold a first base attachment member 148. The first base attachment member 148 may be similar in structure and function to the attachment member 134 shown in FIG. 1. A single first base attachment member 148, or a plurality of first base attachment members 148, may be provided to attach the first base extension 142 (and thus attach the first strap tie 110) to a portion of skin, facilitating the application of an even amount of force across a wound when the strap tie assembly 100 is used to secure or close a wound. While FIG. 2 shows the first base attachment members 148 as staples, the first base attachment members 148 need not be provided as identical implements.

In some embodiments, similar to the first base 114, the second base 214 includes a second base extension 242 extending between a second proximal base end 238 and a second distal base end 240. The second proximal base end 238 is disposed proximate to the second body 212 of the second strap tie 110. The second base 214 may include a second base holder 244 protruding from a length of the second base extension 242. The second base holder 244 includes a groove (e.g., hole, cavity, recess, depression, etc.) such as a groove 246 configured to hold a second base attachment member 248. The second base attachment member 248 may be similar in structure and function to the attachment member 234 shown in FIG. 1. A single second base attachment member 248, or a plurality of second base attachment members 248, may be provided to attach the second base extension 242 (and thus to attach the second strap tie 210) to a portion of skin, facilitating the application of an even amount of force across a wound when the strap tie assembly 100 is used to secure or close a wound. While FIG. 2 shows the second base attachment members 248 as staples, the second base attachment members 248 need not be provided as identical implements. In various embodiments, the strap ties 110, 210 may be secured to portions of skin at various distances from the wound, in order to apply a specific or selected tension (e.g., in order to apply an even amount of force across the wound).

As shown in FIG. 2, the first base extension 142 extends in a direction substantially parallel to the portion of the second strap 216 disposed between the first body 112 and the second distal end 230 of the second strap 216 (e.g., an outside portion of the second strap 216) when the second strap 216 has been received by and passed through the first body 112. The first base extension 142 similarly extends in a direction perpendicular to a plane defined by one or both of the faces of the openings 118, 120. The direction may be substantially parallel similar to a manner as described above for the orientation relationship between the first strap 116 and the second strap 216 when the straps 116, 216 have been received by openings of an appropriate strap tie. In some embodiments, the direction is substantially parallel when the vectors corresponding to the angles at which the first base extension 142 extends from the first body 112 and the outside portion of the second strap 216 exits the first body 112 are substantially parallel.

The first base extension 142 extends in a direction substantially opposite to that of the first strap 116 (e.g., the first strap 116 extends from the first body 112 towards the second body 212 so that the second body 212 may receive the first strap 116, whereas the first base extension 142 extends away from the second body 212).

Similar to the first base extension 142, the second base extension 242 extends in a direction generally parallel to the portion of the first strap 116 disposed between the second body 212 and the second distal end 130 of the first strap 116 (e.g., an outside portion of the first strap 116) when the first strap 116 has been received by and passed through the second body 212. The second base extension 242 similarly extends in a direction perpendicular to a plane defined by one or both of the faces of the second openings 218, 220. The second base extension 242 extends in a direction generally opposite the second strap 216 (e.g., the second strap 216 extends from the second body 212 towards the first body 112 so that the first body 112 may receive the second strap 216, whereas the second base extension 242 extends away from the first body 112).

Figure 3:
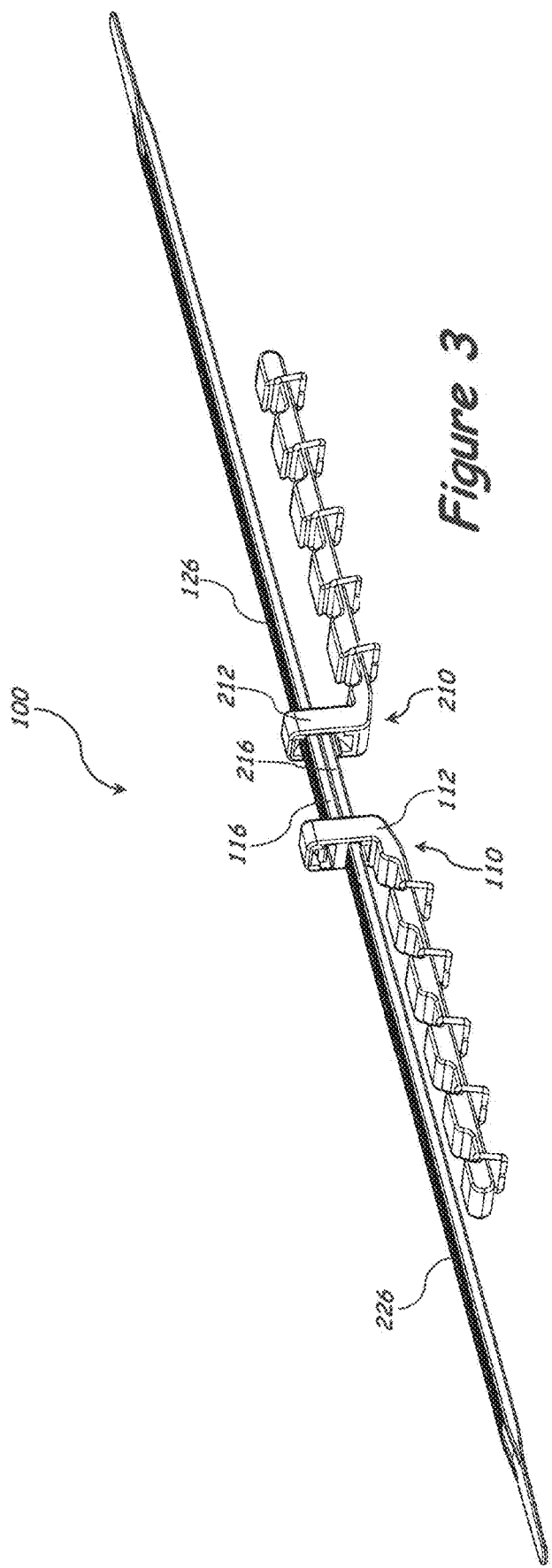
FIG. 3 is a perspective view of an embodiment of the strap tie assembly of FIG. 2 in an adjusted configuration in which a first strap tie and a second strap tie have been drawn more closely together.
Figure 4:
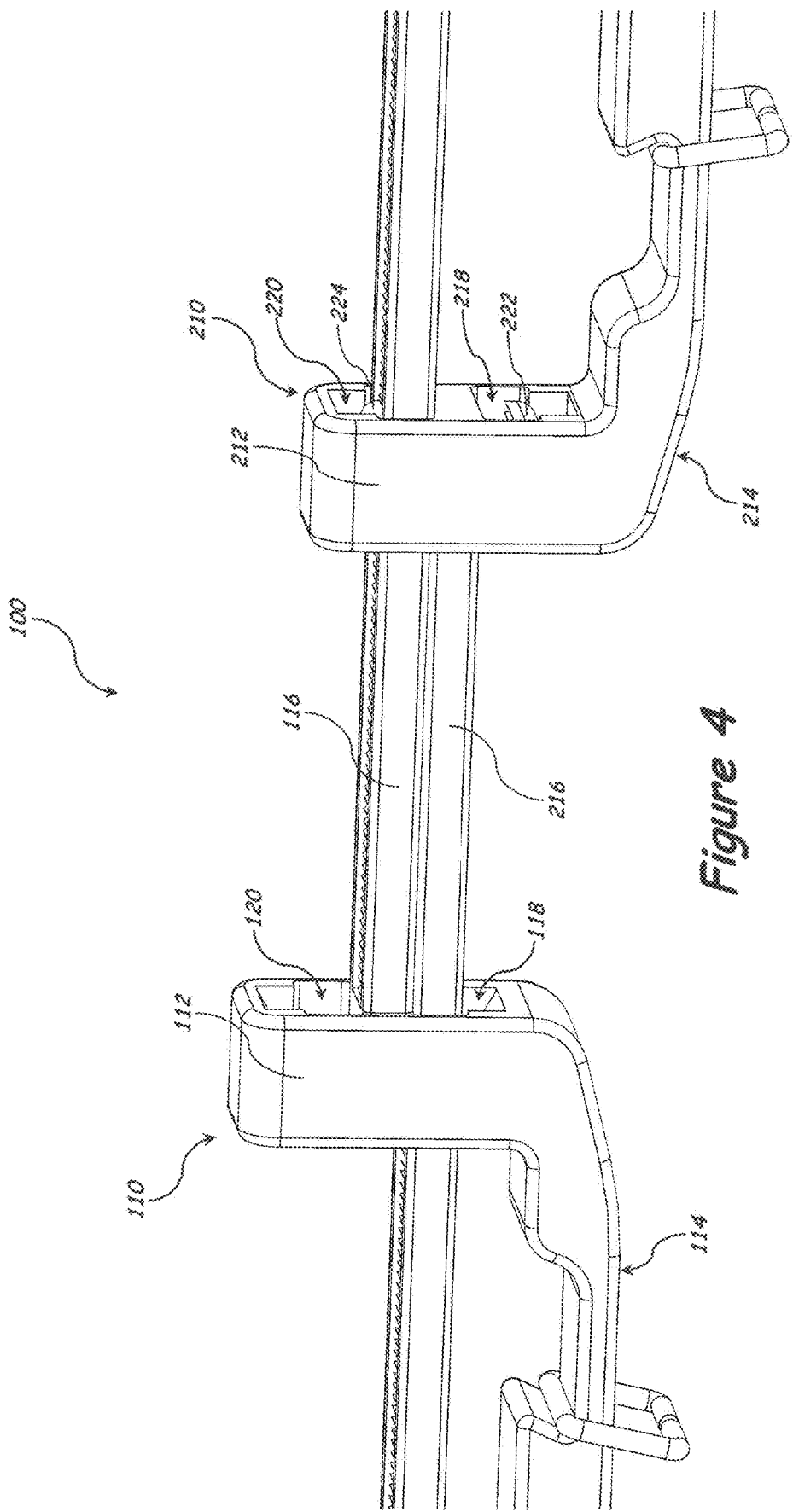
FIG. 4 is a detailed perspective view of an embodiment of various components of the strap tie assembly of FIG. 2 as shown in the configuration of FIG. 3.
Figure 5:
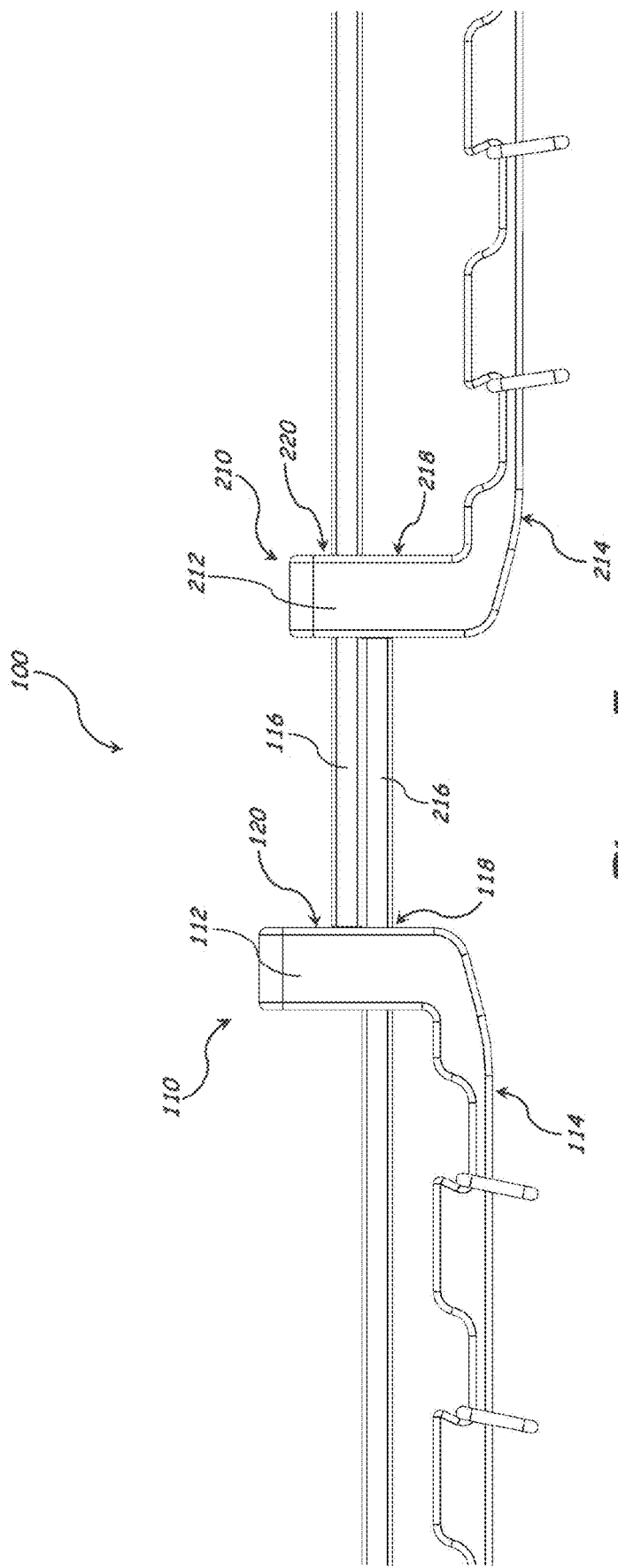
FIG. 5 is a detailed side view of an embodiment of various components of the strap tie assembly of FIG. 2 as shown in the configuration of FIG. 3.

Referring now to FIGS. 3-5, embodiments of the strap tie assembly 100 are shown in which the strap tie assembly 100 is disposed in a configuration in which the first strap tie 110 and the second strap tie 210 are drawn together more closely than in FIG. 2. That is, after the first strap 116 has been received and passed through the second upper opening 200 and the second strap 216 has been received and passed through the first lower opening 118, the first strap 116 and the second strap 216 have been translated (e.g., pulled, drawn, etc.) further in opposite directions, tightening the strap tie assembly 100. For example, a user may grasp the first strap 116 and the second strap 216 at the first handle 136 and the second handle 236, respectively, and apply force to the first strap 116 and the second strap 216 in opposite directions (e.g., draw the first handle 136 away from the second body 212 and draw the second handle 236 away from the first body 112, etc.).

In some embodiments, the first base 114 has been secured to a first portion of skin disposed on one side of a wound, and the second base 214 has been secured to a second portion of skin disposed on another side of a wound; drawing the first strap 116 and the second strap 216 apart (e.g., in opposite directions) results in the wound being drawn together to be closed, as the first portion of skin and the second portion of skin are drawn together due to force applied to the first base 114 and the second base 214 via the first strap 116 and the second strap 216.

In some embodiments, the interaction between the engagement members of the strap ties 110, 210 (e.g., engagement members 122, 124, 222, 224 shown in FIG. 1, etc.) and the movement restriction members of the strap ties 110, 210 (e.g., movement restriction members 126, 226, etc.) allows a user to adjust the position of the strap ties 110, 210 relative to the bodies 112, 212 in specific and/or discrete amounts. For example, in some embodiments, a user may count or otherwise keep track of the distance a strap has been drawn through a body of a remote strap tie (e.g., strap 116 and body 212 of remote strap tie 210, etc.) based on the number movement restriction members 126, 226 that have been passed through the bodies 212, 112, respectively.

In some embodiments, the movement restriction members 126 and/or the movement restriction members 226 are spaced in a specific pattern, allowing the manipulation of the strap ties 110, 210, and thus the force applied across a wound, to be controlled and adjusted in a specific manner. For example, in some embodiments, the movement restriction members proximate to a body (e.g., the first movement restriction members 126 of first strap 116 proximate to the first body 112 of the first strap tie 110, etc.) may be spaced apart by relatively large amounts, allowing for the strap to be translated in relatively large amounts through a remote body, while the movement restriction members distal from the body may be spaced apart by relatively small amounts, allowing for the strap to be translated in relatively small amounts through the remote body. In some embodiments, the movement restriction members are spaced apart equally.

Figure 6:
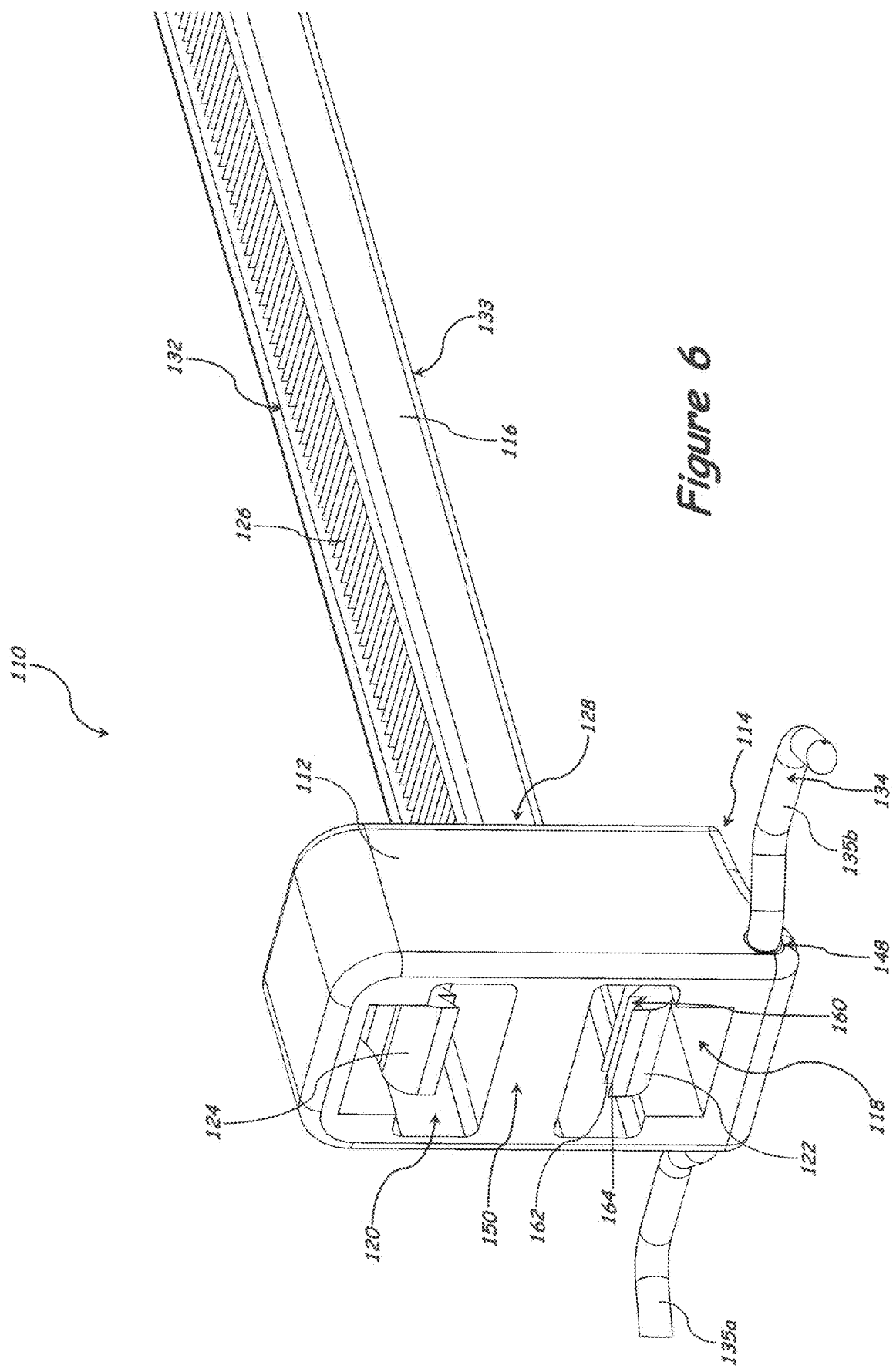
FIG. 6 is a perspective end view of an embodiment of a strap tie and various components of the strap tie including a body, a strap, openings, engagement members, and an attachment member.

Referring now to FIG. 6, a detailed perspective view of an embodiment of a strap tie 110 is shown. The strap tie 110 includes a body 112, a base 114 configured to be disposed adjacent to a portion of skin, and a strap extending from the body 112. The strap tie 110 also includes an upper opening 120 and a lower opening 118. Each of the openings 118, 120 are configured to receive a strap from a remote strap tie (e.g., strap tie 210, etc.). The strap tie 110 also includes an upper engagement member 124 disposed within the upper opening 120, and a lower engagement member 122 disposed within the lower opening 118. As shown in FIG. 6, the engagement members 122, 124 are disposed in opposing directions; the upper engagement member 124 and the lower engagement member 122 each curve towards a central face 150 disposed between the upper opening 120 and the lower opening 118. As such, each of the openings 118, 120 may receive a strap (e.g., second strap 216 shown in FIGS. 1-5, etc.), between the central face 150 and the respective engagement member 122, 124.

As shown in FIG. 6, the upper engagement member 124 and the lower engagement member 122 are each provided as a pawl. For example, the lower engagement member includes a recess 160 defined by a vertical edge 162 and an angled edge 164. When a movement restriction member of a remote strap tie (e.g., movement restriction member 226 shown in FIG. 1, etc.) engages the lower engagement member 122, the movement restriction member 226 fits into (e.g., is received by, engages, removably couples to, etc.) the recess 160. The engagement between the lower engagement member 122 and the movement restriction member 226 allows translation of the strap associated with the movement restriction member 226 (e.g., strap 216 shown in FIG. 1, etc.) in one direction, when the movement restriction member 226 slides along the angled edge 164, while preventing translation of the movement restriction member 226 in another direction (e.g., an opposite direction), when the movement restriction member 226 abuts the vertical edge 162.

In some embodiments, the movement restriction members 126 are disposed at an angle, facilitating an engagement with the engagement member 122 in which the remote strap (e.g., strap 216 shown in FIG. 1, etc.) is prevented from being translated away from the body 112. In some embodiments, the movement restriction members 126 are provided on multiple outer surfaces of the strap 116, such as an upper surface 132 and a lower surface 133. For example, the movement restriction members 126 may originate in pairs from a central body of the strap 116. The movement restriction members 126 may be provided as single movement restriction members that pass through from the upper surface 132 to the lower surface 133. As such, both the upper surface 132 and the lower surface 133 of the strap 116 may be engaged by an engagement member of a remote strap (e.g., engagement member 222 shown in FIG. 1, etc.). This underscores the modularity of the strap tie assembly 100, as the strap ties 110, 210 may be interchangeably manipulated and engaged. Such modular features facilitate using the strap tie assembly 100 in situations when the strap tie assembly 100 is to be quickly implemented, including but not limited to trauma or battlefield situations.

Figure 7:
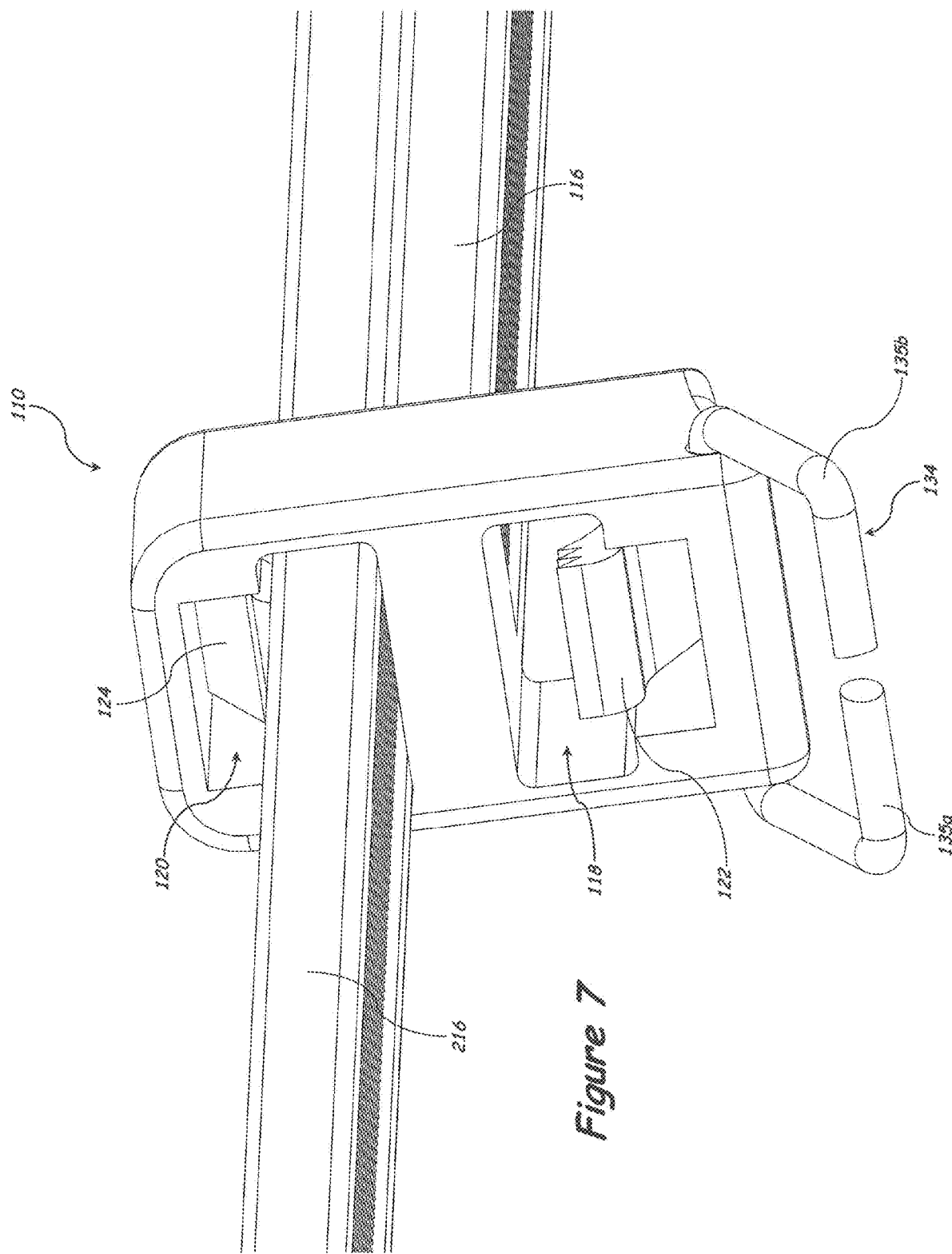
FIG. 7 is a detailed perspective view of an embodiment of a strap tie in which the strap tie has received a remote strap.

Referring now to FIG. 7, a detailed perspective view of an embodiment of the strap tie 110 (e.g., a first strap tie 110, etc.) receiving a remote strap 216 (e.g., a second strap 216 as shown in FIG. 1, etc.) is shown. The remote strap 216 has been received through upper opening 120 and engaged by engagement member 124. In various embodiments, the remote strap 216 may also be received through lower opening 118 and engaged by engagement member 122.

Referring further to FIGS. 6-7, the attachment member 134 is shown as contrasted between a pre-secured state and a secured state. As shown in FIG. 6, the attachment member includes two attachment arms 135*a*, 135*b*. As shown in FIG. 7, the attachment arms 135*a*, 135*b* have been translated/shifted, such as in order to attach the attachment member 134 to a portion of skin. For example, as shown in FIGS. 6-7, the attachment member 134 is a staple, which may be attached to a portion of skin using a tool such as a staple gun, etc.

Figure 8:
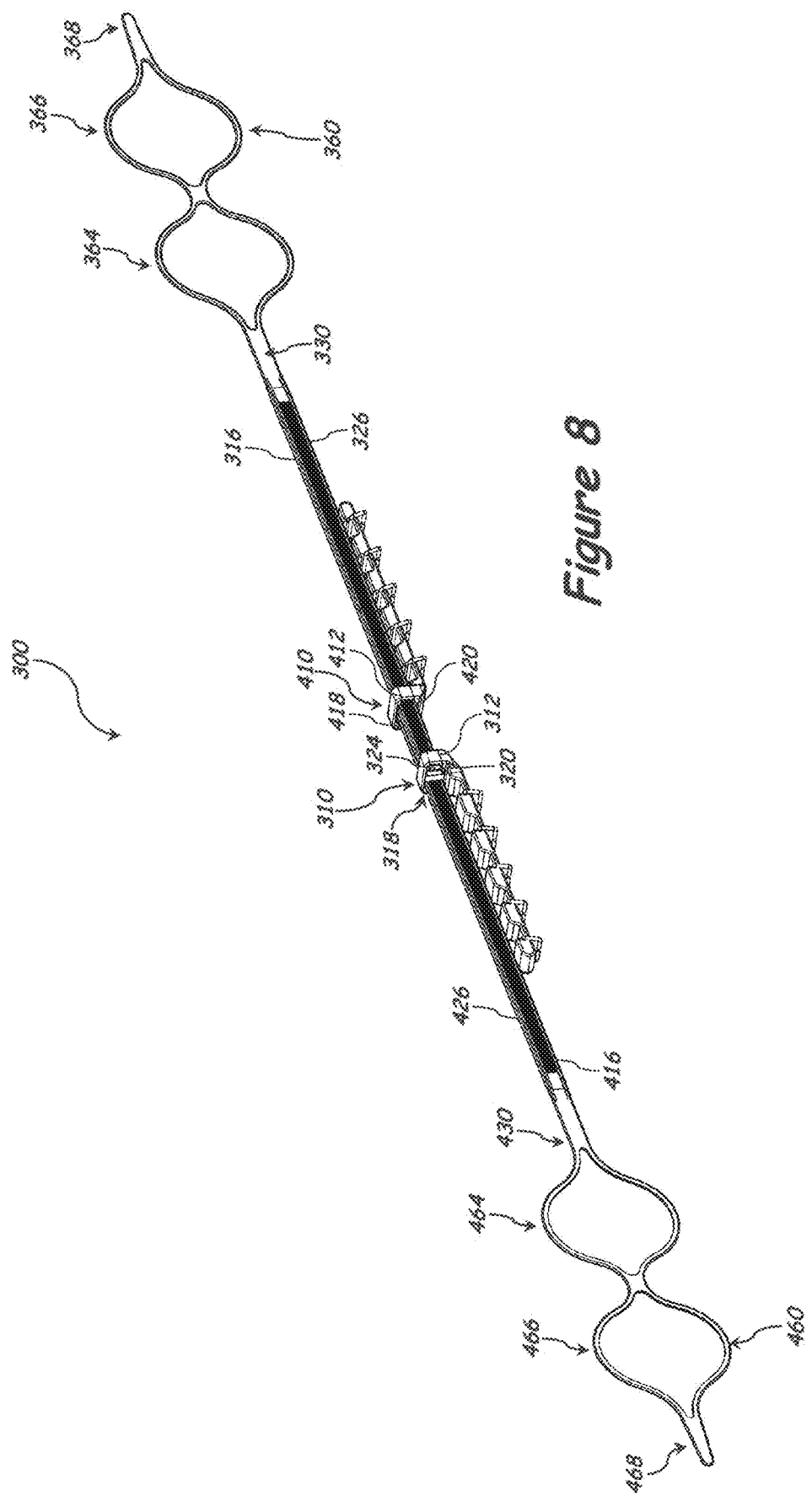
FIG. 8 is a perspective view of an embodiment of a strap tie assembly in which each strap tie includes a loop handle and a pair of openings disposed in a side-by-side configuration.
Figure 9:
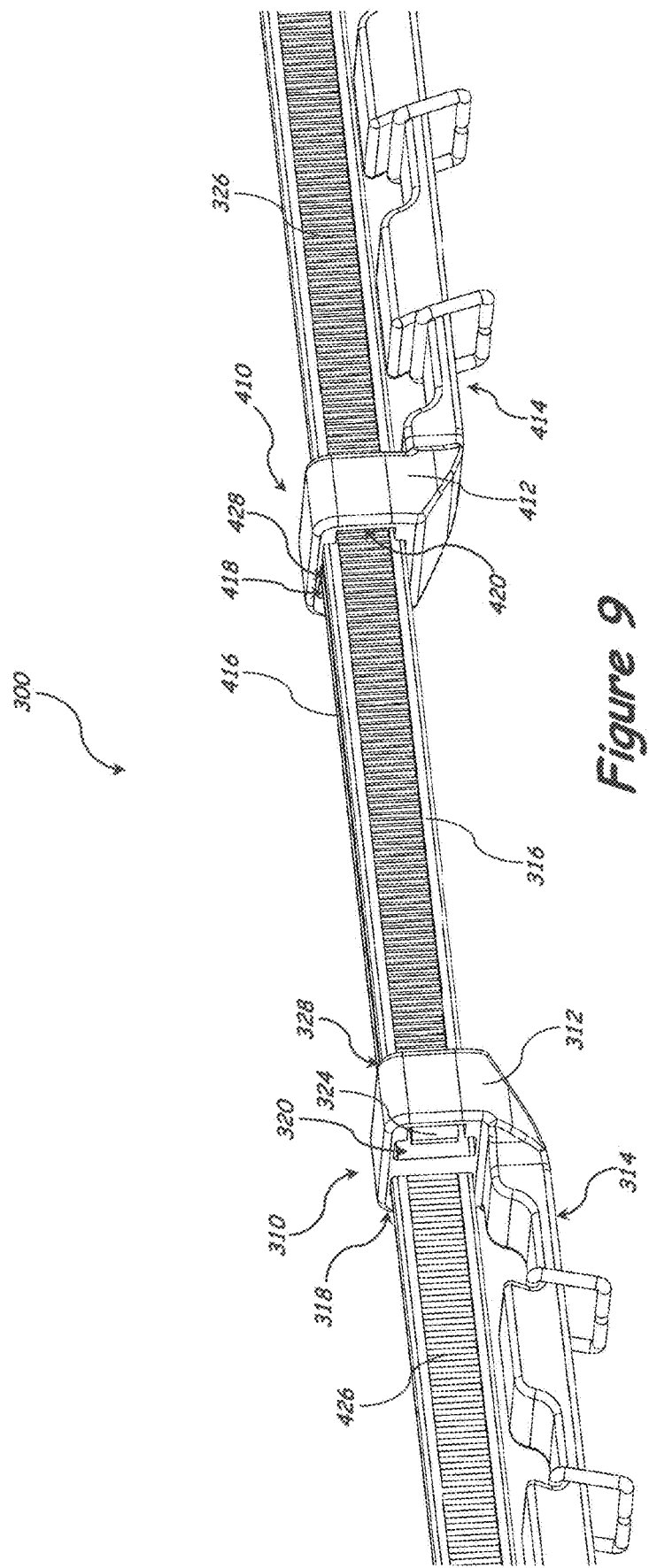
FIG. 9 is a detailed perspective view of an embodiment of the strap tie assembly of FIG. 8.

Referring now to FIGS. 8-9, a strap tie assembly 300 is shown. The strap tie assembly 300 is similar in function to the strap tie assembly 100 shown in FIGS. 1-7. FIG. 8 shows a perspective view of an embodiment of the strap tie assembly 300. FIG. 9 shows a detailed perspective view of an embodiment of the strap tie assembly 300. The strap tie assembly 300 includes a first strap tie 310 and a second strap tie 410. The first strap tie 310 includes a first body 312, a first strap 316 attached to and/or extending from the first body 312, and a first base 314 attached to and/or extending from the first body 312. The first body 312 includes a first left opening 318 and a first right opening 320 disposed proximate to the first proximal end 328 of the first strap 316. Similarly, the second strap tie 410 includes a second body 412, a second strap 416 attached to and/or extending from the second body 412, and a second base 414 attached to and/or extending from the second body 412. The second body 412 includes a second left opening 418 and a second right opening 420 disposed proximate to the second proximal end 428 of the second strap 416. Such a configuration of openings in the first body 312 and the second body 412 may be referred to as "side-by-side," based on the positions of the openings relative to each other and the respective bases 314, 414 of the bodies 312, 412 (in comparison, the openings 118, 120 and 218, 220 as shown in FIGS. 1-7 may be considered to have upper/lower positions relative to each other and the respective bases 114, 214 of the bodies 112, 212). In some embodiments, a plane passing through the openings of a body (e.g., first left opening 318 and first right opening 320 of first body 312; second left opening 418 and second right opening 320 of second body 412, etc.) is perpendicular to a longitudinal axis defined by a strap (e.g., strap 316, strap 416, etc.) and/or parallel to a transverse axis passing through both the first strap 316 and the second strap 416 when the first strap 316 and the second strap 416 have been received by an opposite (e.g., complementary, etc.) strap tie. The first strap 316 includes first movement restriction members 326, and the second strap 416 includes second movement restriction members 426.

The first body 312 may include an engagement member disposed in each of the first left opening 318 and the first right opening 320, such as an engagement member 324. The second body 412 may include an engagement member disposed in each of the second left opening 418 and the second right opening 420. Engagement members of the strap tie assembly 300, such as the engagement member 324, are similar in structure and function to the engagement members of the strap tie assembly 100.

As shown in FIG. 8, the first strap 316 includes a first loop handle 360 disposed at a distal end 330 of the first strap 316. The first loop handle 360 includes loops 364, 366 disposed between the distal end 330 of the first strap 316 and a distal end 368 of the first loop handle 360. Similar to the first loop handle 360, the second loop handle 460 includes loops 464, 466 disposed between the distal end 430 of the second strap 416 and a distal end 468 of the second loop handle 460. The first loop handle 360 and the second loop handle 460 facilitate manipulation of the straps 316, 416, for example, by providing handles to a user which are easy to grip and manipulate. While FIG. 8 shows the loop handles 360, 460 disposed in a plane generally containing the straps 316, 416, in various embodiments, the loop handles 360, 460 may be disposed in various orientations. In some embodiments, the strap tie assembly 300 includes flexible or malleable material (e.g., material that may yield or be rotated, etc.), allowing the loop handles 360, 460 to be manipulated at various angles. The loop handles 360, 460 may include material allowing the loop handles 360, 460 to be reduced in size (e.g., compressed, squeezed, etc.) so that the loop handles 360, 460 may be passed through an opening of a strap tie.

Figure 10:
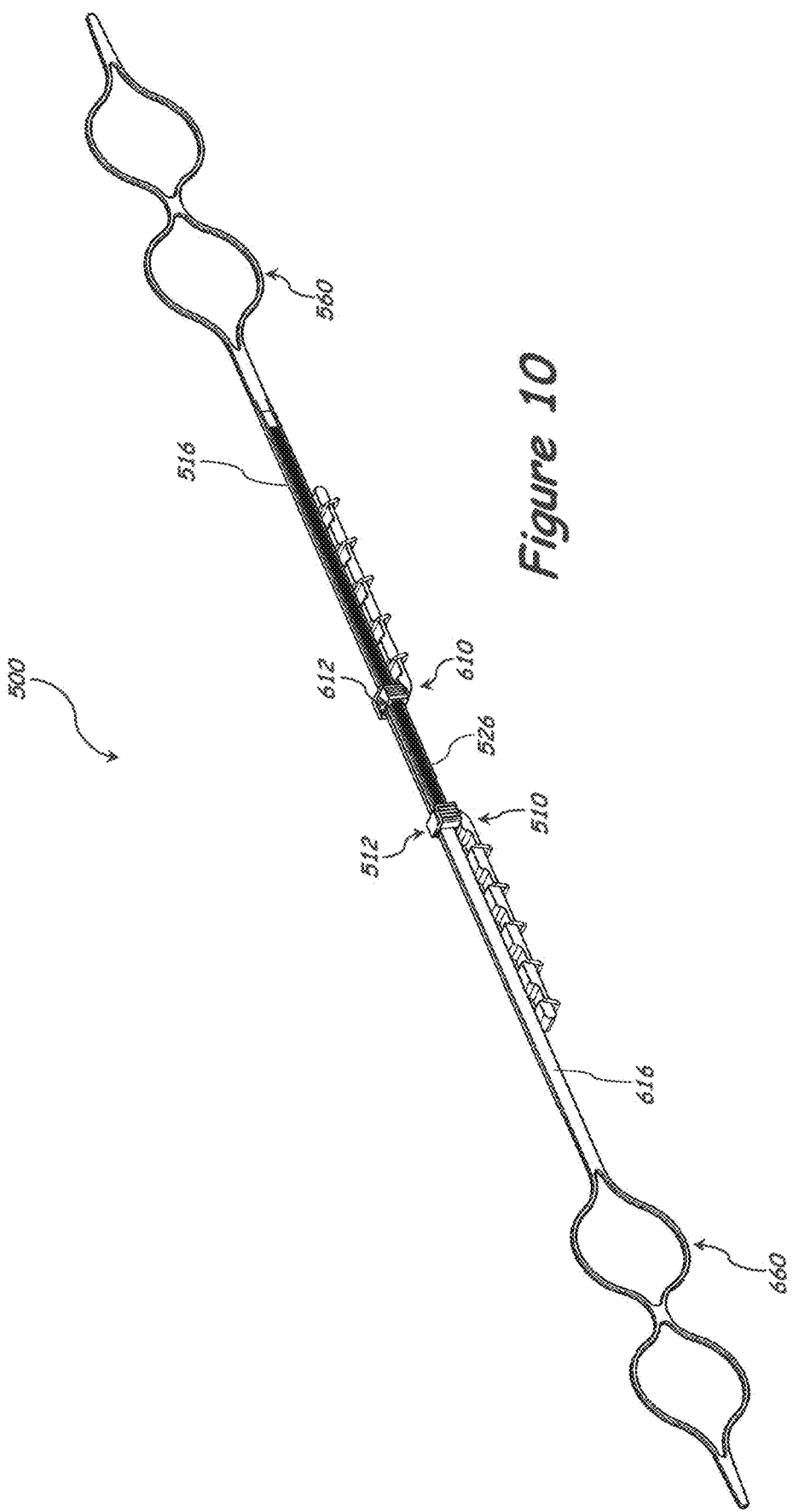
FIG. 10 is a perspective view of an embodiment of a strap tie assembly in which each strap tie includes a loop handle and a pair of bodies for receiving a strap of another strap tie.
Figure 11:
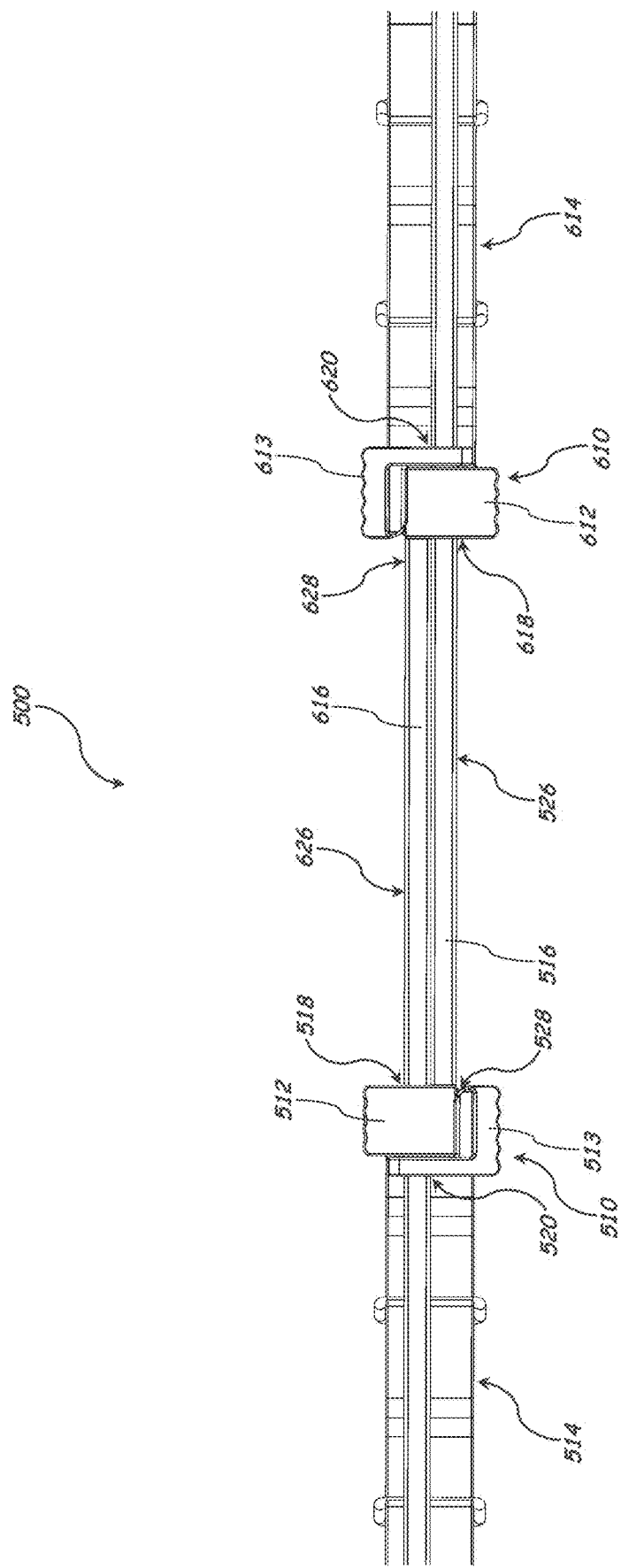
FIG. 11 is a top view of an embodiment of the strap tie assembly of FIG. 10.

Referring now to FIGS. 10-11, a strap tie assembly 500 is shown. The strap tie assembly 500 is similar in structure and function to the strap tie assembly 300 shown in FIGS. 8-9. FIG. 10 is a perspective view of the strap tie assembly 500. The strap tie assembly 500 includes a first strap tie 510 and a second strap tie 610. As shown in FIG. 10, the strap tie assembly 500 includes a first loop handle 560 attached to a first strap 516, and a second loop handle 660 attached to a second strap 616.

FIG. 11 is a top view of an embodiment of the strap tie assembly 500. The first strap tie 510 includes a first inner body 512, a first outer body 513, a first strap 516 attached to and/or extending from the first inner body 512, and a first base 514. Similar to the first strap tie 510, the second strap tie 610 includes a second inner body 612, a second outer body 613, a second strap 616 attached to and/or extending from the second inner body 612, and a second base 614. The inner bodies 512, 612 are disposed on an "interior" of the strap tie assembly 500 (e.g., the region of the strap tie assembly 500 between the inner bodies 512, 612 is an interior or inner region, in which the straps 516, 616 overlap when the first strap tie 510 engages the second strap tie 610, while the regions outside of the outer bodies 513, 613 are exteriors or outer regions). The outer bodies 513, 613 are disposed distal from the interior of the strap tie assembly 500.

In some embodiments, the first inner body 512 includes a first inner opening 518 for receiving the second strap 616, and the first outer body 513 includes a first outer opening 520 for receiving the second strap 616 once the second strap 616 has been received through the first inner opening 518. Similarly, the second inner body 612 includes a second inner opening 618 for receiving the first strap 516, and the second outer body 613 includes a second outer opening 620 for receiving the first strap 516 once the first strap 516 has been received through the second inner opening 618. As such, each strap tie may include a pair bodies. As shown in FIG. 11, the first outer body 513 is attached to the first inner body 512 proximate to the first proximal end 528 of the first strap 516; similarly, the second outer body 613 is attached to the second inner body 612 proximate to the second proximal end 628 of the second strap 616. As shown in FIG. 11, the inner openings 518, 618 have a depth (e.g., the length of a strap that passes through the opening) that is greater than the depth of the outer openings 520, 620. In various embodiments, various modifications may be made to the sizes of the openings (e.g., the depth of the outer openings 520, 620 may be greater than the depth of the inner openings 518, 618).

In some embodiments, the first inner body 512 and the second inner body 612 are provided as movable elements that allow for disengagement (e.g., loosening, decoupling, separating) of the first strap tie 510 from the second strap 616, and/or for disengagement of the second strap tie 610 from the first strap 516. For example, the inner bodies 512, 612 may include an engagement member (e.g., an engagement member similar to the engagement members provided for strap tie assemblies 100, 300), and the inner bodies 512, 612 may be provided as a button or other actuator such that actuation (e.g., squeezing, pushing, sliding, etc.) of the inner bodies 512, 612 disengages the engagement members from a corresponding movement restriction member (e.g. movement restriction members 526, 626). In some embodiments, the engagement members are flexible, such that they respond to actuation by the inner bodies 512, 612 by deforming or otherwise changing in shape, and thus may be disengaged from the movement restriction members 526, 626.

In some embodiments, the straps 516, 616 are oriented at an angle (e.g., a 90-degree angle, etc.) relative to the bases 514, 614. For example, as shown in FIGS. 10-11, when the first strap tie 510 and the second strap tie 610 are engaged, a transverse axis that passes through the straps 516, 616 in the interior region of the strap tie assembly 500 is parallel to a plane generally containing the bases 514, 614. In other words, when the strap tie assembly 500 is assembled (e.g., the first strap tie 510 and the second strap tie 610 are engaged) and secured to portions of skin on either side of a wound, the movement restrictions members 526, 626 of each strap 516, 616 will both tend to face in a direction that does not intersect with the portions of skin or the wound.

Figure 12:
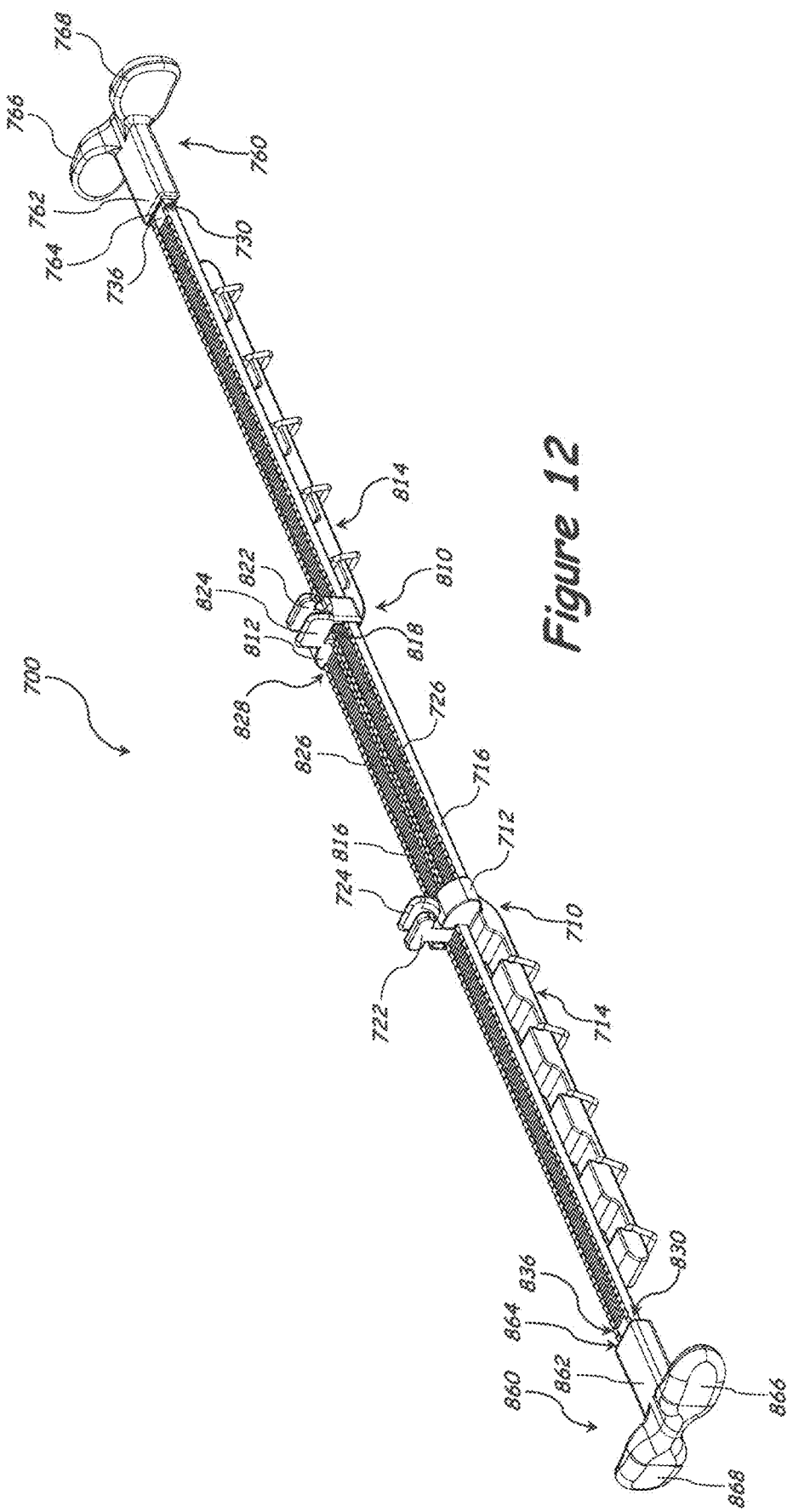
FIG. 12 is a perspective view of an embodiment of a strap tie assembly in which each strap tie includes an actuatable engagement member and a lobed handle.

Referring now to FIGS. 12-15, a strap tie assembly 700 is shown. The strap tie assembly is similar in structure and function to the strap tie assembly 500 shown in FIGS. 10-11. FIG. 12 is a perspective view of the strap tie assembly 700. The strap tie assembly includes a first strap tie 710 and a second strap tie 810. The first strap tie 710 includes a first body 712 that includes a single opening for receiving a second strap 816 of the second strap tie 810. Similarly, the second strap tie 810 includes a second body 812 that includes a single opening 818 for receiving a first strap 716 of the first strap tie 710. When the straps 716, 816 have been received by corresponding openings, the straps 716, 816 are disposed adjacent to and parallel to each other. A first base 714 extends from the first body 712, and similarly a second base 814 extends from the second body 812.

Figure 13:
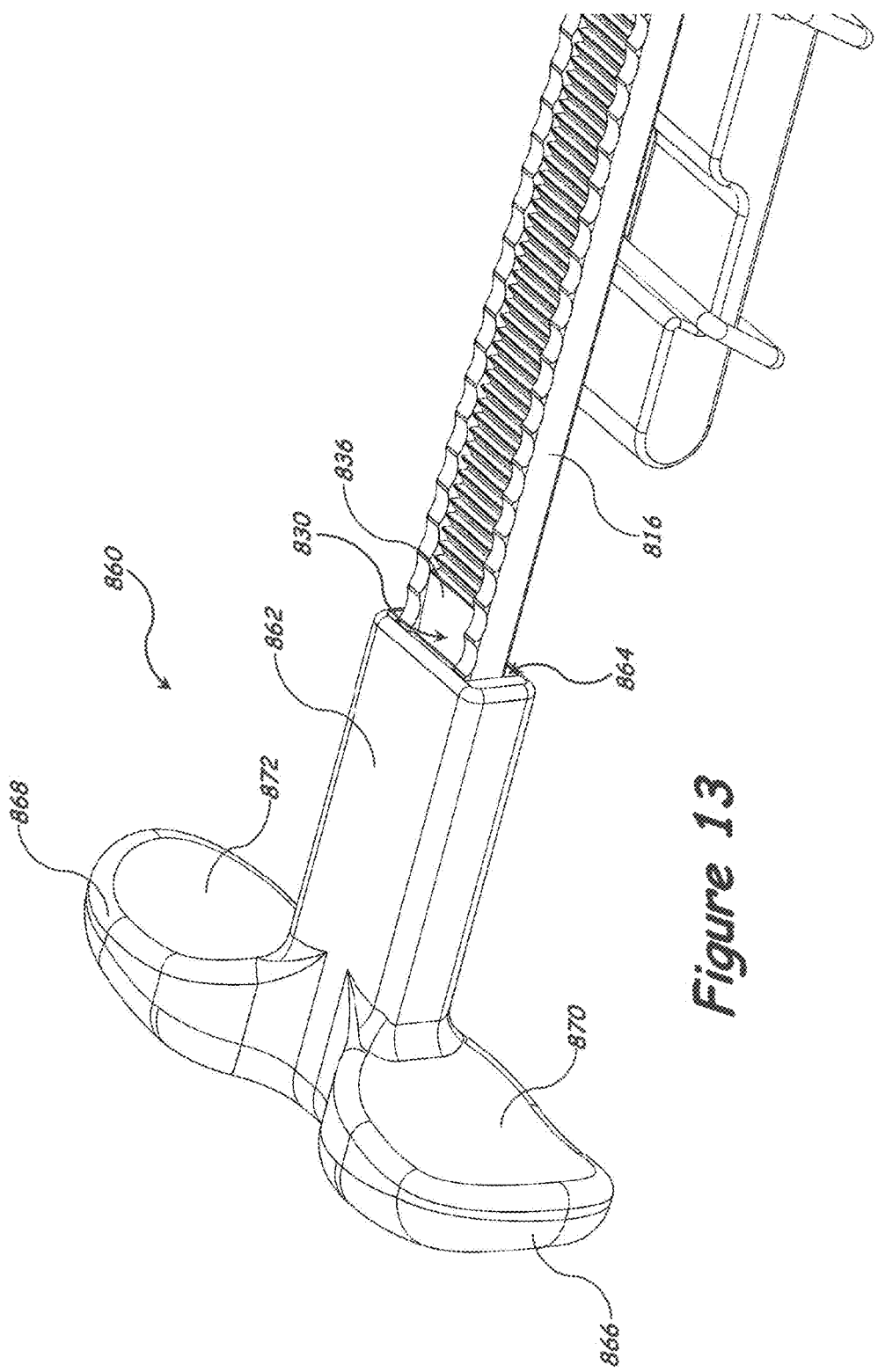
FIG. 13 is an end perspective view of an embodiment of the lobed handle of FIG. 12.

FIG. 13 shows a detail perspective view of a distal end 830 of the second strap 816. The distal end 830 has been provided with a second handle 860. As shown in FIG. 13, the second handle 860 is detachably coupled to a second strap handle 836 disposed at the distal end 830 of the second strap 816. The second handle 860 includes a second handle body 862 defining a second handle opening 864. The second handle opening 864 is configured to receive (e.g., detachably couple to, have inserted, engage) the second strap handle 836. In other words, the second handle 860 may be provided as a modular device to supplement the grip/handling provided by the second strap handle 836 of the second strap 816. The second handle 860 also includes a pair of handle lobes 866, 868 extending from an opposite end of the second handle body 862 from where the second handle opening 864 receives the second strap 816. In some embodiments, the handle lobes 866, 868 include lobe openings 870, 872, which may allow a user to further grip/handle the second handle 860 (e.g., to insert a finger through the lobe openings 870, 872, etc.). Referring back to FIG. 12, the distal end 730 of the first strap 716 may also be provided with a first handle 760 proximate to a first strap handle 736 of the first strap 716. The first handle 760 may be similar to or identical to the second handle 860. For example, the first handle 760 and the second handle 860 may be identical and interchangeable. As shown in FIG. 12, the first handle 760 includes a first handle body 762 for receiving the first strap 716 in a first handle opening 764, and a pair of first handle lobes 766, 768 extending from an opposite end of the first handle body 762 from where the first handle body 762 receives the first strap.

Figure 14:
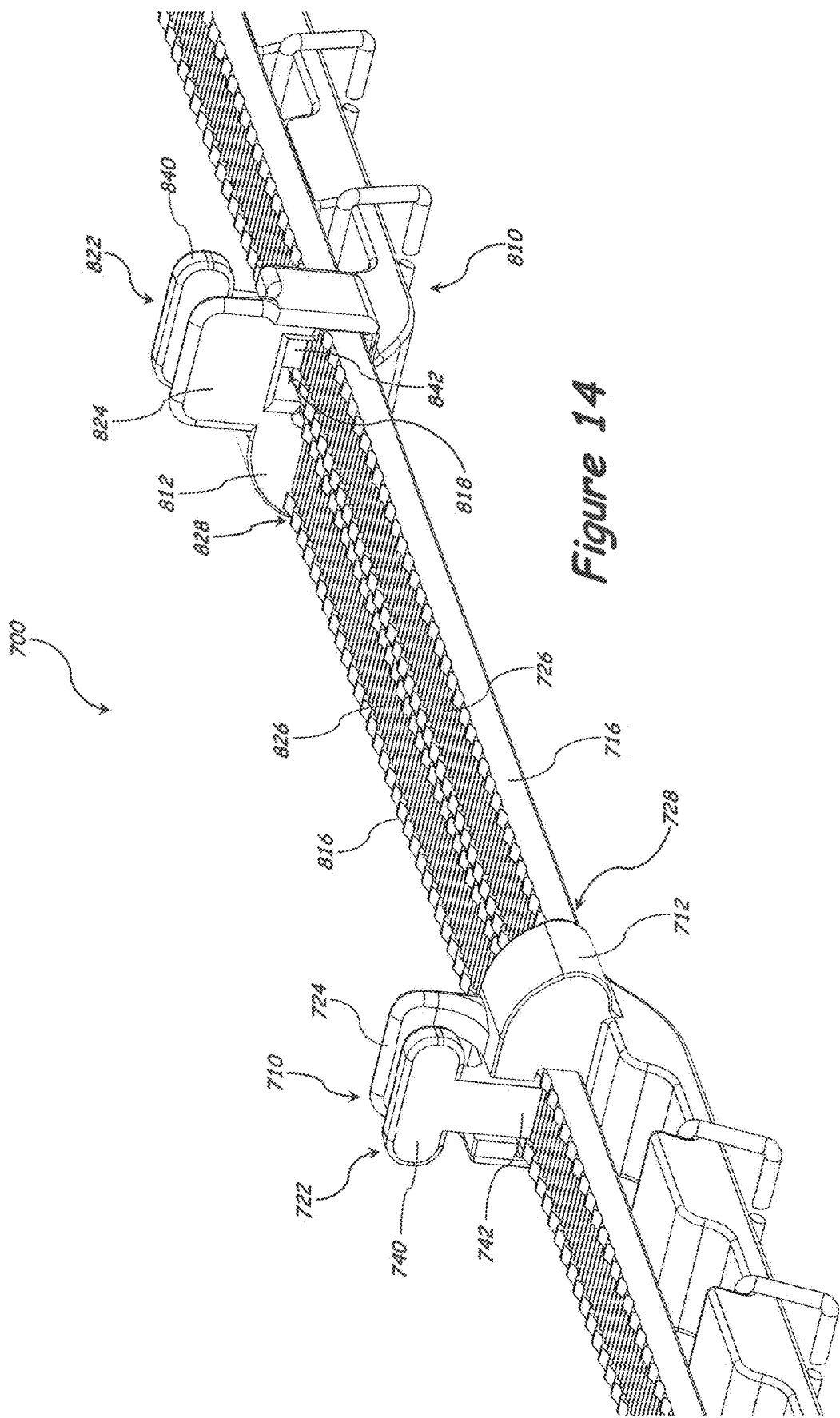
FIG. 14 is a detailed perspective view of an embodiment of the strap tie assembly of FIG. 12 illustrating the engagement between each strap tie of the strap tie assembly.
Figure 15:
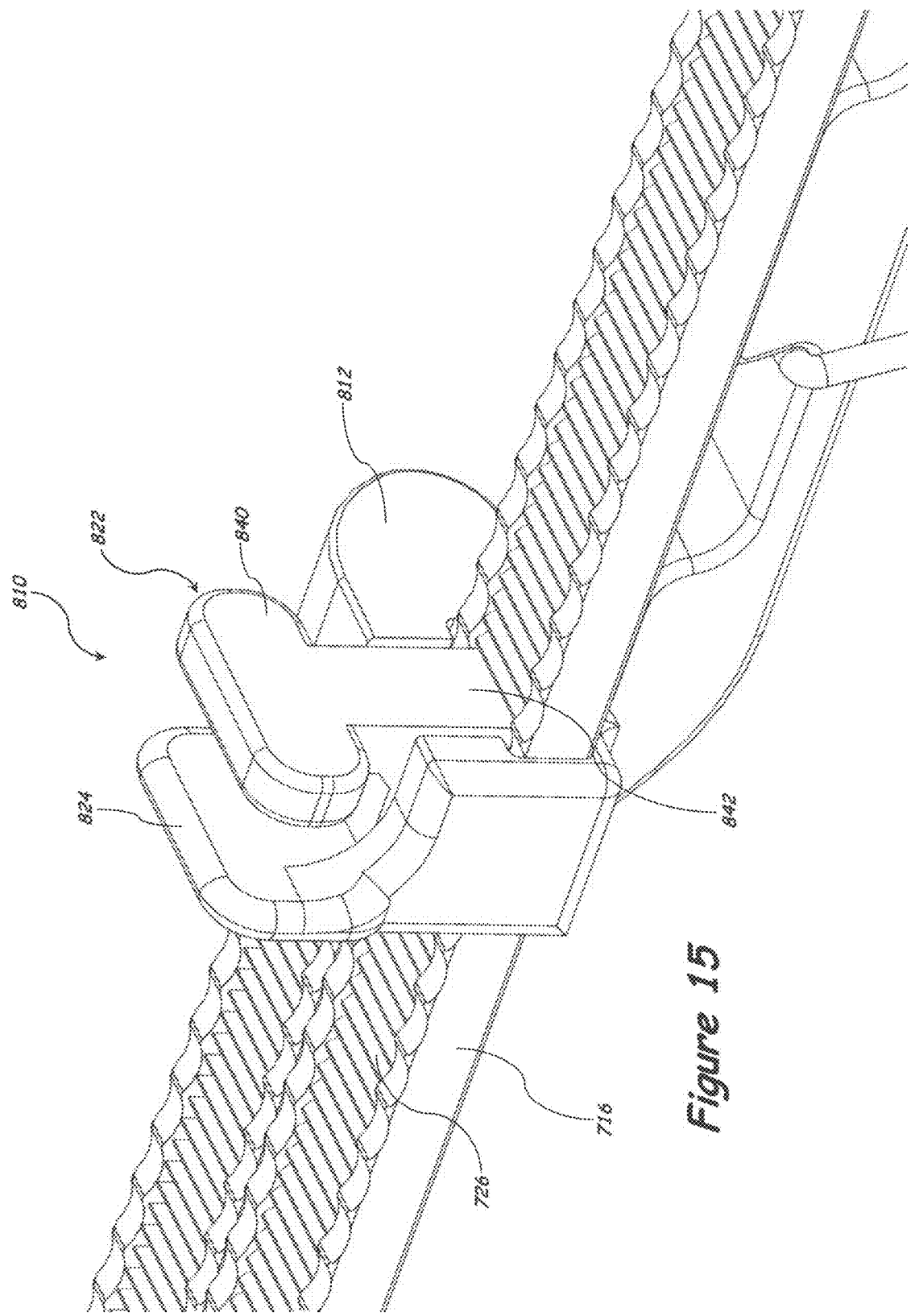
FIG. 15 is a detailed perspective view of an embodiment of the strap tie assembly of FIG. 12 in which an actuatable engagement member has engaged a strap of another strap tie.

Referring further to FIGS. 14-15, detail views of the first strap tie 710 and the second strap tie 810 are shown in order to illustrate the operation of the engagement mechanism between the strap bodies 712, 812 and the straps 716, 816. The first strap tie 710 includes a first engagement member 722. The first strap tie 710 also includes a first engagement base 724 extending from the first body 712. The first engagement base is disposed on an inward side of the first strap tie 710 (e.g., adjacent to the proximal end 728 of the first strap 716; etc.). The first engagement base 724 also includes an opening for receiving a strap from another strap tie. The first engagement member 722 includes a first engagement portion 742 for engaging a second movement restriction member 826 of the second strap 816, and a first actuator 740. The first actuator 740 may be manipulated (e.g., squeezed, translated, pushed, adjusted, etc.) in order to engage or disengage the first engagement portion 742 from the second movement restriction member 826. For example, as shown in FIGS. 14-15, the first actuator 740 may be squeezed towards the first engagement base 724 (e.g., substantially parallel to the direction that the second strap 816 passes through the opening of the first strap tie 710), in order to disengage the first engagement portion 742 from the second movement restriction member 826.

The second strap tie 810 may include a similar or identical engagement mechanism as provided for the first strap tie 710. For example, as shown in FIGS. 12, 14, and 15, the second strap tie 810 receives the first strap 716 through a second opening 818 of a second engagement base 824. A second engagement portion 842 of a second engagement member 822 is configured to engage a first movement restriction member 726 of the first strap 716. A second actuator 840 may be manipulated in order to engage or disengage the second engagement portion 842 from the first movement restriction member 726. The second engagement base 824 is disposed on an inward side of the second strap tie 810, such that the second opening 818 is disposed adjacent to the proximal end 828 of the second strap 816. The second engagement base 824 is provided continuous with a plane defined by the second opening 818, perpendicular to the direction through which the first strap 716 is received through the second opening 818. As such, when each strap tie 710, 810 has received a strap 716, 816 from the other strap tie, the straps 716, 816 are disposed adjacent and parallel to each other.

Referring now to FIGS. 16-19, a strap tie assembly 900 is shown. The strap tie assembly 900 is similar in structure and function to the strap tie assembly 700 shown in FIGS. 12-15. The engagement mechanism of the strap tie assembly 900 is similar to the engagement mechanism of the strap tie assembly 700. A first strap tie 910 includes a first strap body 912. The first strap body 912 includes a first engagement member 922 that can engage/disengage a second movement restriction member 1026 of a second strap 1016 of the second strap tie 1010, for example by squeezing the first engagement mechanism 922 towards a first engagement body 924. The first strap body 912 includes a first opening 918 disposed adjacent to a proximal end 928 of the first strap 916. The first engagement member 922 is disposed above (e.g., on an opposite side of the first strap body 912 from a first base 914 of the first strap body 912) the first opening 918, and can be actuated (e.g., squeezed) in a direction perpendicular to a direction that a second strap 1016 may be received through the first opening 918.

Figure 16:
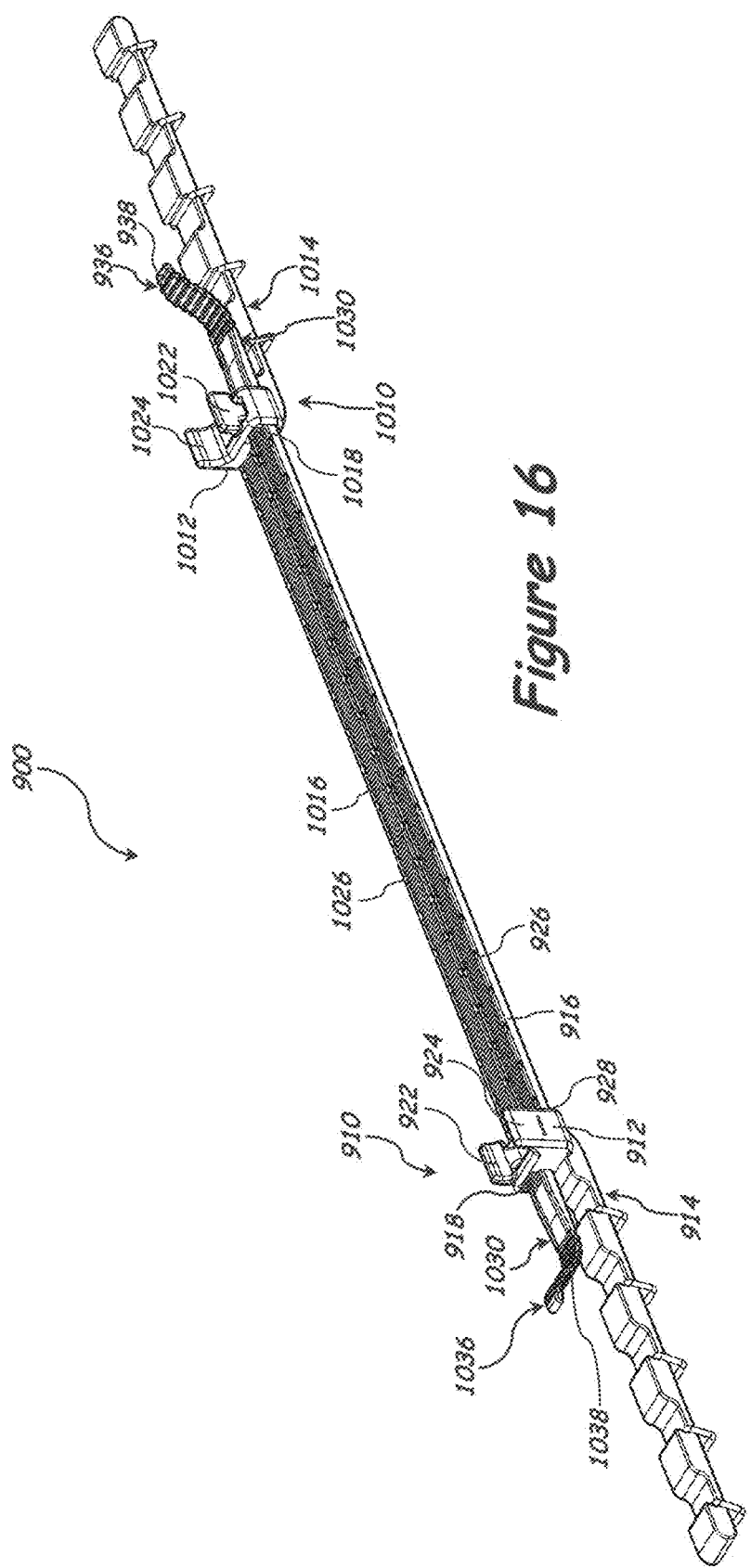
FIG. 16 is a perspective view of an embodiment of a strap tie assembly in which each strap includes a handle end with protrusions/indentations.
Figure 19:
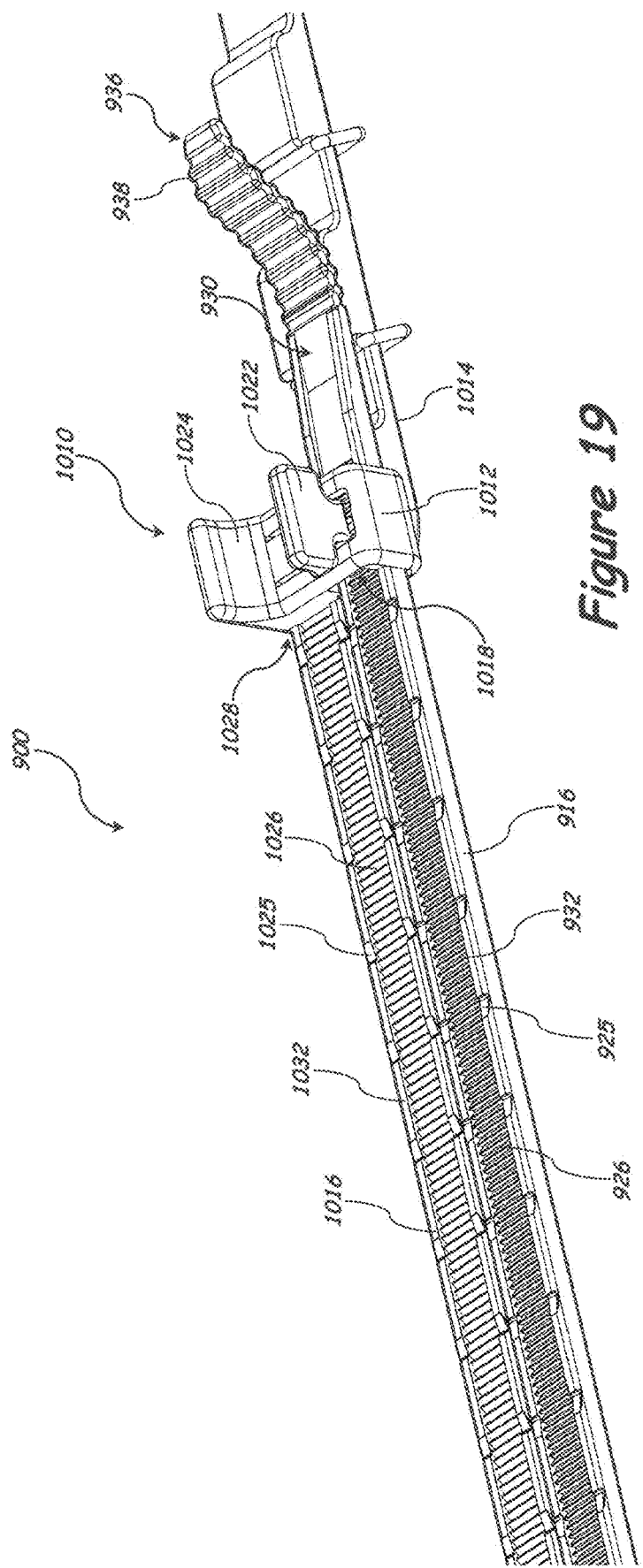
FIG. 19 is a detailed top perspective view of an embodiment of the strap tie assembly of FIG. 16 in the vicinity of a strap tie illustrating various features of the strap ties and the engagement between the strap ties.

The second strap tie 1010 may be similar or identical to the first strap tie 910. As shown in FIGS. 16 and 19, the second strap tie 1010 includes a second strap body 1012. The second strap body 1012 includes a second engagement member 1022 that can engage/disengage a first movement restriction member 926 of the first strap 916, for example by squeezing the second engagement member 1022 towards a second engagement body 1024. The second strap body 1012 includes a second opening 1018 disposed adjacent to a proximal end 1028 of the second strap 1016. The second engagement member 1022 is disposed above (e.g., on an opposite side of the second strap body 1012 from a second base 1014 of the second strap body 1012) the second opening 1018, and can be actuated)(e.g., squeezed) in a direction perpendicular to a direction that the first strap 916 may be received through the second opening 1018.

Referring further to FIGS. 16-19, the strap ties 910, 1010 include handles 936, 1036 extending from respective distal ends 930, 1030 of the strap ties 910, 1010. The handles 936, 1036 are provided with handle protrusions 938, 1038, to facilitate gripping of the handles 936, 1036 by a user. The handles 936, 1036 curve away from the bases 914, 1014 of the respective strap ties 910, 1010. Protrusions such as handle protrusions 938, 1038 provide indentations in between the handle protrusions 938, 1038.

Figure 17:
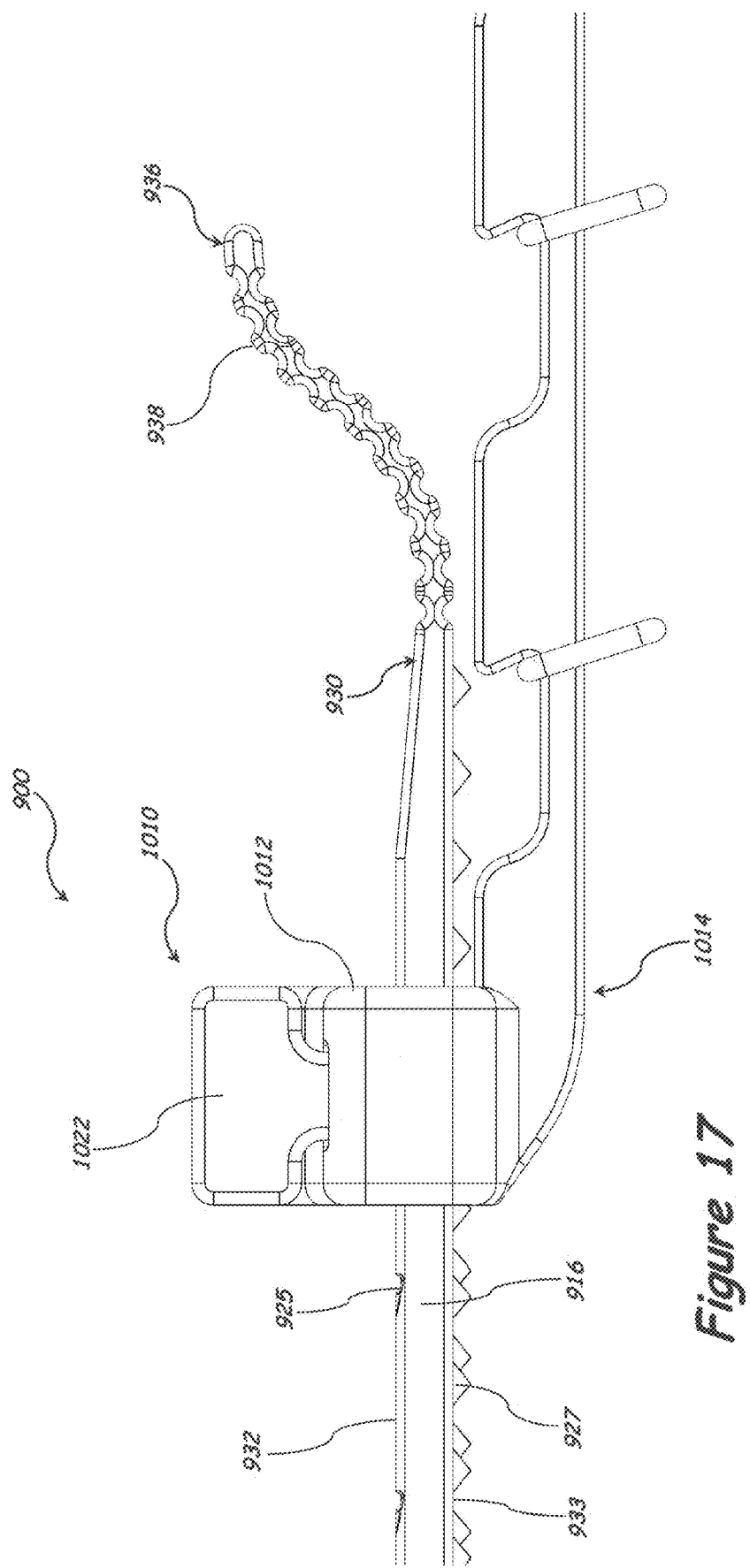
FIG. 17 is a detailed side view of an embodiment of a strap tie of the strap tie assembly of FIG. 16 illustrating various features of the straps.

Referring further to FIG. 17, a side detail view of the strap tie assembly 900 in the region of the second strap body 1012 is shown to illustrate particular features of the engagement mechanism and the handle 936. An upper surface 932 (e.g., a surface which is disposed on an opposite side of the first strap 916 from a portion of skin/a wound; a surface which is disposed on an opposite side of the first strap 916 from the second base 1014, etc.) of the first strap 916 includes first edge cavities 925. As shown in FIG. 17, the first edge cavities 925 include a biased shape, such that the first edge cavities 925 include a greater gradient towards the distal end 930 of the first strap 916. The first edge cavities 925 may act in a similar manner to an engagement mechanism such as an engagement member, in order to selectively or consistently prevent translation of the first strap tie 910 away from the second strap tie 1010. When the first edge cavities 925 include a biased shape, the first edge cavities 925 may be configured to engage a pawl in order to prevent translation of the first strap tie 910 away from the second strap tie 1010. In some embodiments, the first edge cavities 925 provide resistance to slipping, such as slipping that might occur between the first strap 916 and the hand(s) of a user when gripping the first strap 916, such as when the first strap 916 is covered in blood, lipids, or other fluids. As shown in FIG. 19, the second strap 1016 may also include an upper surface 1032 including second edge cavities 1025, which may be similar to or identical to the first edge cavities 925. For example, the second edge cavities 1025 may also include a biased shape, such that when each of the straps 916, 1016 have been received by an opposing strap tie 1010, 910, the straps 916 are aligned parallel to and adjacent to one another, and the first edge cavities 925 and second edge cavities 1025 have an opposing orientation.

Referring back to FIG. 17, the first strap 916 may also include a lower surface 933 (e.g., a surface which is disposed on a side of the first strap 916 proximate to a portion of skin/a wound; a surface which is disposed on a side of the first strap proximate to the second base 1014; etc.), and the lower surface 933 may include first protrusions 927.

Figure 18:
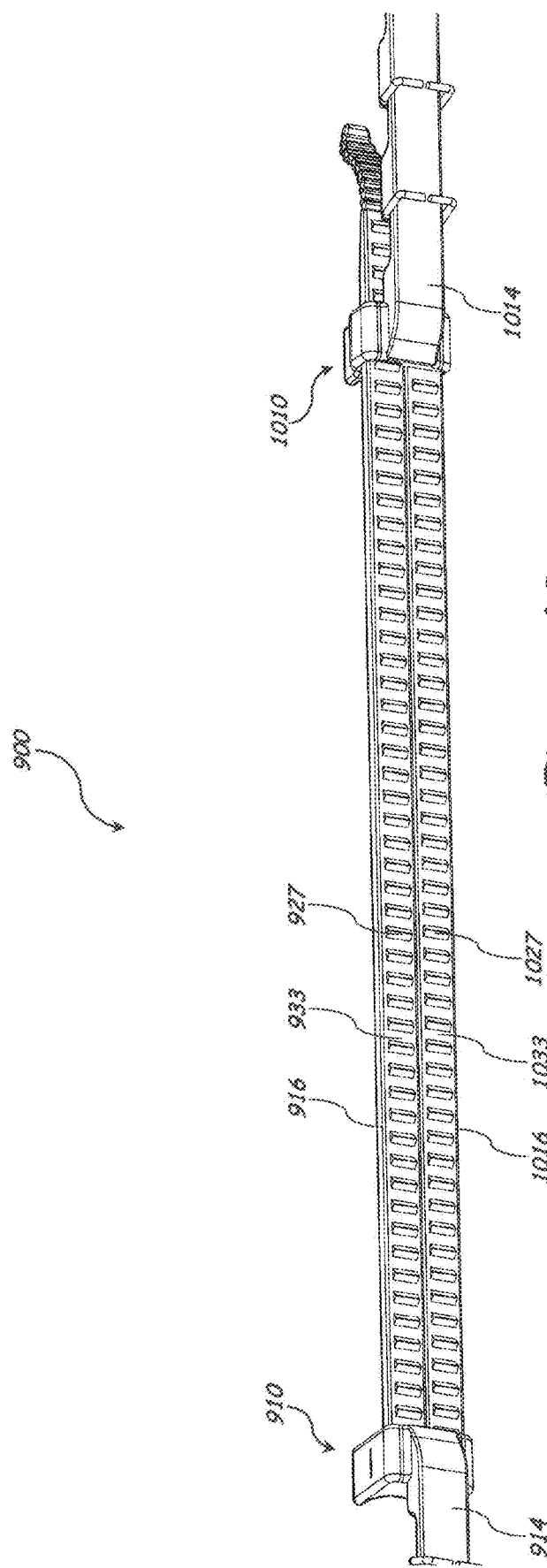
FIG. 18 is a bottom perspective view of an embodiment of the strap tie assembly of FIG. 16 illustrating various features of the straps.

Referring now to FIG. 18, a perspective view is shown of a bottom or lower side of the strap tie assembly 900 (e.g., the side of the strap tie assembly 900 to be disposed proximate to a portion of skin/a wound, etc.). FIG. 18 illustrates the first protrusions 927 disposed along the lower surface 933 of the first strap 916, and the second protrusions 1027 disposed along the lower surface 1033 of the second strap 1016. The second protrusions 1027 may be similar or identical to the first protrusions 927. For example, as shown in FIG. 18, the protrusions 927, 1027 have similar spacing along the respective lower surfaces 933, 1033, and include similar shapes provided by two equal and opposite angled edges. In various embodiments, the protrusions 927, 1027 may include various shapes, such as shapes biased towards one side, rectangular solids, trapezoidal solids, curved or elongated solids, etc. As shown in FIGS. 17 and 18, the protrusions 927, 1027 extend a distance away from respective surfaces 933, 1033 such that the protrusions 927, 1027 will not contact a wound or a portion of skin when at least one of the bases 914, 1014 contacts a wound or a portion of skin. In some embodiments, the protrusions 927, 1027 extend a distance away from respective surfaces 933, 1033 such that the protrusions 927, 1027 are configured to engage openings with the corresponding opposing strap bodies 1012, 912. In some embodiments, the protrusions 927, 1027 provide resistance to slipping, such as slipping that may occur between straps 916, 1016 and the hand(s) of a user when gripping the straps 916, 1016, such as when the straps 916, 1016 are covered in blood, lipids, or other fluids.

Referring further to FIG. 19, a detail perspective view of the strap tie assembly 900 proximate to the second strap tie 1010 is shown to illustrate features of the engagement mechanisms of the strap tie assembly 900. The second strap 1016 includes the second movement restriction members 1026 and the second edge cavities 1025 as being biased towards the "right" based on the orientation shown (e.g., the second strap 1016 extends in a first direction away from the second strap body 1012, and the second movement restriction members 1026 are biased in a second direction opposite to the first direction). Similarly, because the first strap 916 is disposed parallel and adjacent to the second strap 1016 while extending in an opposite direction as the second strap 1016 (e.g., extending from the first strap body 910 shown in FIG. 16, etc.), the first movement restriction members 926 and the first edge cavities 925 are biased towards the "left" based on the orientation shown. The biased orientation (e.g., disposed at an angle relative to a plane defined by a respective strap 916, 1016, etc.) of the movement restriction members 926, 1026 facilitates preventing translation of a strap away from an engagement member. For example, when the first strap 916 has been received through the second opening 1018, the engagement between the second engagement member 1022 and the first movement restriction members 926 allows the first strap 916 to be drawn towards the "right" so that a distance between the second strap tie 1010 and a first strap tie (e.g., first strap tie 910 shown in FIG. 16, etc.) decreases, while preventing translation of the first strap 916 in a manner in which a distance between the second strap tie 1010 and the first strap tie 910 would increase. This one-directional engagement and translation mechanism may also apply to the interaction between the second strap 1016 and the first strap tie 910, and between the edge cavities 925, 1025 and corresponding opposing strap ties 1010, 910.

As shown in FIG. 19, the second engagement member 1022 may be manipulated (e.g., adjusted, pushed, squeezed, etc.) by being translated towards the second engagement base 1024. When the second engagement member 1022 is manipulated, the second engagement member 1022 no longer engages a first movement restriction member 926 of the first strap 916, such that the first strap 916 may be translated both in a first direction "towards" the second strap tie 1010 such that a distance between the first strap tie 910 and the second strap tie 1010 decreases, and a second direction "away" from the second strap tie 1010 such that a distance between the first strap tie 910 and the second strap tie 1010 increases. In some embodiments, the biasing of the edge cavities 925, 1025 is great enough to aid in preventing translation of the strap ties 910, 1010 away from each other, but such biasing is not sufficient to independently prevent translation of the strap ties 910, 1010 away from each other when one or both of the engagement members 922, 1022 have been disengaged from corresponding movement restriction members 1026, 926. In some embodiments, the edge cavities 925, 1025 provide resistance to slipping, such as slipping that may occur between the straps 916, 1016 and the hand(s) of a user when gripping the straps 916, 1016, such as when the straps 916, 1016 are covered in blood, lipids, or other fluids.

Figure 20:
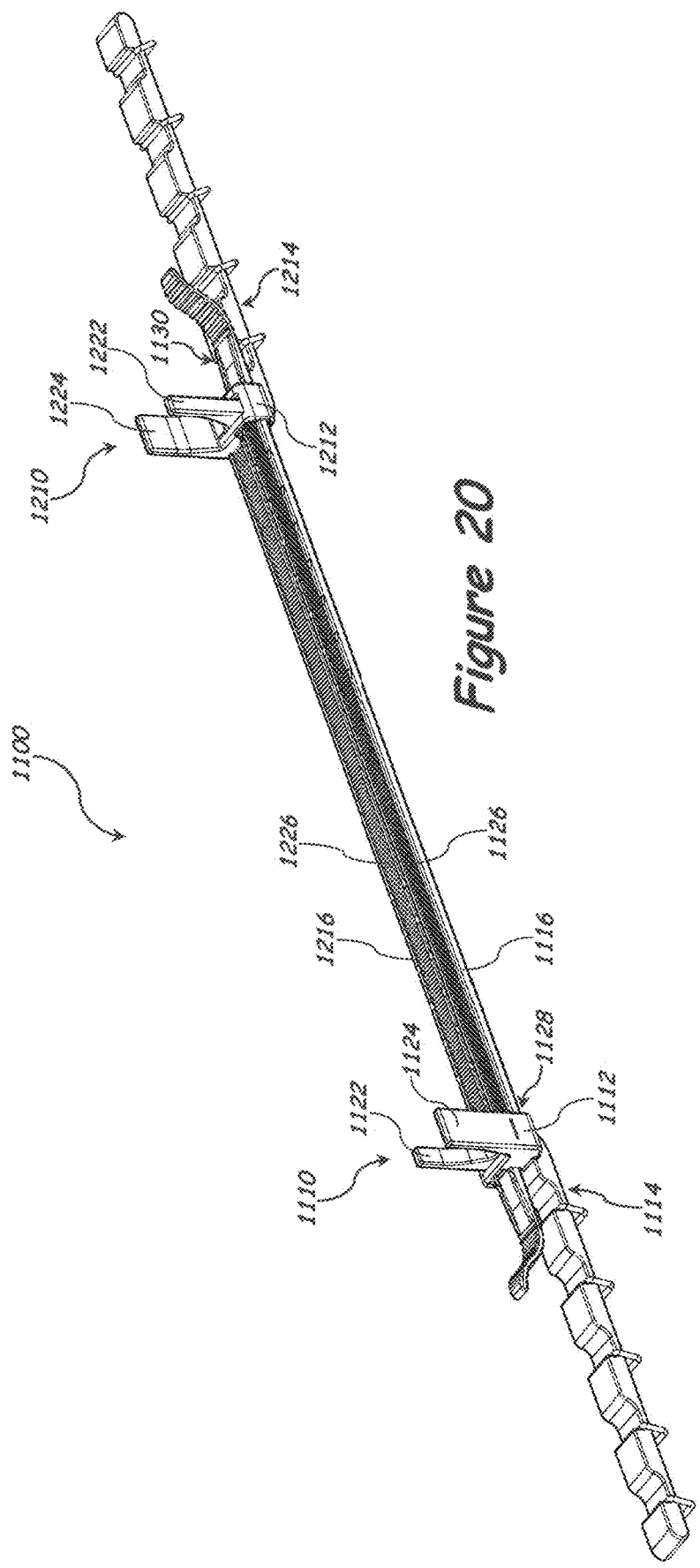
FIG. 20 is a perspective view of an embodiment of a strap tie assembly in which each strap tie body includes an elongated engagement member.
Figure 21:
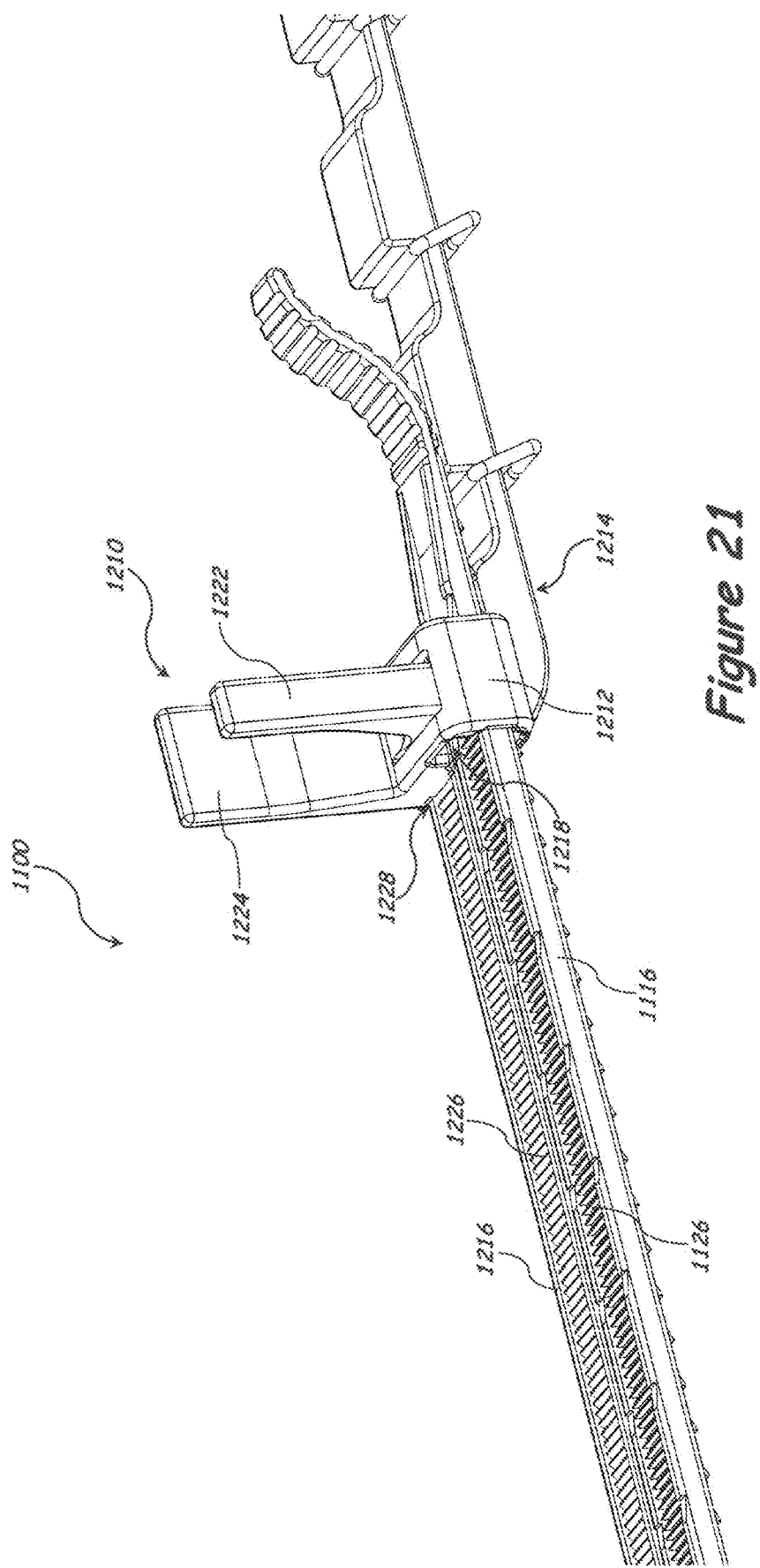
FIG. 21 is a detailed perspective view of an embodiment of a strap tie of the strap tie assembly of FIG. 20.
Figure 22:
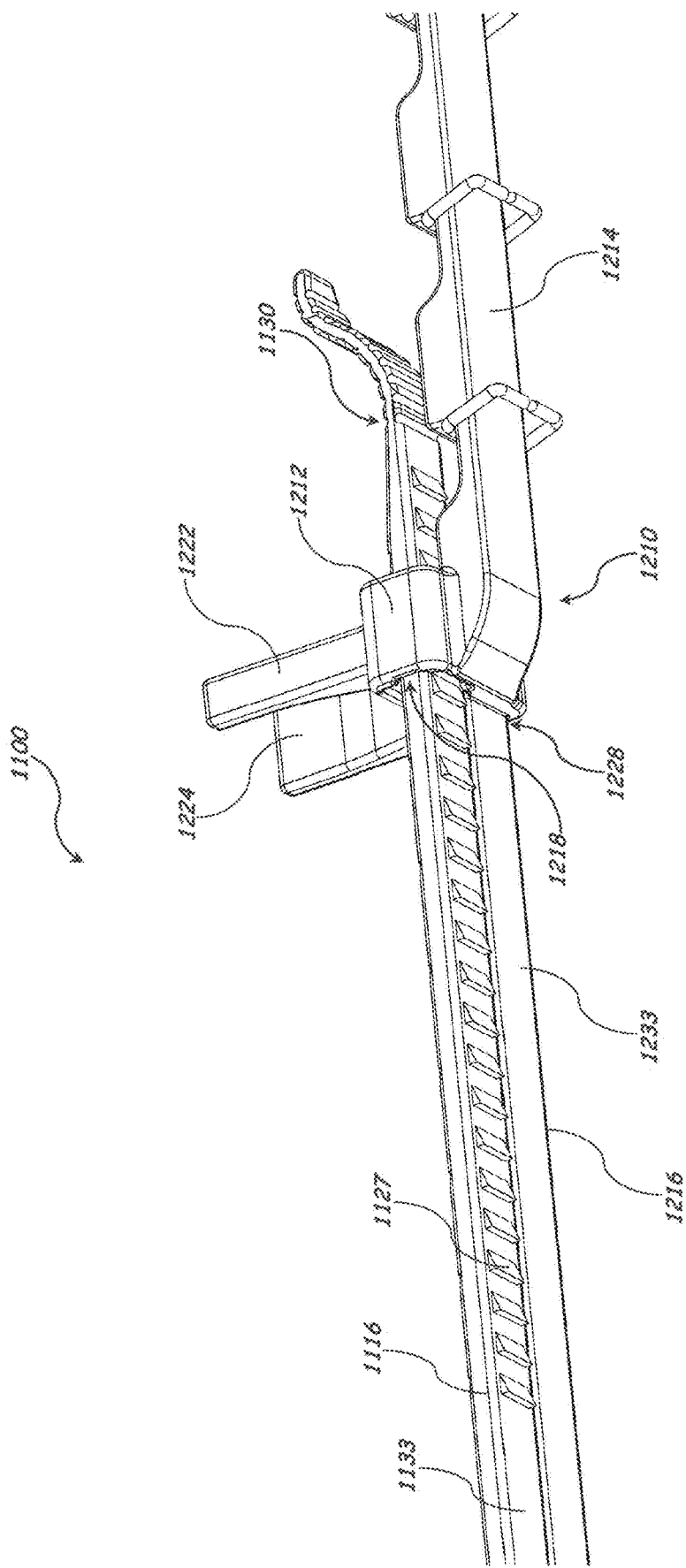
FIG. 22 is a detailed bottom perspective view of an embodiment of the strap tie assembly of FIG. 20 illustrating various features of the engagement mechanism and straps of the strap tie assembly.

Referring now to FIGS. 20-22, a strap tie assembly 1100 is shown. The strap tie assembly 1100 is similar in structure and function to the strap tie assembly 900. FIG. 20 is a perspective view of the strap tie assembly 1100. The strap tie assembly 1100 includes a first strap tie 1110 and a second strap tie 1210. The first strap tie 1110 includes a first strap body 1112, a first base 1114 extending from the first strap body 1112, a first strap 1116 extending from the first strap body 1112, and an engagement mechanism for engaging a strap from another strap tie including a first engagement member 1122 and a first engagement base 1124. First movement restriction members 1126 are provided along the first strap 1116. Similarly, the second strap tie 1210 includes a second strap body 1212, a second base 1214 extending from the second strap body 1212, a second strap 1216 extending from the second strap body 1212, and an engagement mechanism for engaging a strap from another strap tie including a second engagement member 1222 and a second engagement base 1224. Each of the straps 1116, 1216 includes respective movement restriction members 1126, 1226.

Referring further to FIG. 21, a detail perspective view of the second strap tie 1210 is shown to illustrate the engagement mechanism of the second strap tie 1210, such as when a first strap 1116 is received in a second opening 1218 of the second strap tie 1210. The second engagement member 1222 is similar to the second engagement member 1022 shown in FIGS. 16-19, and the second engagement base 1224 is similar to the second engagement base 1024 shown in FIGS. 16-19. The second engagement member 1222 and the second engagement base 1224 each extend a further distance away (e.g., in a direction away from where the strap tie assembly 1100 would be disposed along a portion of skin or along a wound) from the second strap body 1212 than the similar second engagement member 1022 and second engagement base 1024.

Referring further to FIG. 22, a detail perspective view is shown of a bottom or lower side of the strap tie assembly 1100 (e.g., a side of the strap tie assembly 1100 proximate to where the second base 1214 may be disposed adjacent to a portion of skin or a wound, etc.) in the vicinity of the second strap body 1212. The first strap 1116 includes protrusions 1127 disposed along a lower surface 1133 of the first strap 1116. As compared to the protrusions 927 of the first strap 916 shown in FIGS. 16-19, the protrusions 1127 of the first strap 1116 are provided only along a distal region of the lower surface 1133 (e.g., a region of the lower surface 1133 running only partially from the distal end 1130 towards a proximal end 1128 as shown in FIG. 20). For example, as shown in FIG. 22, the region of the lower surface 1233 of the second strap 1216 (which may be similar or identical to the first strap 1116) that is proximate to the proximal end 1228 does not include protrusions. As such, protrusions may be selectively provided such that they would not be disposed directly above a wound when the strap tie assembly 1100 is attached to portions of skin adjacent to the wound. In various embodiments, various numbers and groupings of protrusions may be provided along lower surfaces of straps of the strap tie assembly 1100 based on whether the protrusions would be disposed above a wound, how tightly the strap tie assembly 1100 is expected to be drawn together, how often the strap tie assembly 1100 is expected to be adjusted, etc. As shown in FIG. 22, the protrusions 1127 are biased towards the "left" based on the orientation shown in the figure (e.g., the protrusions 1127 extend further away from the lower surface 1133 on a side of the protrusions 1127 that is closer to the proximal end 1128 than the distal end 1130, etc.). Providing the protrusions 1127 with a such a bias may facilitate manipulation of the strap tie assembly 1100 in which the engagement between the second strap tie 1210 and the first strap 1116 prevents translation of the first strap tie (see, e.g., first strap tie 1110 shown in FIG. 20) away from the second strap tie 1210. In various embodiments, various biases may be provided to protrusions such as the protrusions 1127 in order to select the resistance that the protrusions 1127 provide against translation of the first strap 1116 in a certain direction.

Figure 23:
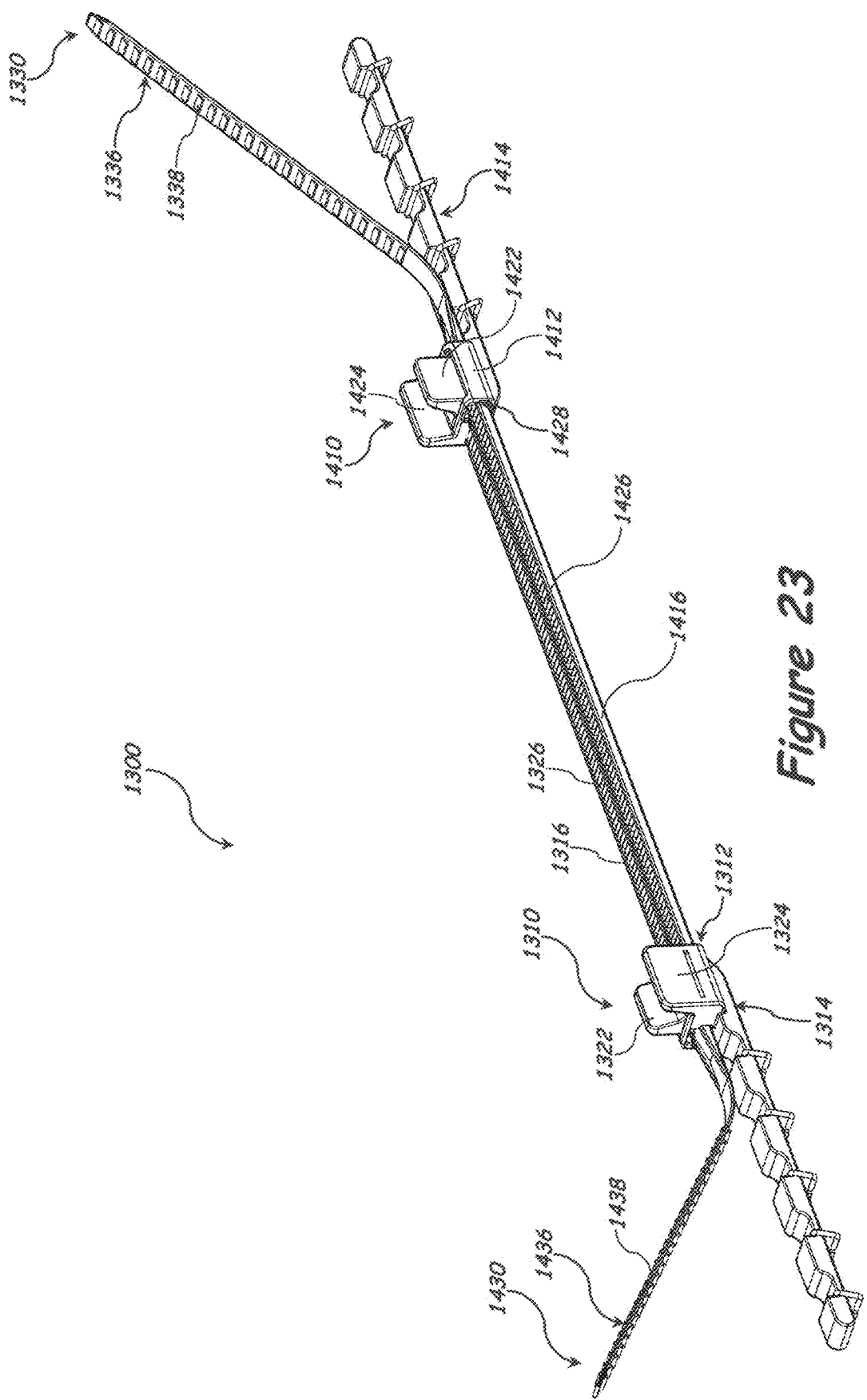
FIG. 23 is a perspective view of an embodiment of a strap tie assembly in which each of the straps includes an elongated handle region.
Figure 24:
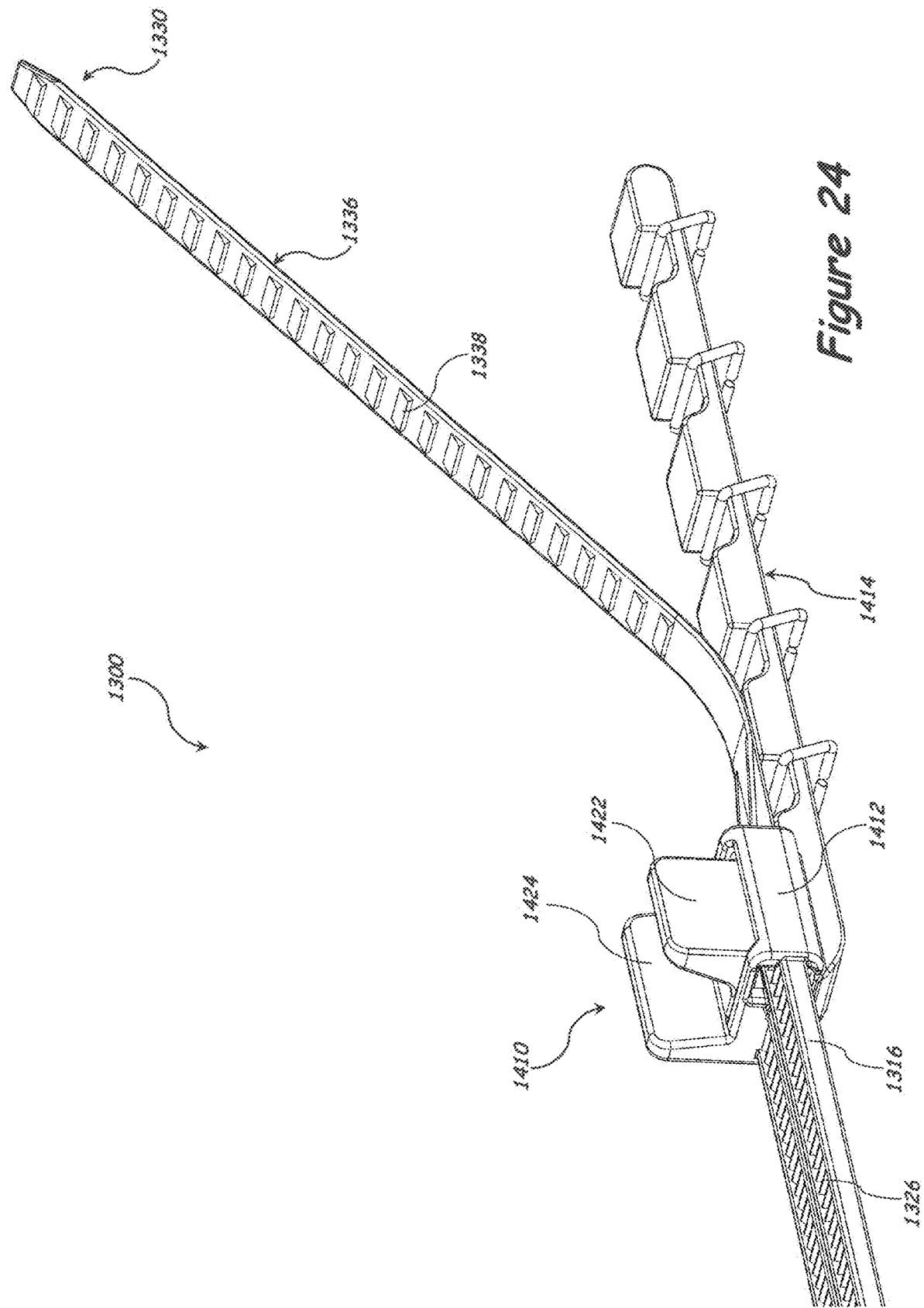
FIG. 24 is a detailed perspective view of an embodiment of a strap tie of the strap tie assembly of FIG. 23 illustrating features of the strap tie.
Figure 25:
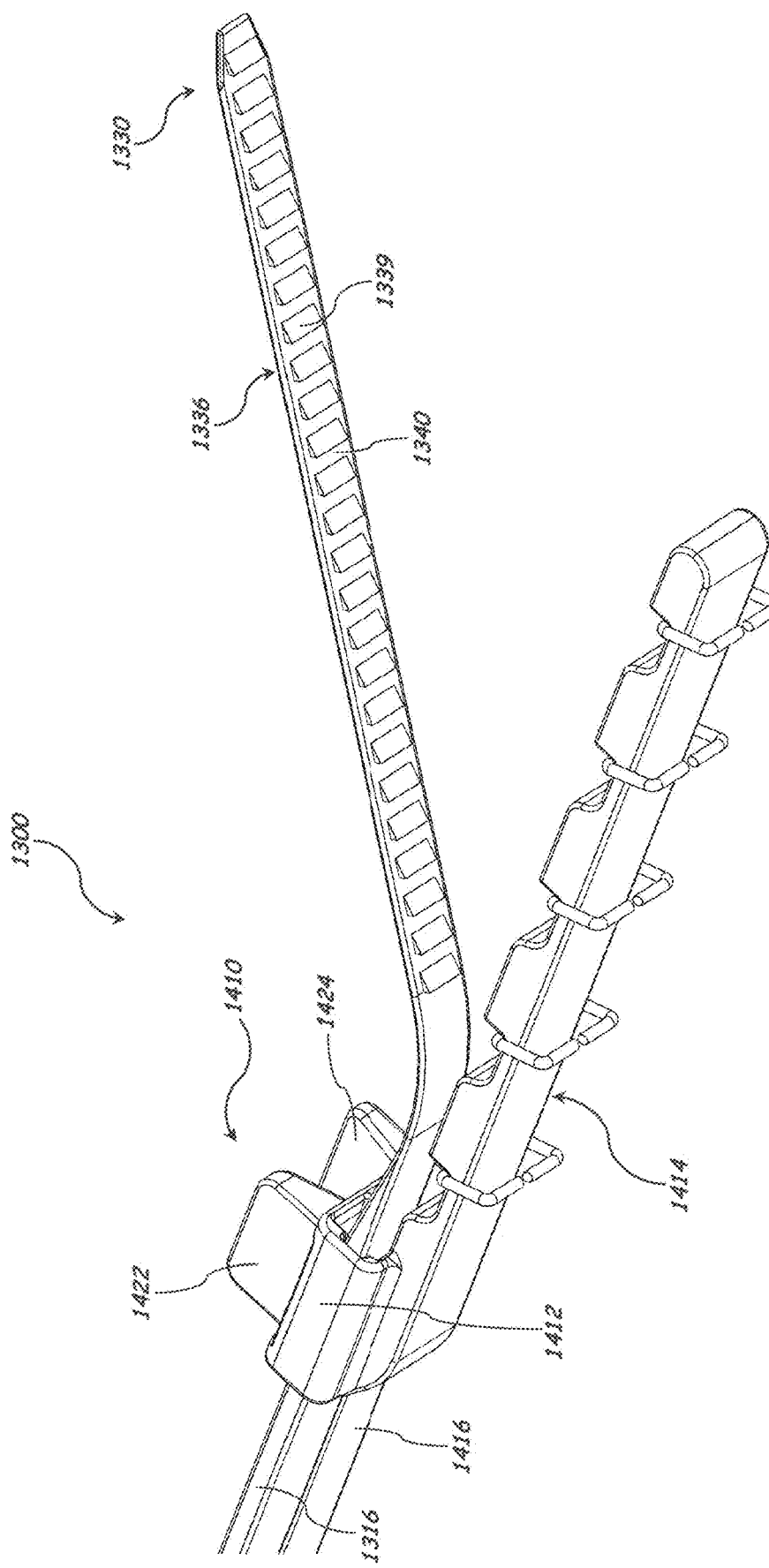
FIG. 25 is a detailed bottom perspective view an embodiment of a strap tie of the strap tie assembly of FIG. 23 illustrating features of the strap tie.
Figure 26:
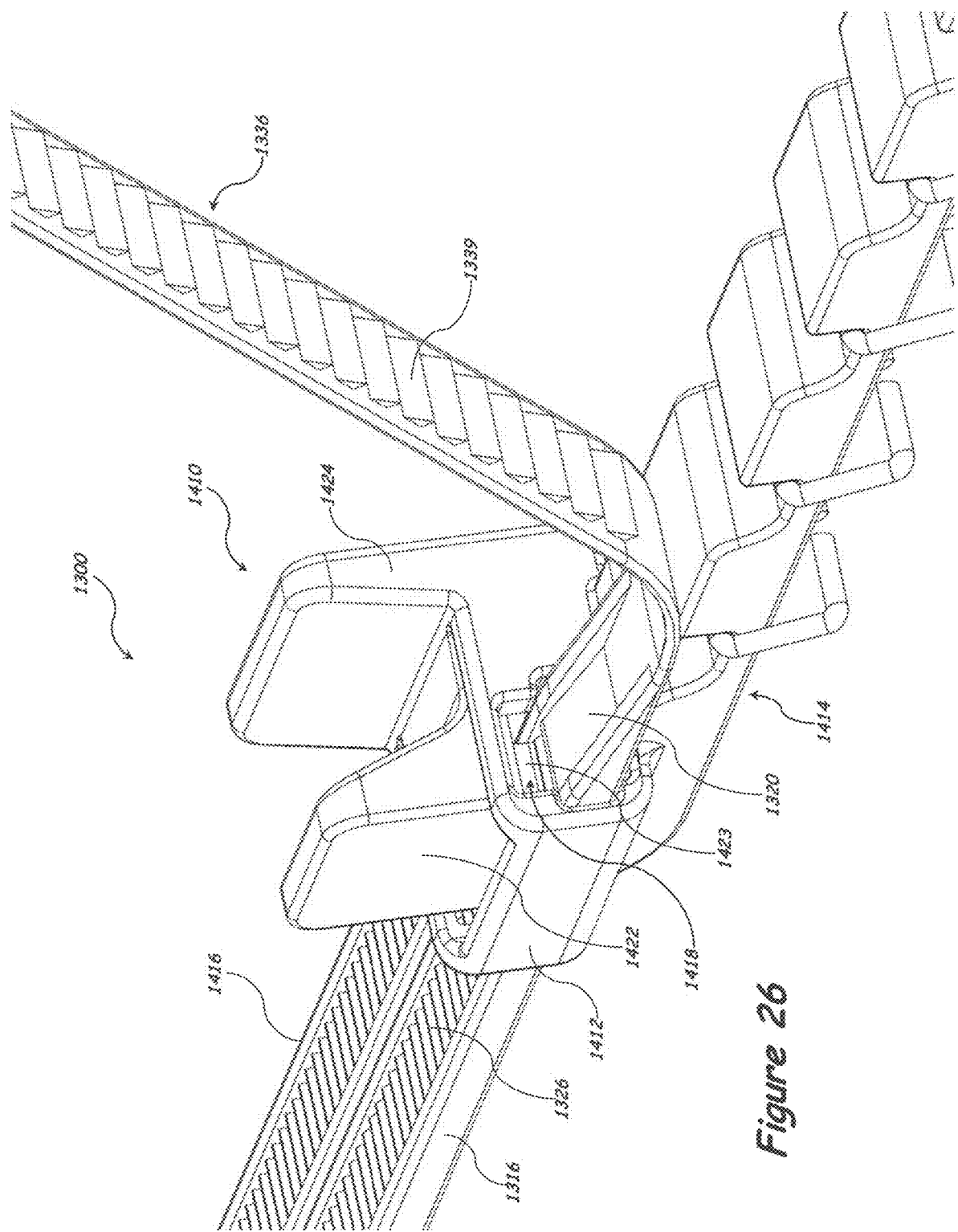
FIG. 26 is a detailed perspective view of an embodiment of a strap tie of the strap tie assembly of FIG. 23 illustrating features of the engagement mechanism and the elongated handle region.
Figure 27:
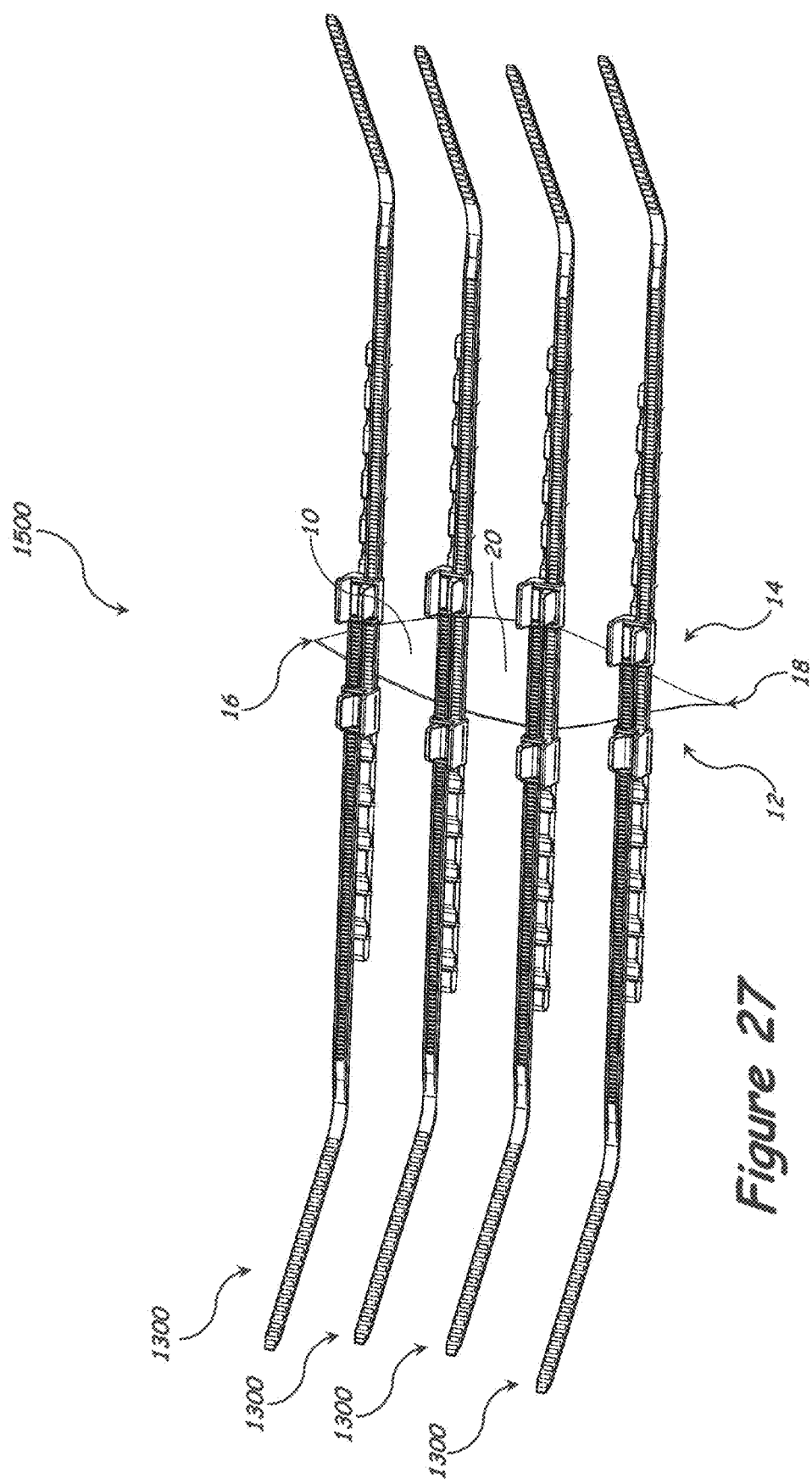
FIG. 27 is a perspective view of an embodiment of a grouping of multiple strap tie assemblies.
Figure 28:
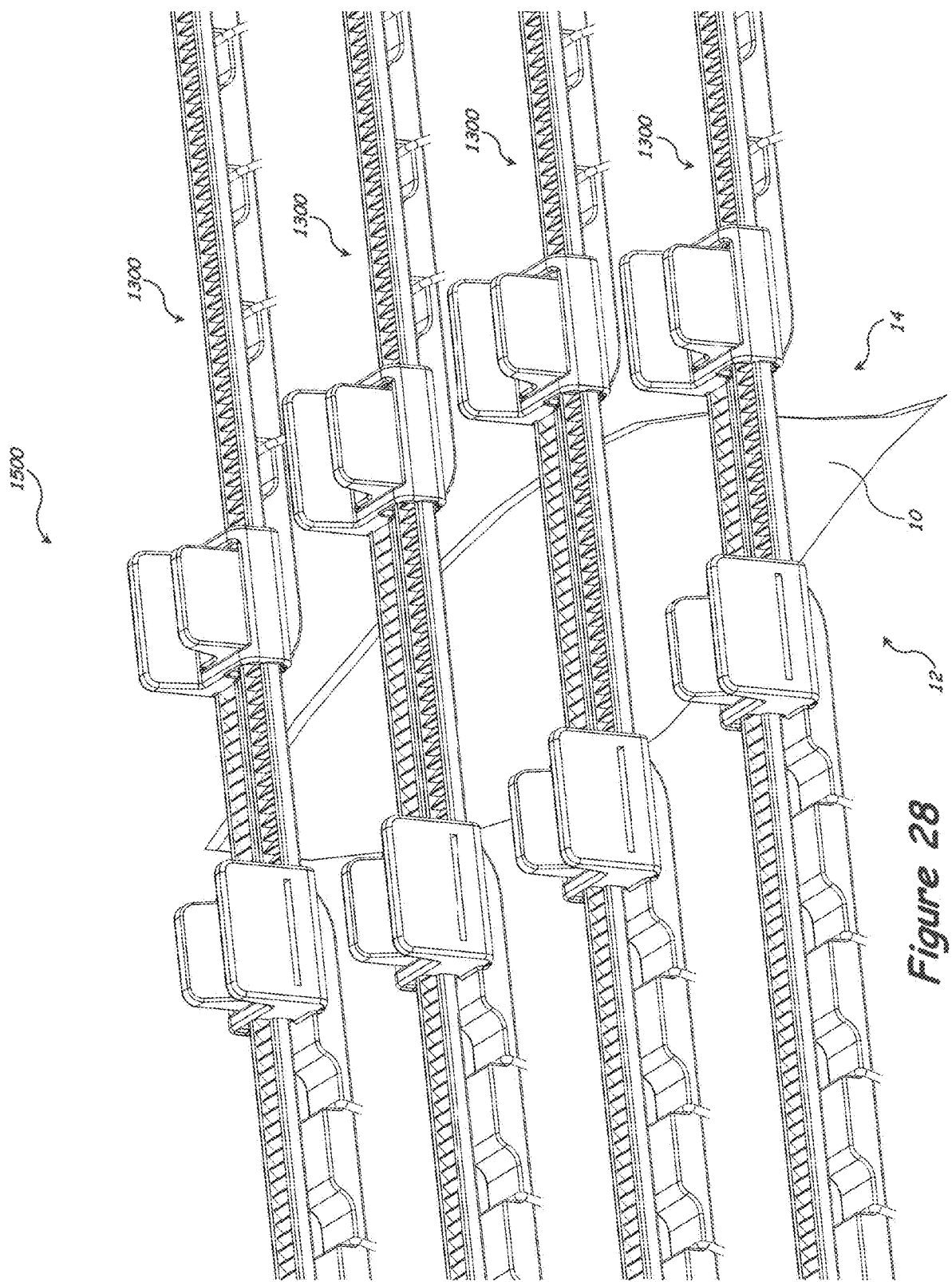
FIG. 28 is a detailed perspective view of an embodiment of the strap ties of the grouping of FIG. 27.
Figure 29:
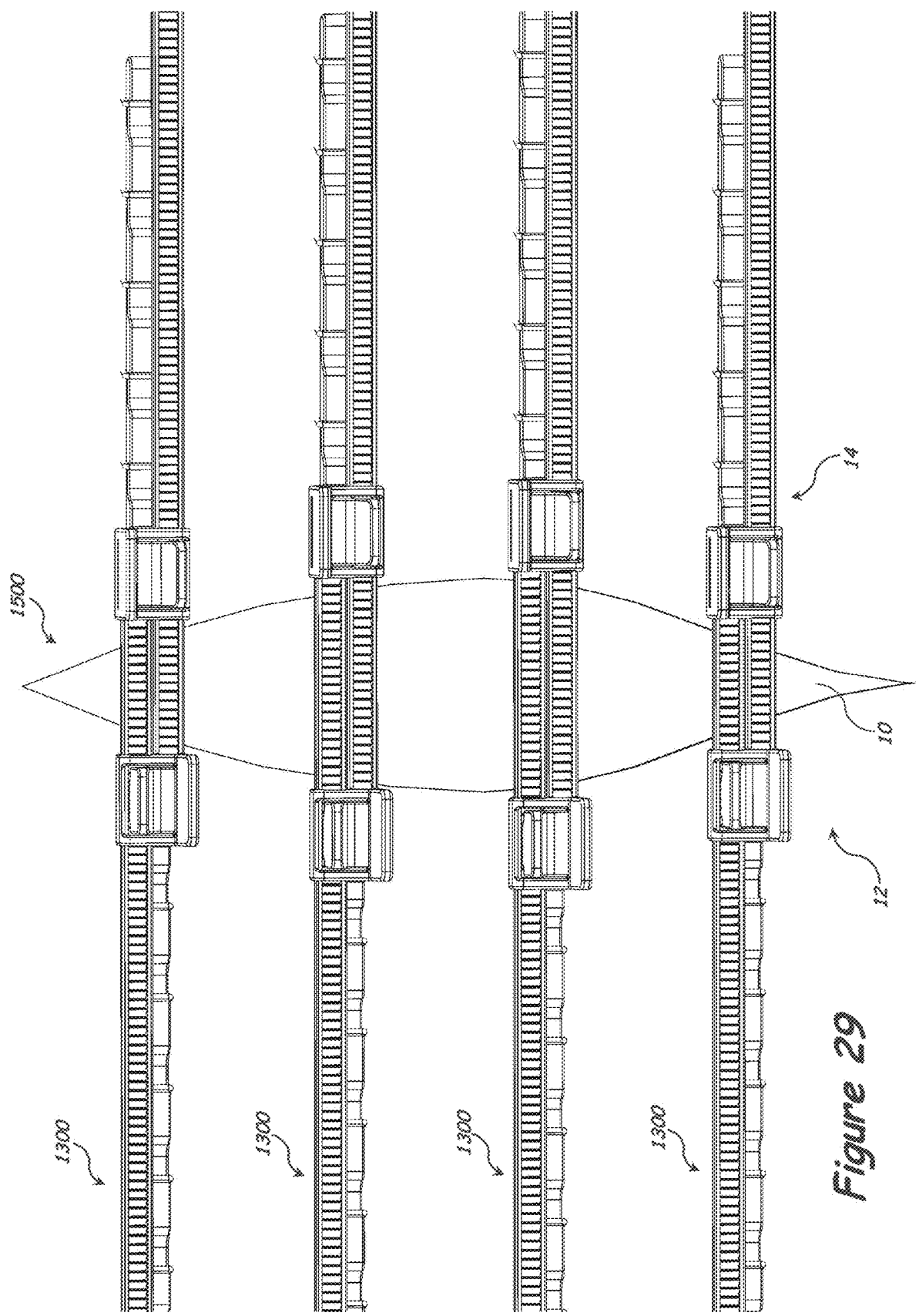
FIG. 29 is a top view of an embodiment of the grouping of FIG. 27.
Figure 30:
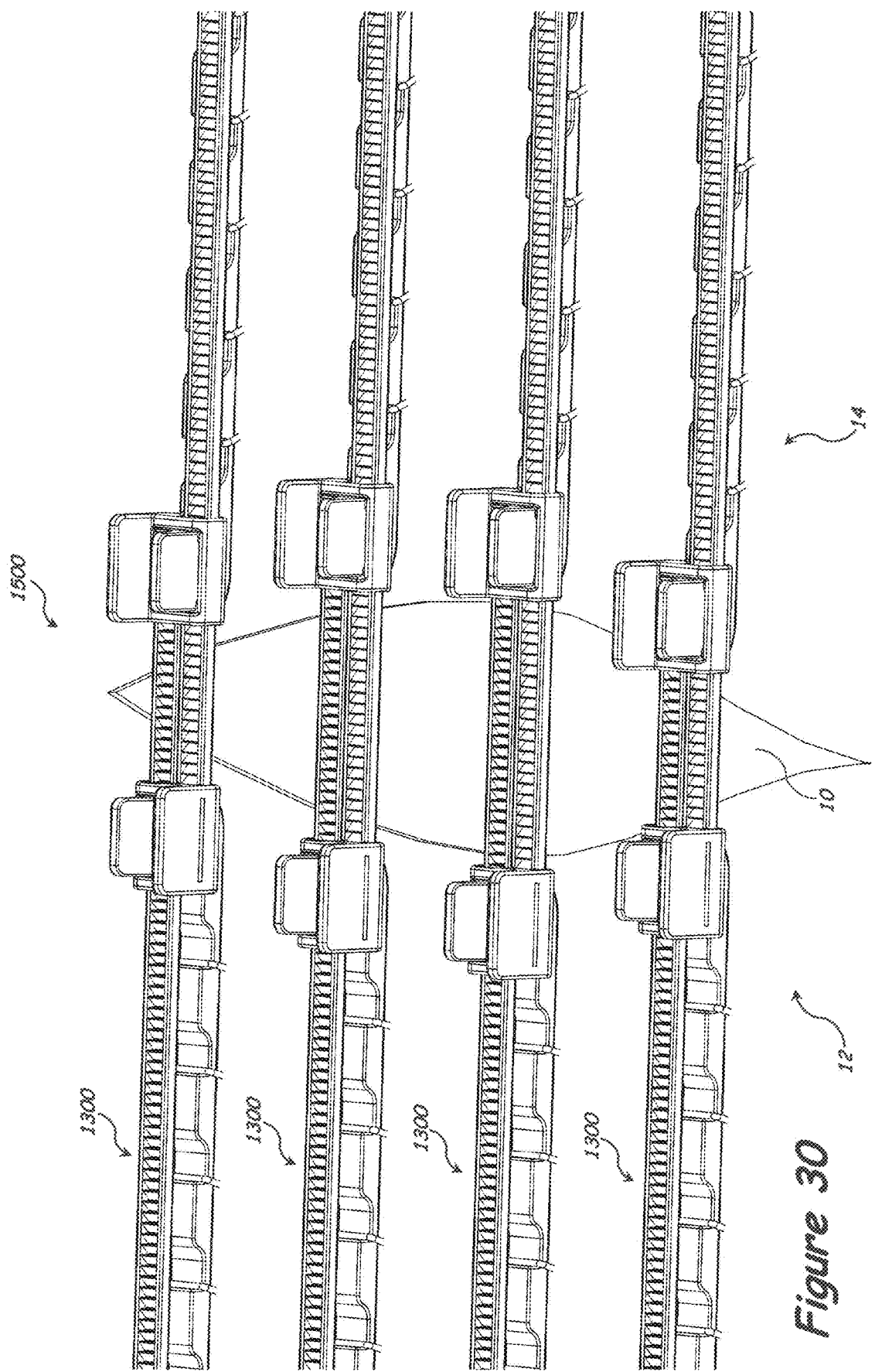
FIG. 30 is a side perspective view of the grouping of FIG. 27.

Referring now to FIGS. 23-26, a strap tie assembly 1300 is shown. The strap tie assembly 1300 is similar in structure and function to the strap tie assembly 1100 shown in FIGS. 20-22. FIG. 23 is a perspective view of the strap tie assembly 1300. The strap tie assembly includes a first strap tie 1310 and a second strap tie 1410. FIGS. 24-26 are detailed side, bottom, and end perspective views of the strap tie assembly 1300 in the vicinity of the second strap tie 1410, illustrating features of the engagement mechanism and the straps of the strap tie assembly 1300. The first strap tie 1310 includes a first strap body 1312, with a first strap 1316 extending from the first strap body 1312. A first base 1314 extends from the first body. The first strap tie 1310 includes a first engagement member 1322 and a first engagement base 1324 that are similar to the first engagement member 922 and the first engagement base 924 shown in FIGS. 16-19, with wider profiles (e.g., a length of the first engagement member 1322 along an axis parallel to the first strap 1316 is greater than a similar length of the first engagement member 922; a length of the first engagement base 1324 along an axis parallel to the first strap 1316 is greater than a similar length of the first engagement base 924; etc.). Similarly, the second strap tie 1410 includes a second strap body 1412, and a second engagement member 1422 and a second engagement base 1424 that are similar to the second engagement member 1022 and the second engagement base 1024 shown in FIGS. 16-19, with wider profiles. The second engagement member 1422 may be similar or identical to the first engagement member 1322; the second engagement base 1424 may be similar or identical to the first engagement base 1324. A second strap 1416, which is similar to the first strap 1316, extends from a second proximal end 1428 adjacent to the second strap body 1412 to a second distal end 1430, with second movement restriction members 1426 disposed along the second strap 1416.

Referring further to FIG. 24, the first strap 1316 may terminate in a first handle region 1336 that extends towards a distal end 1330 of the first strap 1316. The first handle region 1336 is provided at an angle relative to the rest of the first strap 1316. As shown in FIGS. 23-26, when the strap tie assembly 1300 has been assembled, the first handle region 1336 extends at an angle away from the second base 1414. The first handle region 1336 includes protrusions 1338. The protrusions 1338 may be similar or identical to other protrusions disclosed herein (e.g., protrusions 927 shown in FIG. 18; protrusions 1127 shown in FIG. 23, etc.). In some embodiments, the first handle region 1336 is relatively elongated as compared to the first strap 1316 (e.g., a length of the first handle region 1336 may be greater than one half the length of the first strap 1316, greater than one quarter the length of the first strap 1316, greater than one eight the length of the first strap 1316, etc.). The second strap 1416 may also terminate in a second handle region 1436 that is similar or identical to the first handle region 1336. As shown in FIG. 23, the second strap 1416 may include protrusions 1438 that are similar or identical to other protrusions disclosed herein.

Referring further to FIG. 25, a lower surface 1340 of the first handle region 1336 (e.g., a surface disposed proximate to the second base 1414 when the first strap 1316 has been received by the second strap tie 1410) includes protrusions 1339. The protrusions 1339 may be similar or identical to the protrusions 1338. As shown in FIGS. 24-25, the protrusions 1338, 1339 are biased, facilitating manipulation of the strap tie assembly 1300 in which the engagement between the first strap 1316 and the second strap tie 1410 prevents translation of the first strap tie 1310 away from the second strap tie 1410. The second strap 1416 may also be provided with lower surface protrusions that are similar or identical to the protrusions 1339.

Referring further to FIG. 26, the second strap tie 1410 is configured to engage the first strap 1316 using a second engagement member 1422. The second engagement member 1422 includes a second engagement unit 1423 that may be disposed within a second opening 1418 of the second strap tie 1410. When the second strap tie 1410 receives the first strap 1316 through the second opening 1418, the second engagement unit 1423 engages a first movement restriction member 1326 of the first strap tie 1316. The first strap 1316 includes a first ramp region 1320 between the first movement restriction members 1326 and the first handle region 1336. The first ramp region 1320 may facilitate translation of the first strap 1316 through the second opening 1418, by providing a thickness gradient between the relatively thin first handle region 1336 and the relatively thick region of the first strap 1316 that includes the first movement restriction members 1326. The second strap 1416 may be similar or identical to the first strap 1316.

In various embodiments, multiple strap tie assemblies (e.g., strap tie assemblies 100, 300, 500, 700, 900, 1100, 1300) may be used to secure and/or close a wound, such as in a strap tie grouping. For example, a first strap tie assembly 100 may be disposed across a first region of a wound in order to secure the first region of the wound, and a second strap tie assembly 300 may be disposed across a second region of a wound in order to secure the second region of the wound. The wound regions may have similar properties (e.g., cross-wound distance, healing status, etc.) and the strap tie assemblies may be drawn to similar tightness in order to apply an even amount of force across the wound. The wound regions may have different properties and the strap tie assemblies may be drawn to different tightnesses in order to apply an even amount of force across the wound. Various numbers and lengths of strap ties and strap tie assemblies may be used to secure and/or close the wound (e.g., depending on the location of the body where the wound has occurred; the curvature of the skin; the sensitivity of regions near the wound such as organs, joints, facial structures; etc.). In some embodiments, a strap tie grouping includes multiple strap ties for each side of a wound joined together. The multiple strap ties may be joined together with a tie, a line, a thread, a strip, etc. The multiple strap ties may be joined together with a strip of adhesive, such that the multiple strap ties may be held in place together and also attached to a portion of skin. In some embodiments, a strap tie grouping includes between two and five strap ties for each side of a wound.

Referring now to FIGS. 27-30, multiple strap tie assemblies 1300 are provided together as a strap tie grouping 1500. The strap tie grouping 1500 is disposed across a wound 10, with a set of first strap ties 1310 disposed on a first portion of skin 12, and a set of second strap ties 1410 disposed on a second portion of skin 14. The strap tie grouping 1500 may be attached to the skin in any manner as described herein. As shown in FIGS. 27-30, the strap tie assemblies 1300 have been adjusted to different tightnesses (e.g., the distance between the first strap body 1312 and the second body 1412), such that the wound tapers from a relatively thin portion at the outer edges 16, 18 to a relatively thick portion in the center 20. In various embodiments, various qualities of the wound may be used to determine how tightly each strap tie assembly 1300 is adjusted in order to variously tighten portions of skin across the wound.

Figure 31:
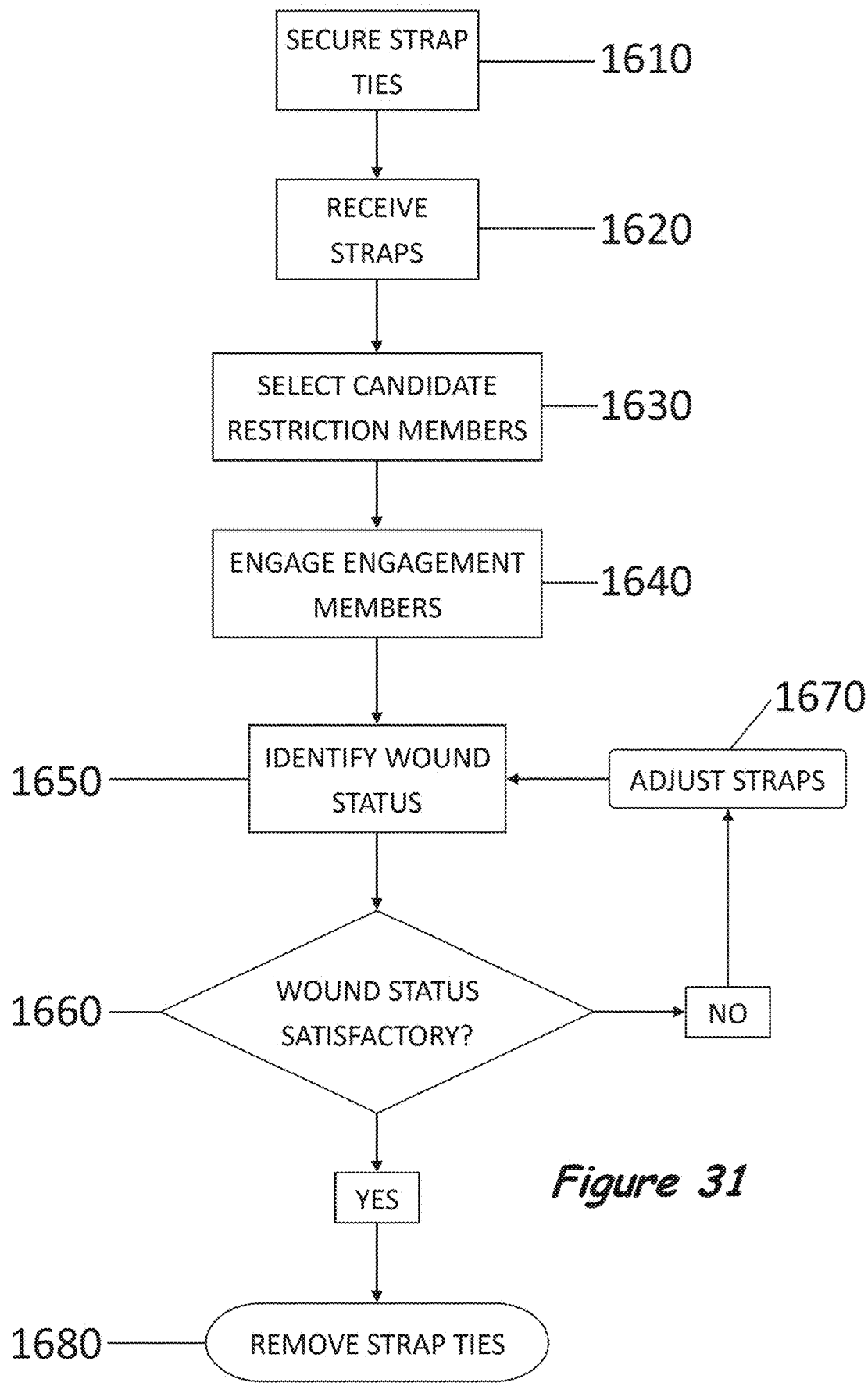
FIG. 31 is a block diagram of an embodiment of a method of securing a wound with an even amount of force applied across the wound using a strap tie assembly.

Referring now to FIG. 31, a block diagram of an embodiment of a method 1600 of securing a wound using a strap tie system is shown. The method may be implemented using any of the strap tie assemblies and devices disclosed herein, such as strap tie assemblies 100, 300, 500. A variety of users may perform the method, including but not limited to an individual having a wound, a medical care professional (e.g., doctor, nurse, etc.), a patient, a trauma care provider, a field care provider, a civilian, a soldier, etc.

At 1610, a first strap tie is secured adjacent to a first portion of skin on a first side of a wound, and a second strap tie is secured adjacent to a second portion of skin on a second side of a wound. The strap ties may be secured in any manner as disclosed herein (e.g., detachably secured, attached, removably coupled, etc.). The strap ties may be secured using attachment members (e.g., staples, hooks, adhesives, etc.). In various embodiments, the strap ties are secured to the portions of skin at various distances from the wound (e.g., a selected distance from the wound), in order to apply a specific amount of force and/or tension across the wound (e.g., an even amount of force across the wound). In some embodiments, a user can secure the first strap tie adjacent to the first portion of skin on the first side of the wound, and a user can secure the second strap tie adjacent to the second portion of skin on the second side of the wound. In some embodiments, a user can select the distance from the wound that at least one of the first strap tie and the second strap tie is secured to a respective portion of skin.

At 1620, each strap tie receives a strap from the other strap tie. For example, the first strap tie receives a second strap from the second strap tie, through a first opening in a first body of the first strap tie, and the second strap tie receives a first strap from the first strap tie, through a second opening in a second body of the second strap tie. In some embodiments, a user can receive the second strap from the second strap tie through the first opening in the first body of the first strap tie by drawing (e.g., pulling, threading, pushing, etc.) the second strap through the first opening. Similarly, a user can receive the first strap from the first strap tie through the second opening in the second body of the second strap tie by drawing the second strap through the second opening. In some embodiments, the strap ties are already assembled as a strap tie assembly, so that a user (e.g., a medic, a surgeon, a technician, etc.) can tighten the straps (see 1630) immediately after securing the strap tie assembly.

At 1630, candidate movement restriction members are selected for engaging with engagement members of each tie strap. For example, a first candidate movement restriction member disposed along a surface of the first strap is selected, in order to be engaged by a second engagement member of the second strap tie. Similarly, a second candidate movement restriction member disposed along a surface of the second strap is selected, in order to be engaged by a first engagement member of the first strap tie. The candidate restriction members may be selected in order to apply an even amount of force across the wound. The candidate restriction members may be selected in order to draw each strap a certain distance through an opening of the other strap. The candidate restriction members may be selected based on an effect on the portions of skin or on the wound, such as a distance between the portions of skin as the wound is closed, etc. In some embodiments, a user can select the first candidate restriction member for the first strap, and a user can select the second candidate restriction member for the second strap.

At 1640, the engagement members are engaged to the respective candidate movement restriction members. For example, the first engagement member of the first strap tie is engaged to the second candidate movement restriction member, and the second engagement member of the second strap tie is engaged to the first candidate movement restriction member. Engagement members and movement restriction members may be engaged by drawing the straps a certain distance through respective openings of the strap ties until the engagement members are aligned with/engage the appropriate movement restriction member. A user can engage the first engagement member to the second candidate movement restriction member by aligning the first engagement member with the second candidate movement restriction member and engaging, joining, attaching, or otherwise coupling the first engagement member and the second candidate movement restriction member. A user can engage the second engagement member to the first candidate movement restriction member by aligning the second engagement member with the first candidate movement restriction member and engaging, joining, attaching, or otherwise coupling the second engagement member and the first candidate movement restriction member.

At 1650, a wound status is identified. The wound status may relate to various qualities and properties of the wound, including but not limited to the health of the wound, the presence of any infections in the wound, the size of the wound (e.g., the distance between the first portion of skin on one side of the wound and the second portion of skin on the other side of the wound, etc.), any relative changes in the wound, the structural integrity of the wound (including inflation), the elasticity of the wound, tissue, or skin, etc. A user may identify the wound status, such as by observing the wound, using a sensor or other medical device to non-invasively identify properties of the wound, performing a test on the wound or material within the wound, measuring visible properties of the wound, etc.

At 1660, a determination is made as to whether the wound status is satisfactory. For example, the wound status may be satisfactory if the wound is healing properly. The wound status may be unsatisfactory if the wound is infected, if the portions of skin on either side of the wound need to be drawn more closely together, if the force applied across the wound is not even, etc. A user may determine whether the wound status is satisfactory by comparing the wound status to a heuristic, a flow chart, or any other plan or strategy relevant to wound closure and wound healing.

If the wound status is not satisfactory (e.g., unsatisfactory), then at 1670, the straps are adjusted to alter the positions of the strap ties and thus the portions of skin disposed on either side of the wound. In some embodiments, the wound status is not satisfactory because the force applied across the wound is not even. As such, at least one of the straps may be adjusted (e.g., drawn further through an opening of the other strap tie) in order to ensure that the force applied across the wound is even. A strap may be adjusted by grasping a portion of the strap (e.g., a distal end, etc.), and drawing the strap further (e.g., in a direction other than a direction in which the strap would be decoupled from the other strap tie) through the opening of the other strap tie. A user may adjust the positions of one or more strap ties by holding or otherwise grasping the strap of the strap tie, and drawing the strap further through the corresponding opening until a desired position is reached, such as a position at which the force applied across the wound is even.

If the wound status is satisfactory, then at 1680, the strap tie assembly may be removed (e.g., unsecured, desecured, etc.). For example, attachment members may be removed from the portions of skin on either side of the wound. A user may remove the attachment members manually, by using a tool for removing the attachment members, etc.

In some embodiments, adjusting the straps includes engaging the engagement members with a new candidate movement restriction member. For example, a wound status may be unsatisfactory because the force applied across the wound is not even. A new candidate first movement restriction member may be selected along the first strap, and the first strap may be adjusted by drawing the first strap further through an opening of the second strap tie, then engaging the new candidate first movement restriction member with the appropriate second engagement member. A user may identify a new candidate movement restriction member, adjust the position of the straps, and engage the engagement member to the corresponding movement restriction member.

In some embodiments, a strap tie assembly is secured across a wound in a particular order. For example, a first strap tie may be secured to a first portion of skin; next, a second strap may be received through a first opening in the first strap tie; next, the second strap tie from which the second strap extends may receive a first strap extending from the first strap tie; next, the second strap tie may be secured to a second portion of skin across a wound from the first portion of skin. In various embodiments, the order of these steps may be modified based on the availability of strap ties, the availability of attachment members, the status of the wound, the amount of time available to secure the wound, etc.

In some embodiments, the straps may be applied and reapplied from portions of skin adjacent to a wound. For example, a strap tie assembly may be used to secure a wound, then desecured (e.g., detached, removed, etc.) from the wound, then resecured (e.g., reattached, etc.) to the wound at a similar or different distance from or position relative to the wound, with a similar or different amount of force applied across the wound, etc. In some embodiments, a user may detach a strap tie assembly that was already secured to portions of skin adjacent to a wound from the portions of skin, and may reattach the strap tie assembly to the portions of skin.

Referring now to FIGS. 32-38B, a strap tie assembly 1700 is shown. The strap tie assembly 1700 is similar in structure and function to the various strap tie assemblies disclosed herein, including strap tie assembly 900 shown in FIGS. 16-19. While FIGS. 33-37 illustrate detail views of interactions between a first strap 1716 of a first strap tie 1710 and a second strap tie 1810, in various embodiments, the first strap tie 1710 and second strap tie 1810 can be similar or identical such that the first strap tie 1710 and second strap tie 1810 perform similar or identical functions (e.g., the first strap tie 1710 and second strap tie 1810 can be coupled or engaged to one another in mirror image orientations, etc.).

In some embodiments, the strap tie assembly 1700 includes a first strap tie 1710 and a second strap tie 1810. The first strap tie 1710 includes a first base 1714 configured to be disposed adjacent to a first portion of skin. The first base 1714 can define a first plurality of openings 1732. The first strap tie 1710 includes a first body 1712. The first body 1712 includes a first receiving channel 1718 and a first engagement member 1720. The first strap tie 1710 includes a first strap 1716. The first strap 1716 extends from the first body 1712. The first strap 1716 includes a first proximal end 1728 attached to the first body 1712, a first distal end 1730 opposite the first proximal end 1728, and a plurality of first movement restriction members 1734 disposed along a surface of the first strap 1716. The first strap defines a first longitudinal axis 1702.

In some embodiments, the second strap tie 1810 includes a second base 1814 configured to be disposed adjacent to a second portion of skin. The second base 1814 can define a second plurality of openings 1832. The second strap tie 1810 includes a second body 1812. The second body 1812 includes a second receiving channel 1818 and a second engagement member 1820. The second strap tie 1810 includes a second strap 1816. The second strap 1816 extends from the second body 1812. The second strap 1816 includes a second proximal end 1828 attached to the second body 1812, a second distal end 1830 opposite the second proximal end 1828, and a plurality of second movement restriction members 1834 disposed along a surface of the second strap 1816. The second strap defines a second longitudinal axis.

In some embodiments, the first receiving channel 1718 is configured to receive the second strap 1816. The first engagement member 1720 can be configured to be rotated (e.g., pivoted) about a first rotational axis parallel to the second longitudinal axis to engage one of the plurality of second movement restriction members 1834 of the second strap 1816 to prevent translation of the second strap 1816 away from the first body 1712.

In some embodiments, the second receiving channel 1818 is configured to receive the first strap 1716. The second engagement member 1820 can be configured to be rotated (e.g., pivoted) about a second rotational axis 1804 parallel to the first rotational axis 1704 to engage one of the plurality of first movement restriction members 1734 of the first strap 1716 to prevent translation of the first strap 1716 away from the first body 1712.

In some embodiments, the first plurality of openings 1732 of the first base 1714 are configured to allow access to the first portion of skin through the first plurality of openings 1732. Similarly, the second plurality of openings 1832 of the second base 1814 can be configured to allow access to the second portion of skin through the second plurality of openings 1832. For example, when the first base 1714 is positioned on the first portion of skin, the first portion of skin is exposed through the first plurality of openings 1732, such that attachment or fastening members (e.g., staples, screws, adhesive members, other attachment or fastening members disclosed herein, etc.) can be secured (e.g., attached) to the skin through the first plurality of openings 1732. As shown, for example, in FIG. 32, each opening 1732 has a rectangular shape. In various embodiments, one or more of the openings 1732 can have various shapes (e.g., circular, oval, triangular, other polygonal shapes, etc.). The second plurality of openings 1832 can be similar or identical to the first plurality of openings 1732. While the pluralities of openings 1732, 1832, are illustrated in two rows along the respective bases, in various embodiments, the openings can be arranged in various formats (e.g., arrays, matrices, non-linear orders, etc.).

Figure 33:
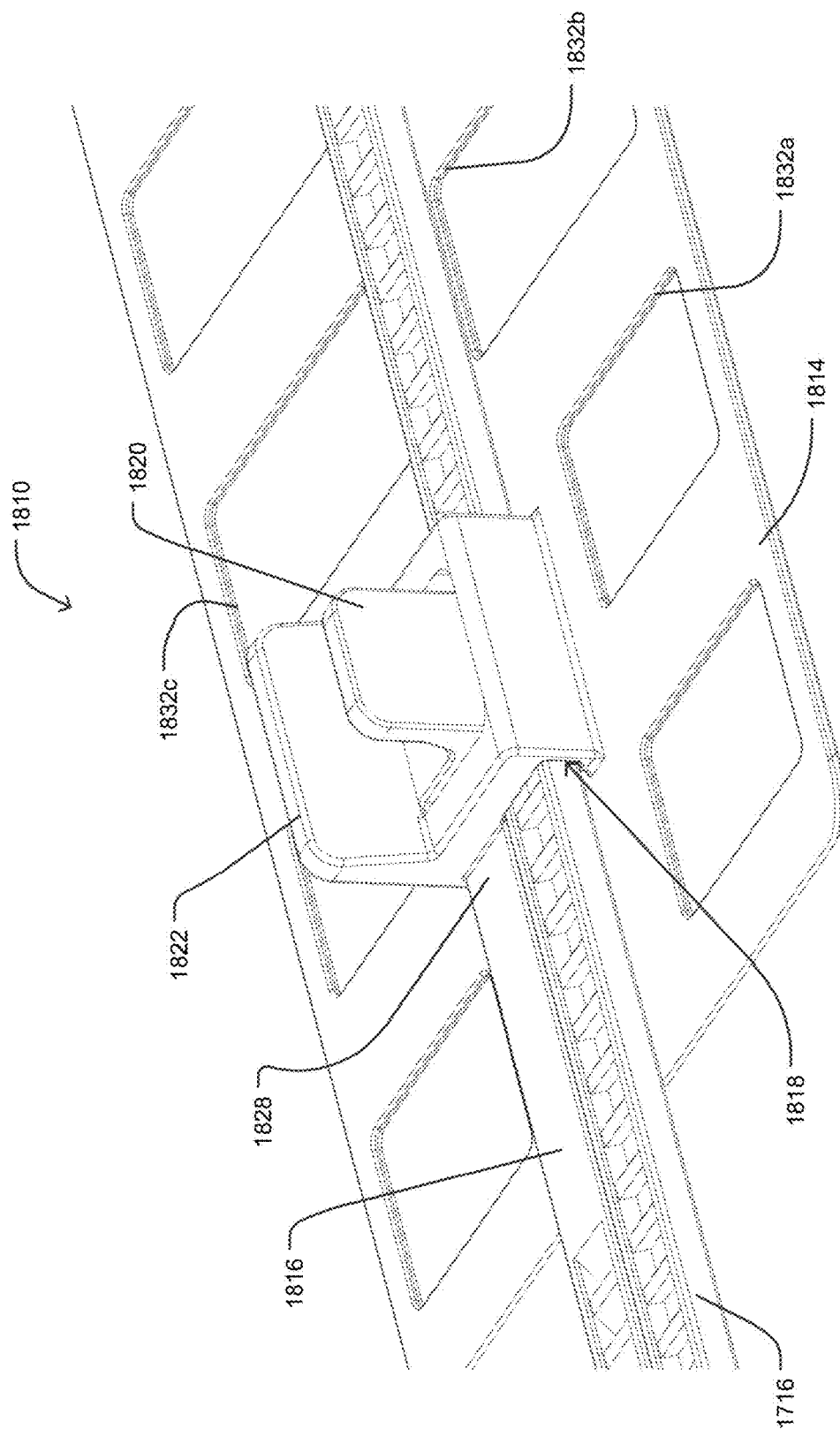
FIG. 33 is a detailed perspective view of an embodiment of a body of a strap tie of the strap tie assembly of FIG. 32.

In some embodiments, at least two of the first plurality of openings 1732 and/or the second plurality of openings 1832 are sized and spaced apart from one another to allow a staple to be attached to the first portion of skin through the at least two openings. For example, as shown in FIG. 33, a staple could be attached to the second portion of skin through openings 1832a and 1832b, such as by positioning one leg of a staple through opening 1832a and another leg through opening 1832b, such that a central portion of the staple connecting the legs is positioned against the second base 1814 between the openings 1832a, 1832b. A staple could also be attached to the second portion of skin through openings 1832a and 1832c, such as by positioning one leg of a staple through opening 1832a and another leg through opening 1832c, such that a central portion of the staple connecting the legs is positioned against the second base 1814 between the openings 1832a, 1832c. In responses to forces applied to the second strap tie 1810, such as forces applied to the second base 1814, the second base 1814 is not translated relative to the second portion of skin due to the force applied by the central portion of the staple against the second base 1814 in a direction towards the second portion of skin.

Figure 36:
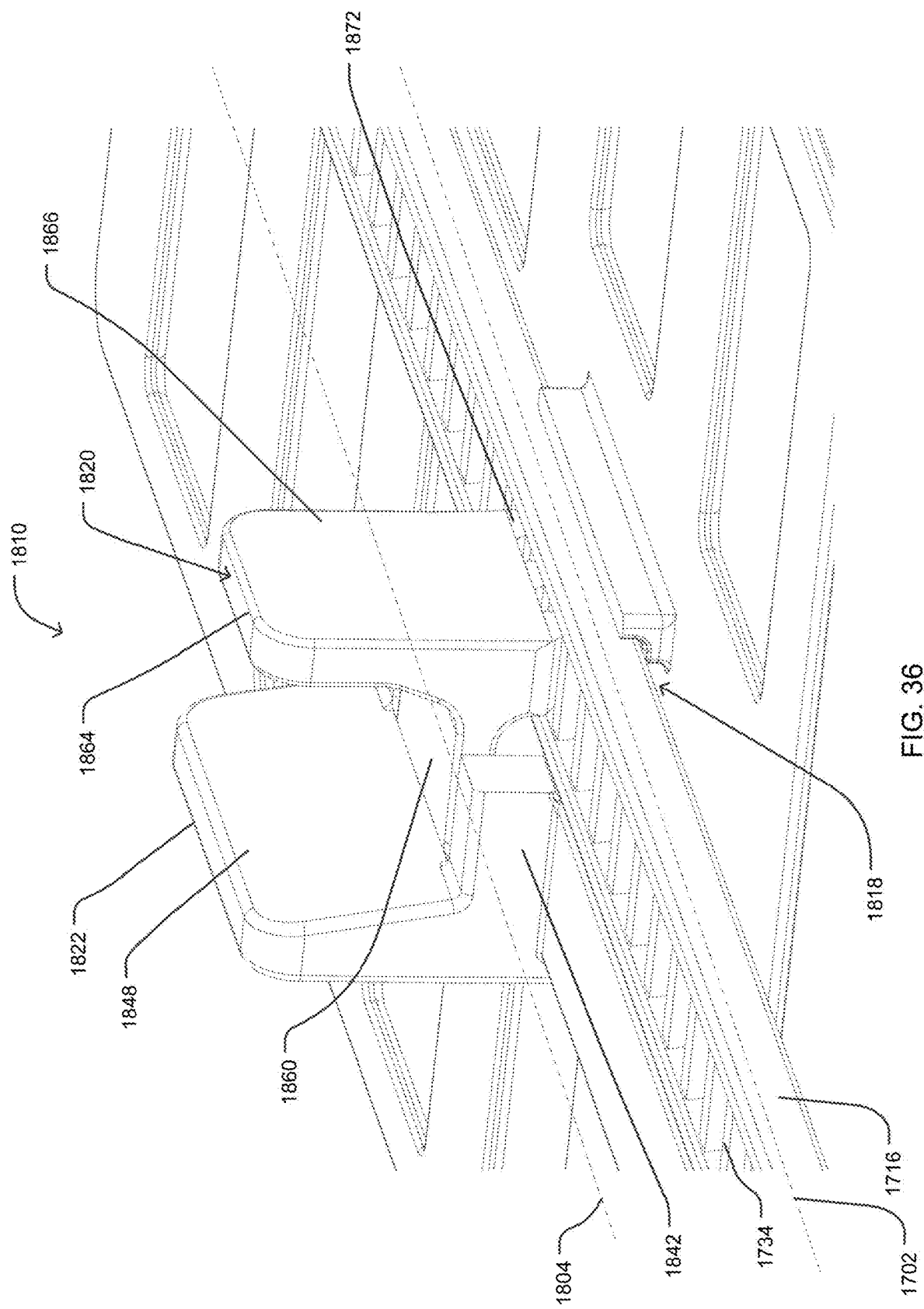
FIG. 36 is a partial view of an embodiment of the strap tie assembly of FIG. 32 in which an engagement member is engaged to a strap.

In some embodiments, at least two openings 1832 are defined (e.g., positioned, located, etc.) relative to one another in a direction that is at least one of parallel to the second rotational axis 1804 or perpendicular to the second rotational axis 1804. For example, as shown in FIGS. 33 and 36, openings 1832a and 1832b are defined relative to one another in a direction that is parallel to the second rotational axis 1804, and openings 1832a and 1832c are defined relative to one another in a direction that is perpendicular to the second rotational axis 1804. In various embodiments, various numbers of openings of the bases 1714, 1814 can be used for receiving staples. For example, the number of receiving staples can depend on factors such as the time available for securing the strap tie assembly 1700 to the portions of skin, the locations of the portions of skin, the size of a wound between the portions of skin, the likelihood that remote objects will interfere with the strap tie assembly 1700, etc.

Figure 32:
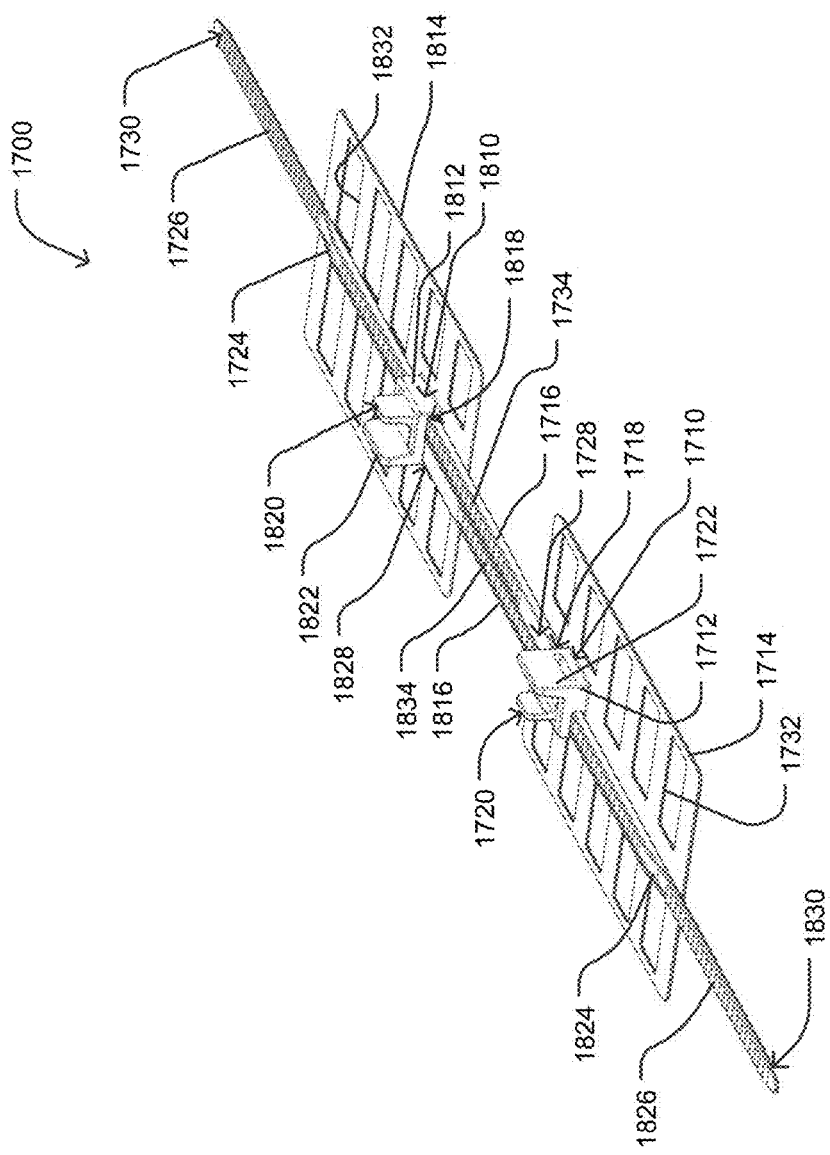
FIG. 32 is a perspective view of an embodiment of a strap tie assembly in which each strap tie includes a base with openings configured for staples.

In some embodiments, such as shown in FIG. 32, the first base 1714 includes a rectangular shape. In various embodiments, the first base 1714 can include various shapes (e.g., circular, oval, triangular, tapering from a first end at which the first base 1714 is attached to the first body 1712 to a second end opposite the first end, etc.). In some embodiments, the first base 1714 can be configured to be attached to the first portion of skin. For example, the first base 1714 can include adhesive on a surface of the first base 1714 to be positioned on the first portion of skin. A cover member (e.g., paper, etc.) can be positioned on the adhesive and first base 1714, and then removed from the first base 1714 in order to expose the first base 1714 for attachment to the first portion of skin. In some embodiments, the first base 1714 and/or the second base 1814 can include a flexible material (e.g., bendable, pliable), such as a flexible plastic, allowing the first base 1714 and/or the second base 1814 to conform to portions of skin.

While FIGS. 32-38B illustrate the first base 1714 and the second base 1814 define openings 1732, 1832, respectively, in various embodiments, the first base 1714 and/or the second base 1814 do not define openings. For example, the first base 1714 and/or the second base 1814 can include or define a continuous or solid surface. In some embodiments, the first base 1714 and/or the second base 1814 is configured to be penetrated by a staple (e.g., the first base 1714 and/or the second base 1814 includes a soft material, plastic material, pierceable material, etc., that can be penetrated by a staple), such that a user can staple the first base 1714 and/or the second base 1814 through the first base 1714 and/or the second base 1814.

In some embodiments, as shown in FIG. 32, the first base 1714 has a depth (e.g., length in a dimension perpendicular to the first portion of skin when the first base 1714 is positioned on the first portion of skin, and/or parallel to the rotational axis of the first engagement member 1720) that is much less (e.g., at least a factor of 2, a factor of 5, an order of magnitude less, etc.) than a breadth and/or width (e.g., lengths in dimensions parallel to the first portion of skin when the first base 1714 is positioned on the first portion of skin, and/or perpendicular to the rotational axis of the first engagement member 1720). For example, the first base 1714 can have a relatively thin or planar shape. Such a shape of the first base 1714 can facilitate securing the strap tie 1710 to the first portion of skin using staples passing through the first plurality of openings 1732, facilitate a compact, user-friendly form for the first strap tie 1710, and reduce or minimize the profile of the first strap tie 1710 so as to reduce the likelihood that objects moving around the first strap tie 1710 interfere with the first base 1714 (e.g., cause the first base 1714 to be pulled away from the first portion of skin). In some embodiments, the desire for a relatively thin first base 1714 can be mitigated by a desire for the first plurality of openings 1732 to have relatively long sidewalls against which staples are secured to the first portion of skin (e.g., if the first base 1714 is too thin, then it might tear in response to forces applied to the strap tie 1710 that are transferred to the staples and the first plurality of openings 1732 positioned against the staples). The second base 1814 can be similar or identical to the first base 1714.

In some embodiments, the second engagement member 1820 includes an engagement feature 1872. The engagement feature 1872 is configured to engage the first strap 1716. For example, the engagement feature 1872 can be configured to be positioned adjacent to a feature of the first strap 1716 to limit or prevent translation of the first strap 1716 relative to the second engagement member 1820, such as translation that would otherwise occur in response to a force applied along a longitudinal axis of the first strap 1716. In various embodiments, the engagement feature 1872 can include a tooth, pawl, ridge, or other surface feature configured to engage (e.g., frictionally engage) the first strap 1716 and/or complementary features of the first strap 1716.

In some embodiments, the engagement feature 1872 extends in a direction transverse to the second rotational axis 1804, such that rotating the second engagement member 1820 about the second rotational axis 1804 positions the engagement feature 1872 adjacent to one of the plurality of first movement restriction members 1734 when the first strap 1716 is received in the second receiving channel 1818. In some embodiments, the engagement feature 1872 locks the first strap 1716 in place relative to the second body 1812.

In some embodiments, similar to other strap tie assemblies disclosed herein, the engagement feature 1872 can be configured to allow the first strap 1716 to translate in a first direction (e.g., towards the second body 1812) and prevent the first strap 1716 from translating in a second direction (e.g., away from the second body 1812). For example, the engagement feature 1872 can include a first surface angled in a first direction and a second surface angled in a second direction different from the first surface such that the engagement feature 1872 ratchets with respect to the first strap 1716 and/or first movement restriction members 1734 of the first strap 1716.

Figure 37:
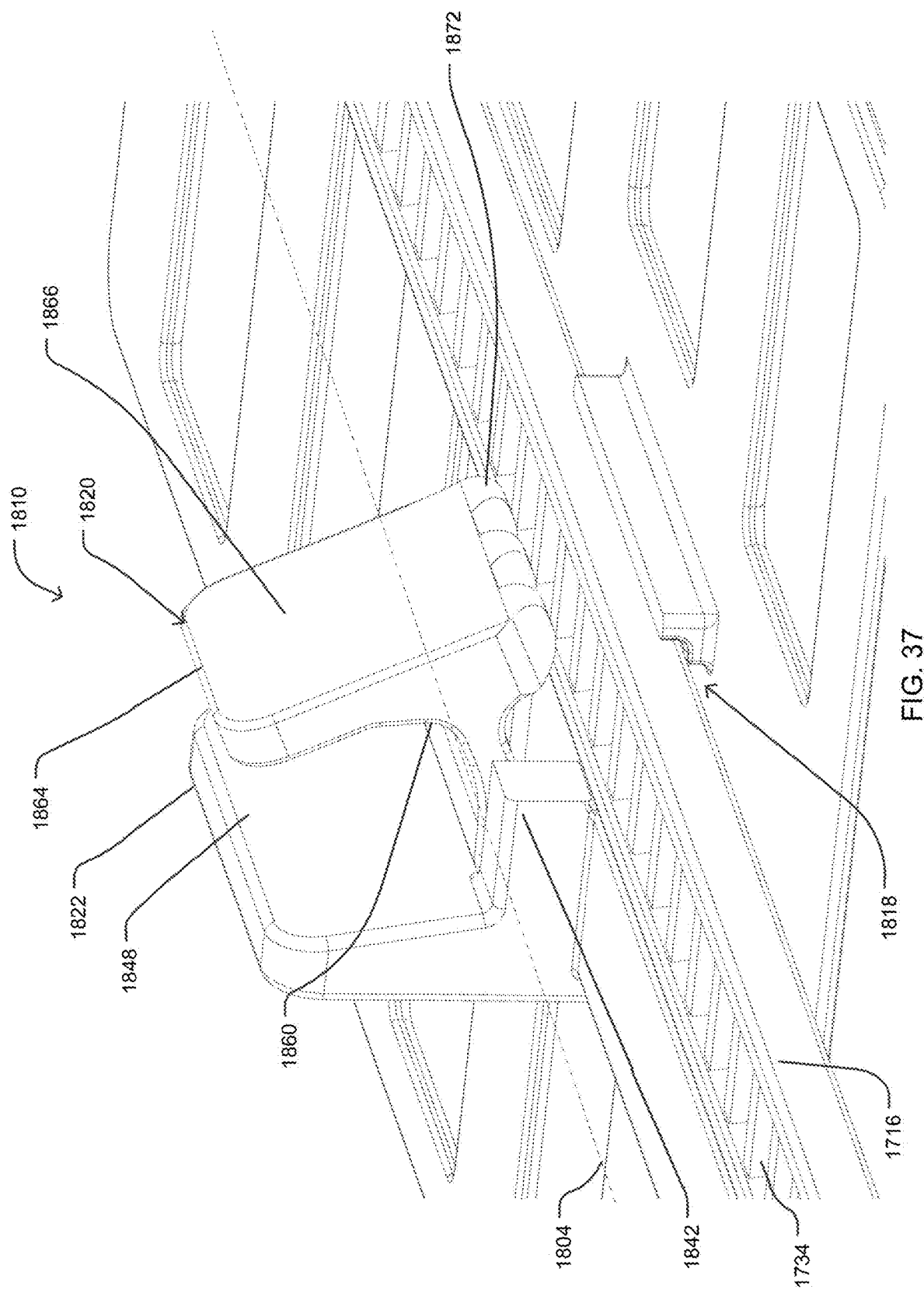
FIG. 37 is a partial view of an embodiment of the strap tie assembly of FIG. 32 in which an engagement member has been rotated to disengage a strap.
Figure 38:
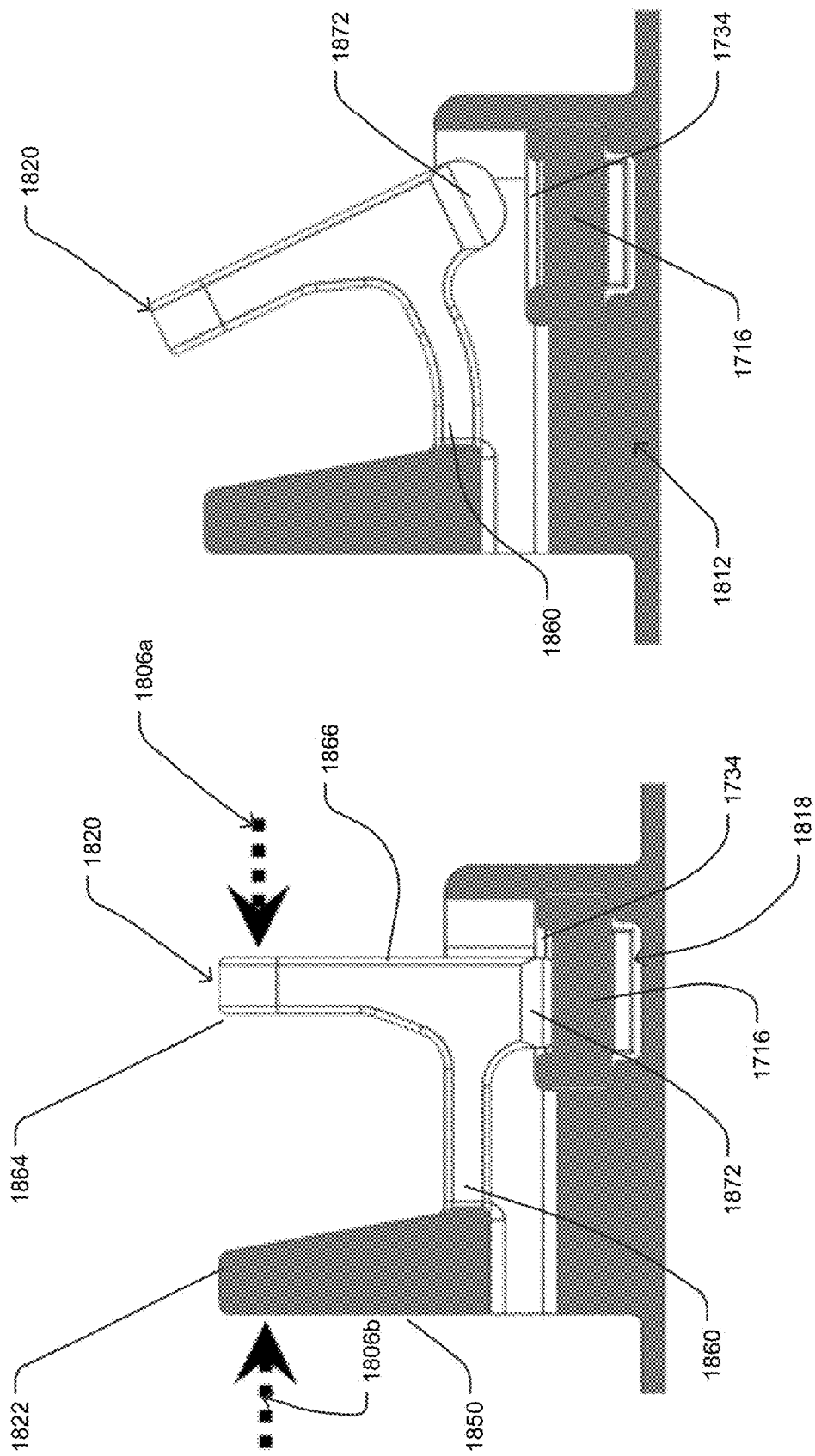
FIGS. 38A-38B are schematic diagrams of embodiments of the strap tie assembly of FIG. 32 illustrating an actuation force applied to disengage an engagement member from a strap.

In some embodiments, the second engagement member 1820 includes a plurality of engagement features 1872 extending transverse to the second rotational axis 1804 and oriented sequentially along an axis parallel to the second rotational axis 1804, such that rotating the second engagement member 1820 about the second rotational axis 1804 positions the plurality of engagement features 1872 adjacent to and between a corresponding set of the plurality of first movement restriction members 1734 when the first strap 1716 is received in the second receiving channel 1818. For example, as shown in FIGS. 36-37, the second engagement member 1820 includes a plurality of engagement features 1872 that can be positioned between corresponding first movement restriction members 1734 when the first strap 1716 is received in the second receiving channel 1818. In some embodiments, the second engagement member 1820 is configured to removable engage one or more first movement restriction members 1734 of the first strap 1716.

In some embodiments, the second engagement member 1820 is rotatably attached to a second sidewall 1822 of the second body 1812. The second sidewall 1822 can be oriented transverse to the second rotational axis 1804. The second sidewall 1822 can act as a resistance surface relative to the second engagement member 1820, allowing the second engagement member 1820 to be squeezed towards the second sidewall 1822 in a two-finger operation in order to rotate the second engagement member 1820 to disengage the second engagement member 1820 from the first strap 1716. By providing a resistance surface, the second sidewall 1822 facilitates manipulation/actuation of the second engagement member 1820 without translating the entire second strap tie 1810 relative to the second portion of skin, such as a translation that would strain or tear staples used to secure the second base 1814 to the second portion of skin.

The second sidewall 1822 can be oriented perpendicular to the second base 1814 such that the second sidewall 1822 is oriented perpendicular to the second portion of skin when the second strap tie 1810 is positioned adjacent to the second portion of skin. The second sidewall 1822 can include frictional engagement features (e.g., rough surfaces, serrated surfaces, grip surfaces, etc.) configured to facilitate handling of the second strap tie 1810 and/or actuation of the second engagement member 1820. For example, the strap tie assembly 1700 may be used in environments with fluids (e.g., water, blood, etc.) that make the strap tie assembly 1700 slippery (e.g., decrease friction when handling the strap tie assembly 1700), such that the frictional engagement features mitigate such decreases in friction.

In some embodiments, the second sidewall 1822 is configured to be coupled to the second engagement member 1820. For example, the second sidewall 1822 can include a receiving member (e.g., latch, notch, etc.) configured to engage the second engagement member 1820 when the second engagement member 1820 is rotated about the second rotational axis 1804 towards the second sidewall 1822. For example, an inner surface 1848 of the second sidewall 1822 can include a receiving member configured to engage the second engagement member 1820.

In some embodiments, the second engagement member 1820 includes a second engagement wall 1864 oriented transverse to the second rotational axis 1804. The second engagement member 1820 can be configured to be rotated by applying a force against the second engagement wall 1864 in a direction towards the second sidewall 1822 of the second body 1812, the second sidewall 1822 providing a resistance surface such that the force can be applied by squeezing, pressing or pushing the second engagement wall 1864 towards the second sidewall 1822. For example, as shown in FIG. 38A, forces can be applied (e.g., applied simultaneously) against an outer engagement wall 1866 of the second engagement member 1820 (e.g., a force applied in a direction 1806a towards the second sidewall 1822) and against an outer wall 1850 of the second sidewall 1822 (e.g., a force applied in a direction 1806b towards the second engagement member 1820). In some embodiments, in response to squeezing forces applied to the second engagement member 1820 and the second sidewall 1822 in the directions 1806a, 1806b, respectively, the second engagement member 1820 is rotated about the second rotational axis 1804. As shown in FIG. 38B, after the second engagement member 1820 is rotated, the engagement features 1872 disengage from movement restriction members 1734 of the first strap 1716, allowing the first strap 1716 to be translated relative to the second body 1812.

In some embodiments, the second engagement member 1820 includes a flexible material such that a portion 1860 of the second engagement member 1820 remains fixed as the second engagement member 1820 is rotated about the rotational axis 1804. For example, the portion 1860 can include flexible plastic, rubber, etc., allowing the second engagement wall 1864 to rotate about the rotational axis 1804 while the portion 1860 remains attached to the second sidewall 1822. In other embodiments, the second engagement member 1820 is attached to the second sidewall 1822 via a rotational member, such as a hinge or pivot member, such that the portion 1860 also rotates (e.g., pivots) about the rotational axis 1804 as the second engagement member 1820 is rotated about the rotational axis 1804.

In some embodiments, the second engagement member 1820 is configured to be biased to a first position (e.g., the position of the second engagement member 1820 shown in FIGS. 36 and 38A, etc.) at which the second engagement member 1820 engages one of the plurality of first movement restriction members 1734. For example, the second engagement member 1820 can include flexible and/or resilient material such that the second engagement member 1820 can be flexed away from the first position in response to force applied to the second engagement member 1820 in order to rotate the second engagement member 1820 about the rotational axis 1804 to disengage the second engagement member 1820 from the first strap 1716. In the absence of a force applied to the second engagement member 1820, the second engagement member 1820 is then restored to the first position.

In some embodiments, the second engagement member 1820 is configured to be oriented in a plurality of orientations about the rotational axis 1804, including an orientation in which the second engagement member 1820 can be engaged to the first strap 1716 and an orientation in which the second engagement member 1820 is disengaged from the first strap 1716. For example, the second engagement member 1820 can include (or be attached to the second sidewall 1822 via) a pivot member or hinge. The pivot member or hinge can be configured to maintain the second engagement member 1820 in any of the plurality of orientations in the absence of force applied by a user. For example, the pivot member or hinge can include receiving members (e.g., notches, gears, etc.) allowing the second engagement member 1820 to be positioned in discrete orientations at discrete angles about the rotational axis 1804. The pivot member or hinge can be positioned flush with an interior surface of the second body 1812 such that friction between the interior surface and the pivot member or hinge counteracts gravity or other forces on the second engagement member 1820, such that the second engagement member 1820 does not move from a current orientation in the absence of an outside force greater than a threshold force, the threshold force corresponding to the friction between the interior surface and the pivot member or hinge.

In some embodiments, such as in the frame of reference shown in FIG. 33, the strap tie assembly 1700 is configured such that the first strap 1716 and second strap 1816 are positioned or otherwise configured to be side-by-side (rather than on top of one another, such as shown in FIG. 1) when the first strap 1716 is received in the second receiving channel 1818 and the second strap 1816 is received in the first receiving channel 1718. For example, the first proximal end 1728 can be positioned adjacent to the first receiving channel 1718, and the first receiving channel 1718 can be positioned between the first engagement member 1720 and the first base 1714. Similarly, the second proximal end 1828 can be positioned adjacent to the second receiving channel 1818, and the second receiving channel 1818 can be positioned between the second engagement member 1820 and the second base 1814.

Referring further to FIG. 32, in some embodiments, the straps can taper from a relatively thicker portion adjacent to the proximal end to a relatively thinner portion adjacent to the distal end (e.g., similar to the tapered shape of the straps of strap tie assembly 100 as shown in FIG. 1, etc.). This can facilitate receiving the straps in corresponding channels of remote strap ties. For example, as shown in FIG. 32, the first strap 1716 includes a first taper portion 1724 positioned between the first proximal end 1728 and the first distal end 1730, such that the first strap 1716 tapers to a first distal portion 1726 adjacent to the first distal end 1730. Similarly, the second strap 1816 includes a second taper portion 1824 positioned between the second proximal end 1828 and the second distal end 1830, such that the second strap 1816 tapers to a second distal portion 1826 adjacent to the second distal end 1830.

Figure 34:
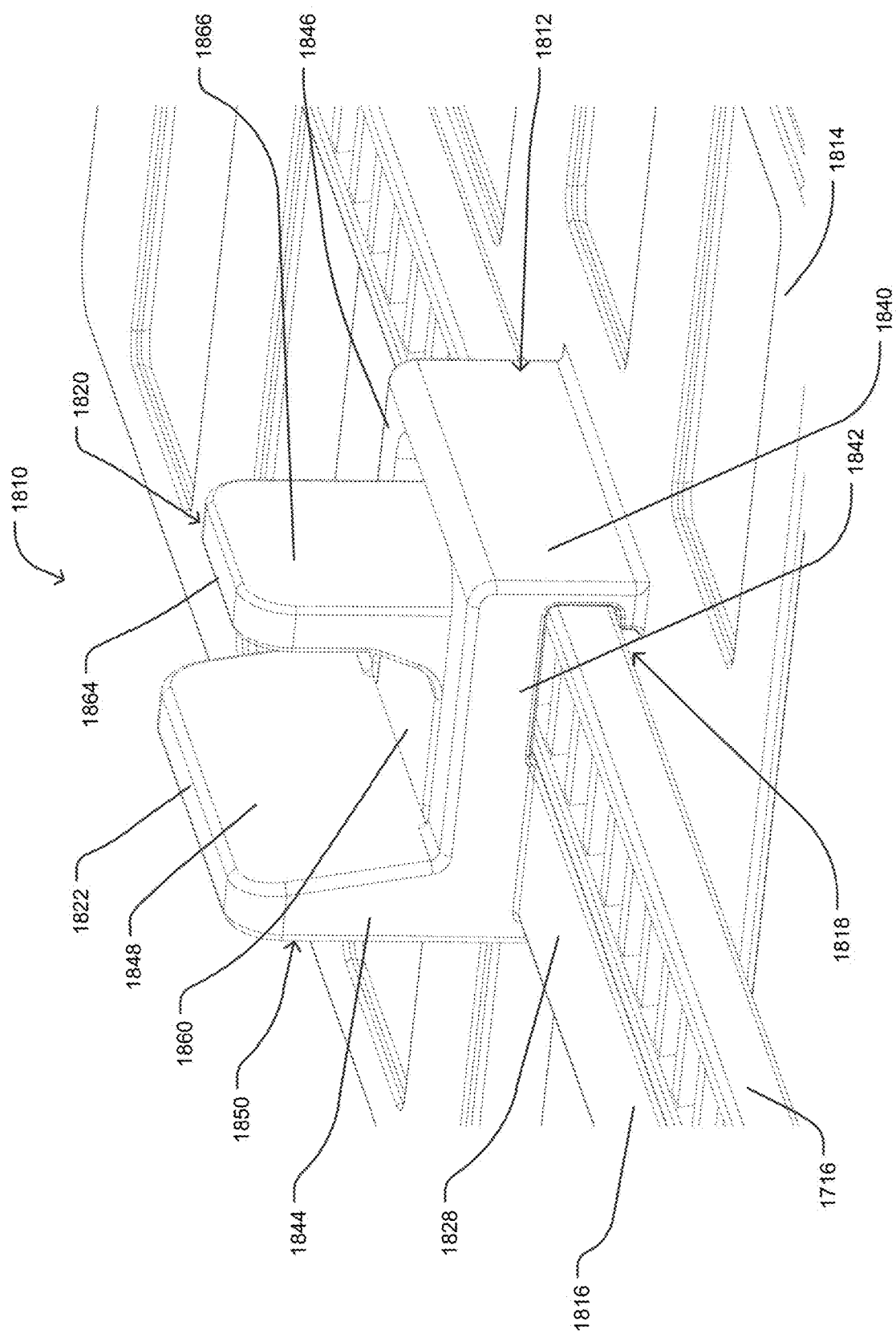
FIG. 34 is a detailed perspective view of an embodiment of the strap tie assembly of FIG. 32 in which an engagement member is engaged to a strap.
Figure 35:
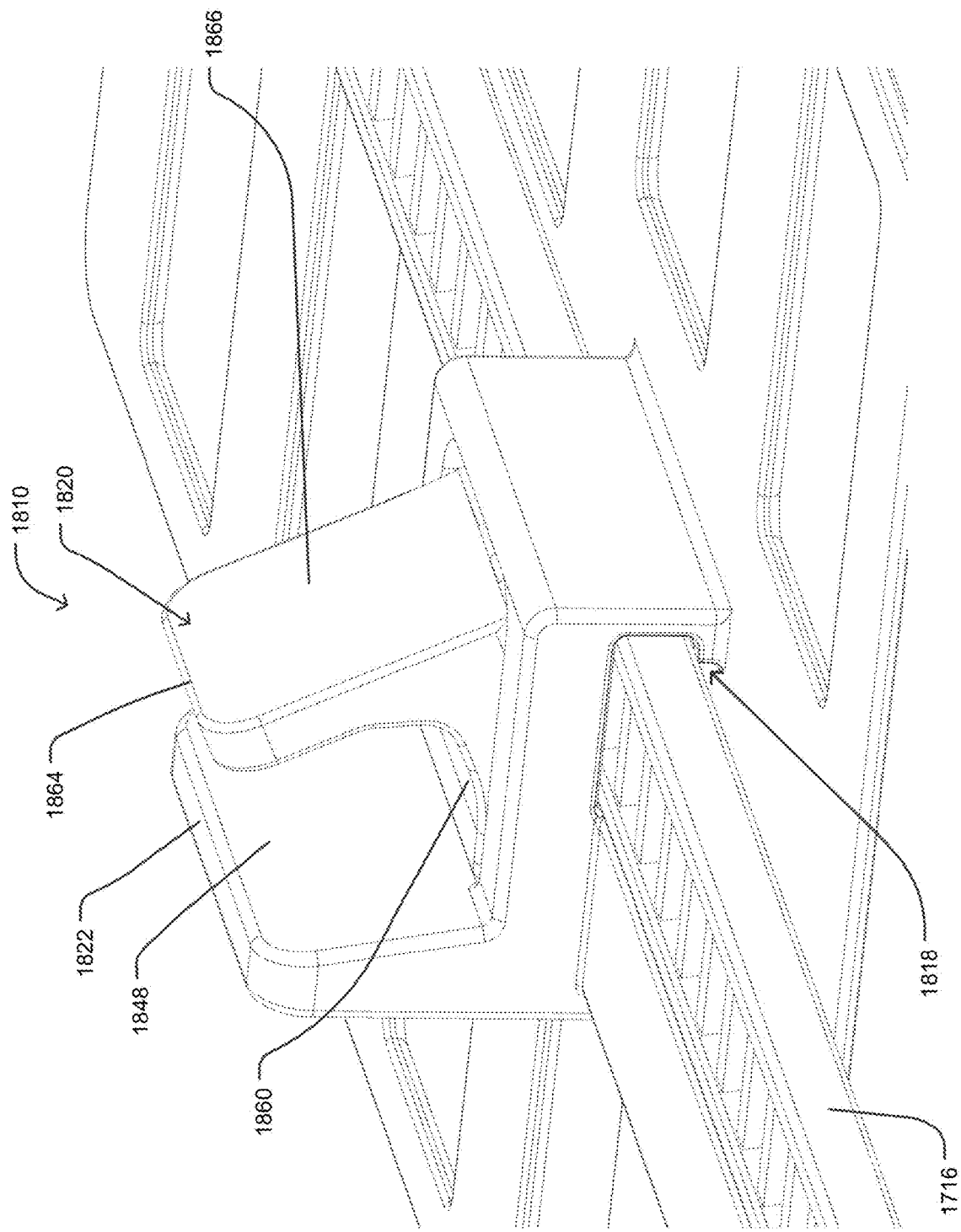
FIG. 35 is a detailed perspective view of an embodiment of the strap tie assembly of FIG. 32 in which an engagement member has been rotated to disengage a strap.

Referring further to FIG. 34, in some embodiments, the second body 1812 includes a second strap wall 1842 from which the second strap 1816 extends. The second strap wall 1842 can be positioned between the second engagement member 1820 and the second strap 1816 (e.g., outside of the second engagement member 1820). The second strap wall 1842 can define a portion of the second receiving channel 1818. The second strap wall 1842 can extend into an inner edge 1844 of the second sidewall 1822. The second body 1812 can also include additional sidewalls 1840, 1846, such that the second sidewall 1822, sidewalls 1840, 1846, and second strap wall 1842 surround at least a portion of the second engagement member 1820 (e.g., surround portion 1860 and a lower portion of the outer engagement wall adjacent to the engagement features 1872), so as to provide a barrier around the second engagement member 1820 to prevent objects from contacting the second engagement member 1820 that would disengage or otherwise disrupt the engagement between the second engagement member 1820 from the first strap 1716.

Figure 39:
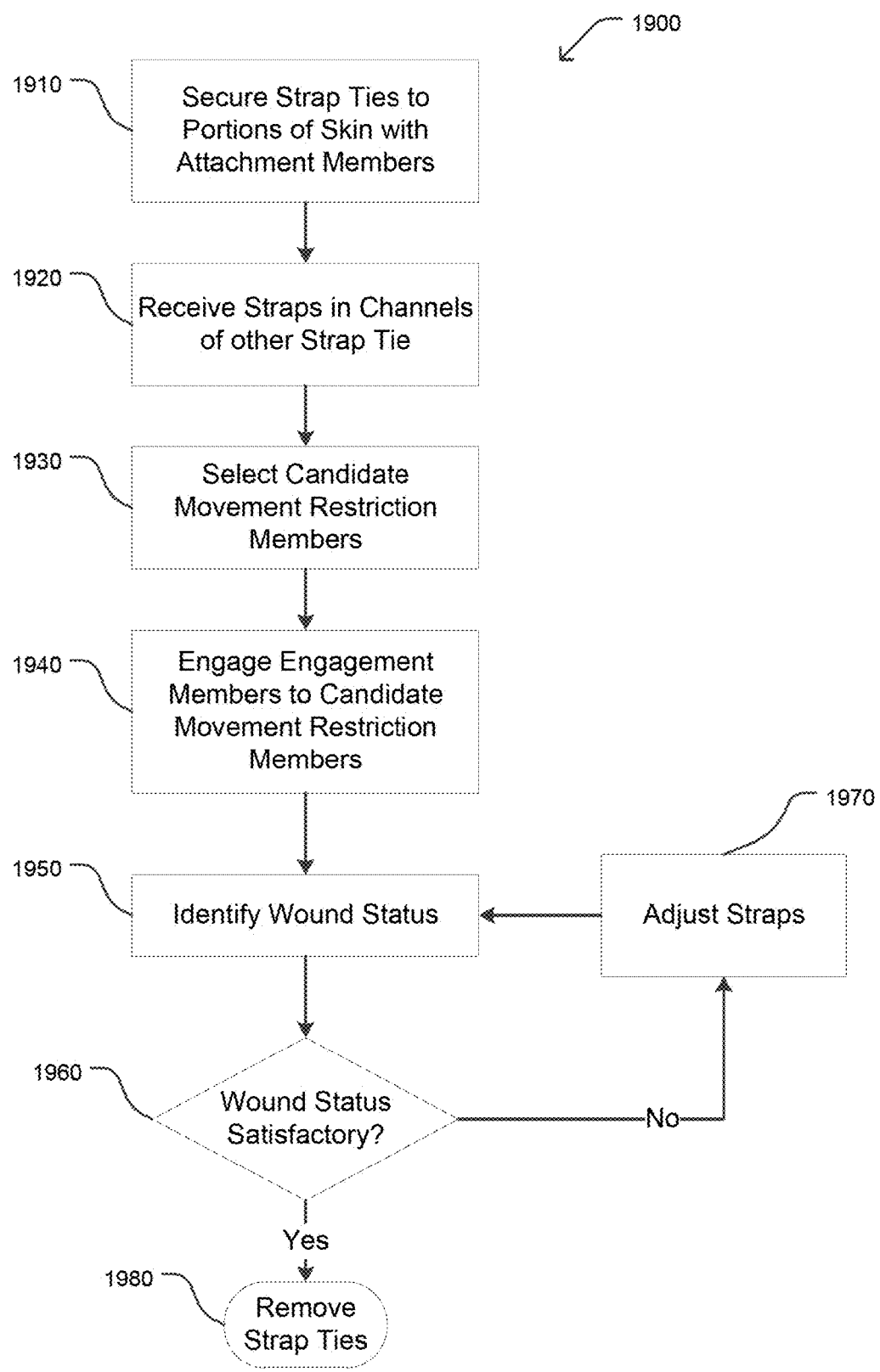
FIG. 39 is a block diagram of an embodiment of a method of securing a wound using a strap tie assembly.

Referring now to FIG. 39, a block diagram of an embodiment of a method 1900 of securing a wound using a strap tie system is shown. The method may be implemented using strap tie assemblies and devices disclosed herein, such as the strap tie assembly 1700. The method can be similar to method 1600 disclosed herein. A variety of users may perform the method, including but not limited to an individual having a wound, a medical care professional (e.g., doctor, nurse, etc.), a patient, a trauma care provider, a field care provider, a civilian, a soldier, etc.

At 1910, a first strap tie is secured adjacent to a first portion of skin on a first side of a wound, and a second strap tie is secured adjacent to a second portion of skin on a second side of the wound. The strap ties may be secured using attachment members. For example, for each strap tie, one or more attachment members (e.g., staples) can be received through selected openings of a plurality of openings of a base of the strap tie. The base can be positioned adjacent to the respective portion of skin in order to secure the strap tie to the portion of skin. In some embodiments, the base includes an adhesive surface that is positioned adjacent to the portion of skin. In some embodiments, a cover member is removed from the adhesive surface to expose the adhesive surface to attach the base to the portion of skin. In various embodiments, various numbers of attachment members can be received at the bases through the pluralities of openings secure the respective bases to the respective portions of skin. In some embodiments, a user can secure the first strap tie adjacent to the first portion of skin on the first side of the wound, and a user can secure the second strap tie adjacent to the second portion of skin on the second side of the wound.

At 1920, each strap tie receives a strap from the other strap tie. For example, the first strap tie receives a second strap from the second strap tie, through a first receiving channel in a first body of the first strap tie, and the second strap tie receives a first strap from the first strap tie, through a second receiving channel in a second body of the second strap tie. In some embodiments, a user can receive the second strap from the second strap tie through the first receiving channel in the first body of the first strap tie by drawing (e.g., pulling, threading, pushing, etc.) the second strap through the first receiving channel. Similarly, a user can receive the first strap from the first strap tie through the second receiving channel in the second body of the second strap tie by drawing the second strap through the second receiving channel.

At 1930, candidate movement restriction members are selected for engaging with engagement members of each tie strap. For example, a first candidate movement restriction member disposed along a surface of the first strap is selected, in order to be engaged by a second engagement member of the second strap tie. Similarly, a second candidate movement restriction member disposed along a surface of the second strap is selected, in order to be engaged by a first engagement member of the first strap tie. The candidate restriction members may be selected in order to apply an even amount of force across the wound. The candidate restriction members may be selected in order to draw each strap a certain distance through an opening of the other strap. The candidate restriction members may be selected based on an effect on the portions of skin or on the wound, such as a distance between the portions of skin as the wound is closed, etc. In some embodiments, a user can select the first candidate restriction member for the first strap, and a user can select the second candidate restriction member for the second strap.

At 1940, the engagement members are engaged to the respective candidate movement restriction members. For example, the first engagement member of the first strap tie is engaged to the second candidate movement restriction member, and the second engagement member of the second strap tie is engaged to the first candidate movement restriction member. Engagement members and movement restriction members may be engaged by drawing the straps a certain distance through respective openings of the strap ties until the engagement members are aligned with/engage the appropriate movement restriction member. In some embodiments, performing the engagement includes rotating an engagement member about its respective rotational axis, for example, to position an engagement feature of the engagement member adjacent to the corresponding candidate movement restriction member. A user can engage the first engagement member to the second candidate movement restriction member by aligning the first engagement member with the second candidate movement restriction member and engaging, joining, attaching, or otherwise coupling the first engagement member and the second candidate movement restriction member. A user can engage the second engagement member to the first candidate movement restriction member by aligning the second engagement member with the first candidate movement restriction member and engaging, joining, attaching, or otherwise coupling the second engagement member and the first candidate movement restriction member. A user can rotate the first engagement member and/or the second engagement member about its respective rotational axis to engage or disengage the engagement member from the corresponding strap.

At 1950, a wound status is identified. The wound status may relate to various qualities and properties of the wound, including but not limited to the health of the wound, the presence of any infections in the wound, the size of the wound (e.g., the distance between the first portion of skin on one side of the wound and the second portion of skin on the other side of the wound, etc.), any relative changes in the wound, the structural integrity of the wound (including inflation), the elasticity of the wound, tissue, or skin, etc. A user may identify the wound status, such as by observing the wound, using a sensor or other medical device to non-invasively identify properties of the wound, performing a test on the wound or material within the wound, measuring visible properties of the wound, etc.

At 1960, a determination is made as to whether the wound status is satisfactory. For example, the wound status may be satisfactory if the wound is healing properly. The wound status may be unsatisfactory if the wound is infected, if the portions of skin on either side of the wound need to be drawn more closely together, if the force applied across the wound is not even, etc. A user may determine whether the wound status is satisfactory by comparing the wound status to a heuristic, a flow chart, or any other plan or strategy relevant to wound closure and wound healing.

If the wound status is not satisfactory (e.g., unsatisfactory), then at 1970, the straps are adjusted to alter the positions of the strap ties and thus the portions of skin disposed on either side of the wound. In some embodiments, the wound status is not satisfactory because the force applied across the wound is not even. As such, at least one of the straps may be adjusted (e.g., drawn further through a channel of the other strap tie) in order to ensure that the force applied across the wound is even. A strap may be adjusted by grasping a portion of the strap (e.g., a distal end, etc.), and drawing the strap further (e.g., in a direction other than a direction in which the strap would be decoupled from the other strap tie) through the opening of the other strap tie. A strap may be adjusting by rotating the corresponding engagement member away from the strap in order to disengage the engagement member from the strap. A user may adjust the positions of one or more strap ties by holding or otherwise grasping the strap of the strap tie, and drawing the strap further through the corresponding opening until a desired position is reached, such as a position at which the force applied across the wound is even. A user may disengage the engagement member from the strap by rotating the engagement member about its rotational axis.

If the wound status is satisfactory, then at 1980, the strap tie assembly may be removed (e.g., unsecured, desecured, etc.). For example, attachment members may be removed from the portions of skin on either side of the wound. A user may remove the attachment members manually, by using a tool for removing the attachment members, etc.

While the present disclosure illustrates applications of a strap tie assembly for securing a wound, in various embodiments, a strap tie assembly may be used for various purposes, such as securing surfaces. For example, a strap tie assembly includes a first strap tie including a first base, a first body, and a first strap extending from the first body. The first base is configured to be disposed adjacent to a first surface. The first body includes a first opening and a first engagement member disposed within the first opening. The first strap includes a first proximal end attached to the first body, a first distal end opposite the first proximal end, and a plurality of first movement restriction members disposed along a surface of the first strap. The strap tie assembly also includes a second strap tie including a second base, a second body, and a second strap extending from the second body. The second base is configured to be disposed adjacent to a second surface. The second body includes a second opening and a second engagement member disposed within the second opening. The second strap includes a second proximal end attached to the second body, a second distal end opposite the second proximal end, and a plurality of second movement restriction members disposed along a surface of the second strap. The first opening is configured to receive the second strap, and the first engagement member is configured to engage one of the plurality of second movement restriction members of the second strap to prevent translation of the second strap away from the first body. The second opening is configured to receive the first strap, and the second engagement member is configured to engage one of the plurality of first movement restriction members of the first strap to prevent translation of the first strap away from the second body.

Referring generally to FIGS. 40-53, various implementations of strap tie assemblies configured to swivel, pivot, or rotate (e.g., rotate in a direction perpendicular to a portion of skin) are shown. In some applications, wound closure or healing may occur in a manner which is complicated by the tension provided across the wound by existing strap tie systems when the skin moves due to natural healing or adjustments made to the strap tie by a surgeon or other operator. To improve wound healing and reduce scarring, strap ties may be configured to swivel, so that skin edges to which the strap ties are secured may be drawn together by tension from the strap tie assemblies in a more even manner, because the direction of the tension force applied to the skin will not be inadvertently affected by changes in the orientation or growth of the skin or adjustments to other strap ties.

Referring now to FIGS. 40-47, a strap tie assembly 2000 is shown. The strap tie assembly 2000 is similar in structure and function to the various strap tie assemblies disclosed herein, including strap tie assembly 1700 shown in FIGS. 32-38B.

In some embodiments, the strap tie assembly 2000 includes a first strap tie 2010 and a second strap tie 2110. The first strap tie 2010 includes a first strap body 2012. The first strap body 2012 is configured to be coupled to a first base 2050. The first strap body 2012 can be removably and/or rotatably coupled to the first base 2050. For example, the first strap body 2012 may maintain an orientation relative to a remote strap tie (e.g., strap tie 2110) independent of movement of the first base 2050 relative to the first strap body 2012 while the first strap body 2012 is coupled to the first base 2050. In some such embodiments, the first strap body 2012 may maintain an orientation relative to a remote strap tie responsive to a change in position of skin to which the first base 2050 is attached. Such changes in skin position may result from natural healing and wound closure, or from adjustments to the strap tie 2010 or other strap ties (which may not be received by the strap tie 2010) for treating a wound, such as by a surgeon or other operator. As compared to existing systems, which may cause uneven or less controlled wound closure, the strap ties of the strap tie assembly 2000 may swivel or pivot when the underlying skin moves (e.g., when the underlying skin grows or shifts due to wound healing, or is moved due to adjustments to various strap ties), which can improve the effectiveness of the wound closure.

Figure 40:
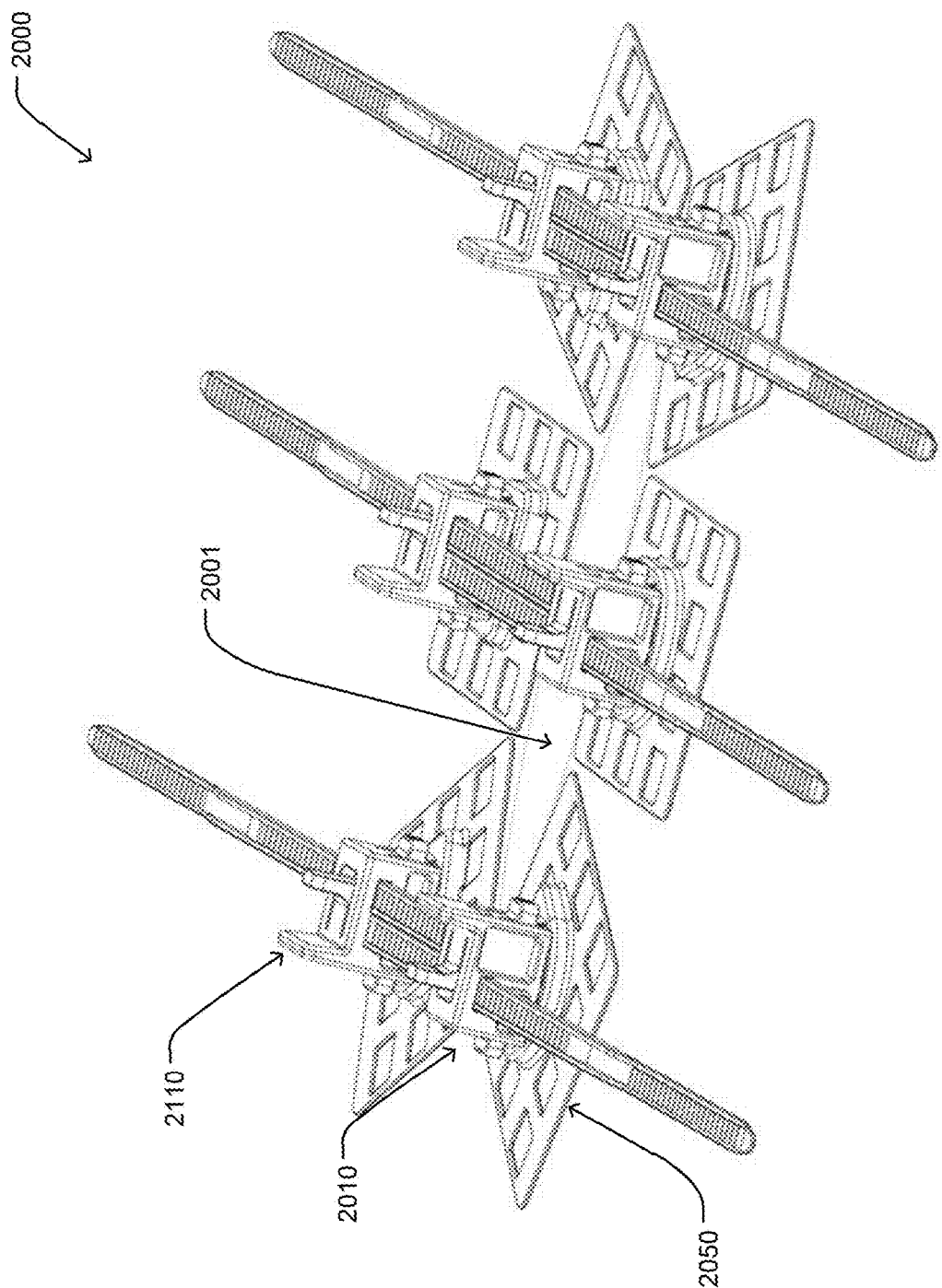
FIG. 40 is a perspective view of an embodiment of a strap tie assembly in which strap ties are configured to rotate with respect to bases.

As shown in FIG. 40, the strap tie assembly 2000 can include a plurality of strap ties (e.g., strap ties 2010, 2110) arranged about a wound 2001. Each strap tie may receive a strap from a remote strap tie, such as to apply a tension force between a first portion of skin on a first side of the wound 2001 and a second portion of skin on a second side of the wound 2001 opposite the first side. A plurality of strap ties may be secured to each side of the wound 2001. As will be described herein, the strap tie 2010 can be configured to rotate, swivel, or pivot relative to bases (e.g., first base 2050), such as due to changes in skin position resulting from adjustments to various strap ties, including strap ties not directly attached to or received by the strap tie 2010, which may facilitate improved wound closure and healing.

In some embodiments, the strap tie assembly 2000 includes a second strap tie 2110 (e.g., a remote strap tie). The second strap tie 2110 can be identical to the first strap tie 2010, such as to facilitate ease of manipulation of the strap ties 2010, 2110.

Figure 41:
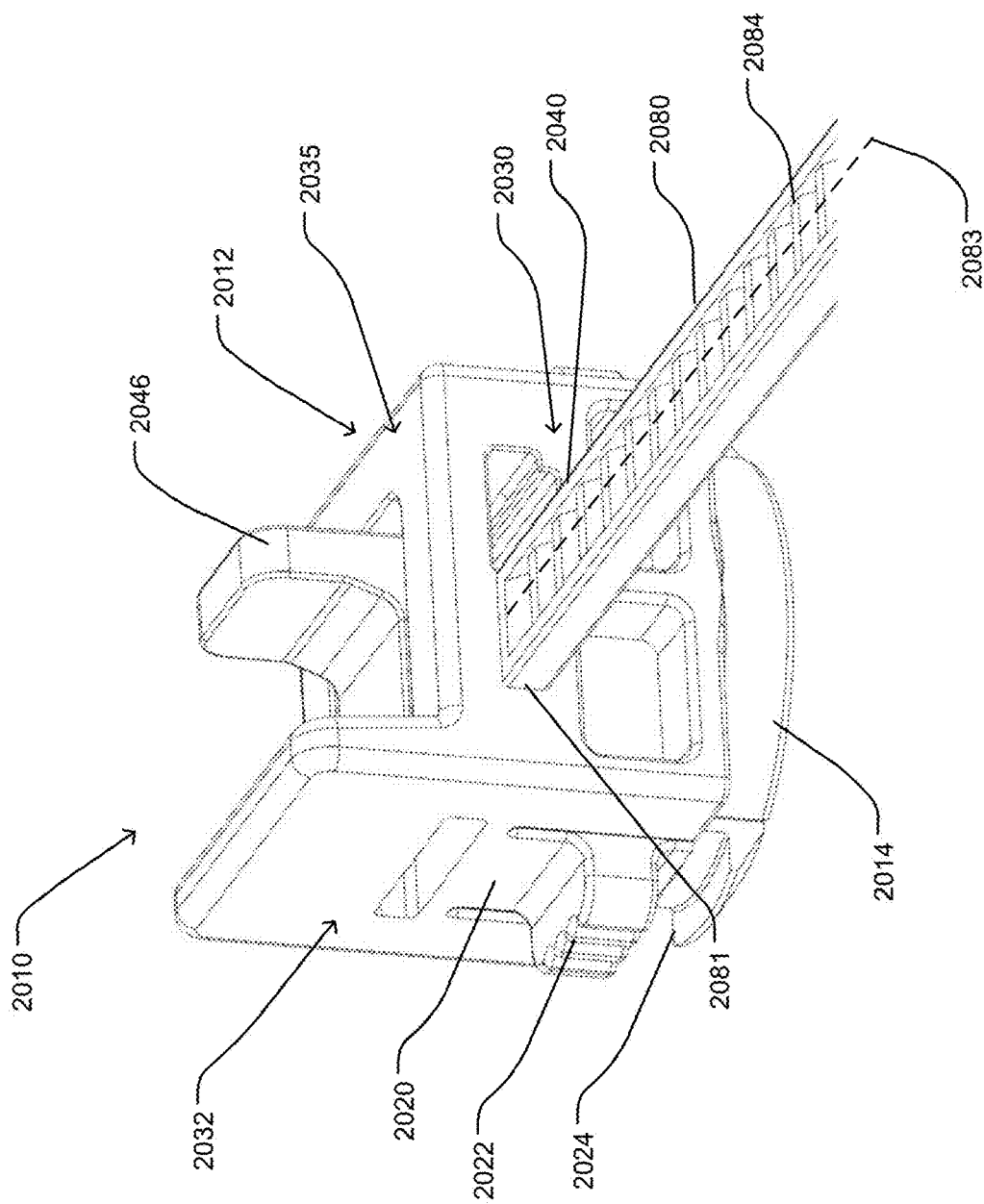
FIG. 41 is a detailed front left perspective view of a strap tie of the strap tie assembly of FIG. 40.
Figure 42:
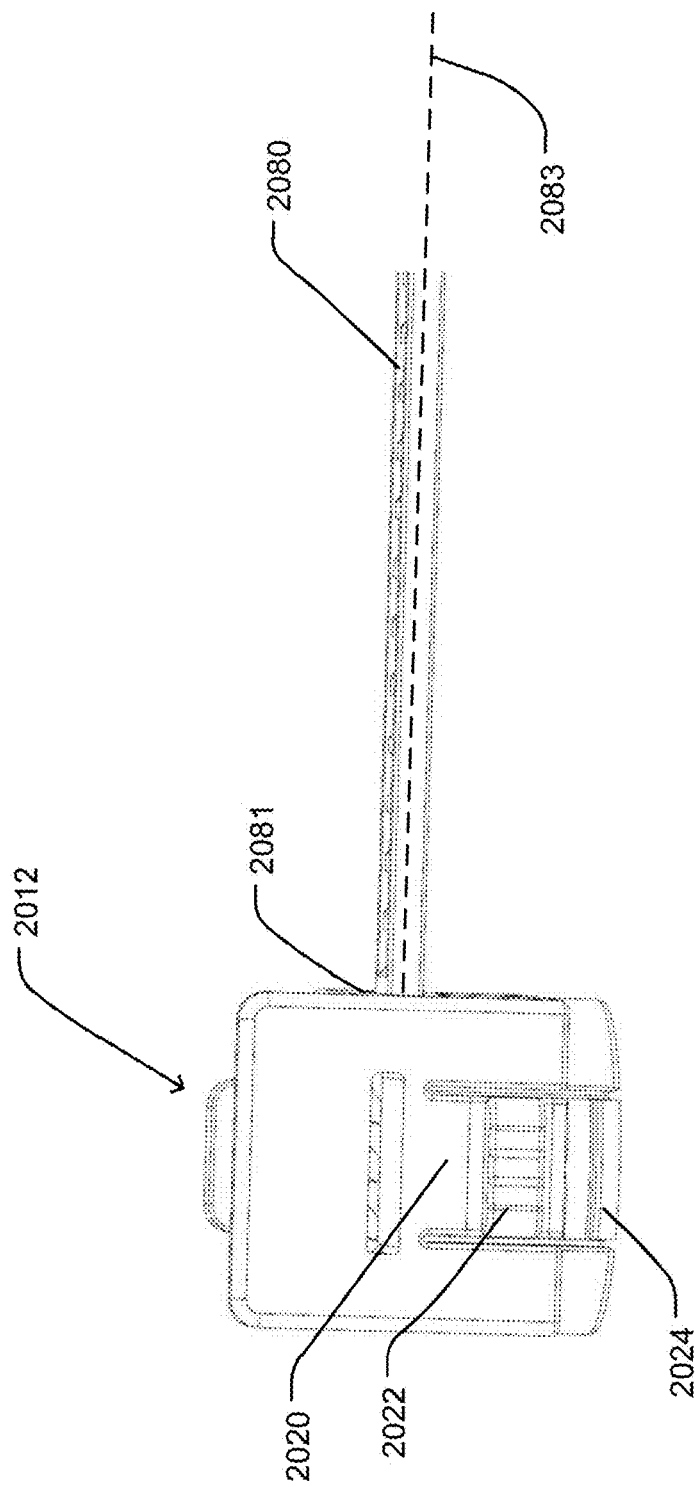
FIG. 42 is a side view of the strap tie of the strap tie assembly of FIG. 40.
Figure 43:
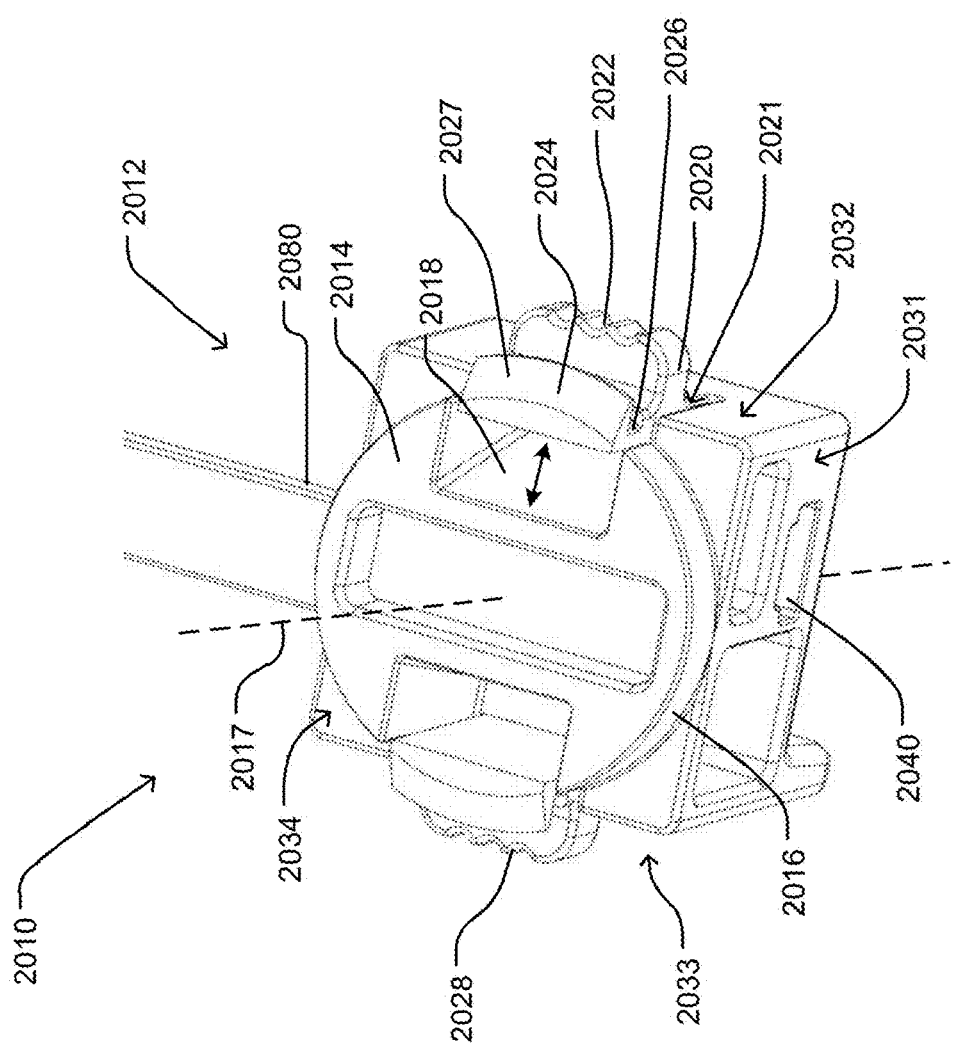
FIG. 43 is a detailed bottom right perspective view of the strap tie of the strap tie assembly of FIG. 40.
Figure 44:
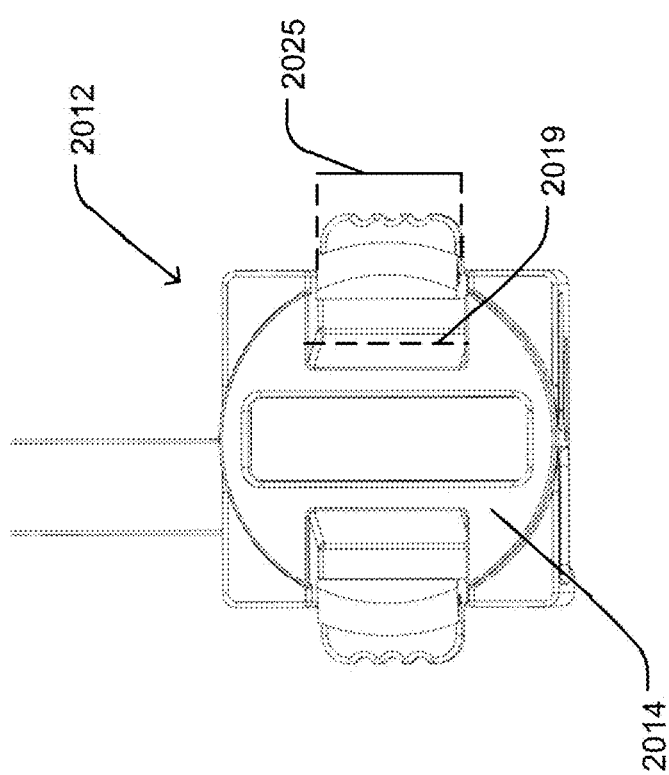
FIG. 44 is a bottom view of the strap tie of the strap tie assembly of FIG. 40.

In some embodiments, the strap tie body 2012 can include several surface body portions. For example, as shown in FIGS. 41 and 43, the strap tie body 2012 can have a generally rectangular prism shape including a first body surface portion 2030, a second body surface portion 2031, a third body surface portion 2032, a fourth body surface portion 2033, a fifth body surface portion 2034, and a sixth body surface portion 2035. In various embodiments, the strap tie body 2012 may have various shapes (and corresponding surface body portions). For example, the strap tie body 2012 may have a cylindrical or spherical shape.

Similar to the first body 1712, the first strap body 2012 includes a receiving channel 2040 and an engagement member 2046. The receiving channel 2040 extends through the strap tie body 2010 (e.g., from first surface body portion 2030 to second surface body portion 2032). The receiving channel 2040 is configured to receive a remote strap of a remote strap tie (e.g., strap tie 2110). The engagement member 2046 is configured to engage a movement restriction member of the remote strap, such as to prevent translation of the remote strap away from the first strap body 2012.

The first strap tie 2010 includes a first strap 2080. The first strap 2080 is similar to the first strap 1716. The first strap 2080 includes a first proximal end 2081 attached to the first strap body 2012 and a first distal end 2082 opposite the first proximal end 2081. The first strap 2080 includes a plurality of movement restriction members 2084, which may extend along a length of the first strap 2080 from the first proximal end 2081 to the first distal end 2082. The first strap 2080 and/or the plurality of movement restriction members 2084 can define a longitudinal axis 2083 extending along the first strap 2080.

In some embodiments, the first strap tie 2010 includes a rotational element 2014. The rotational element 2014 is configured to be rotatably (e.g., swivelingly, pivotably) coupled to the first base 2050. For example, the rotational element 2014 can be configured to rotate within or about a feature of the first base 2050. The rotational element 2014 can be configured to rotate abut a rotational axis 2017, which may be defined to be perpendicular to a plane passing through the rotational element 2014 and through a center of the rotational element 2014. In some implementations, the first strap tie 2010 may be coupled to a remote strap tie (e.g., strap tie 2110), which may restrict movement of the first strap tie 2010, such as by applying a tension force along the remote strap tie to restrict movement of the first strap body 2012, including restricting rotation of the first strap body 2012. Because the first strap tie 2010 is configured to be rotatably coupled to the first base 2050 (and thus skin adjacent to which the first base 2050 is disposed), the first strap tie 2010 may rotate freely or independently of changes in position or orientation of the skin.

Figure 45:
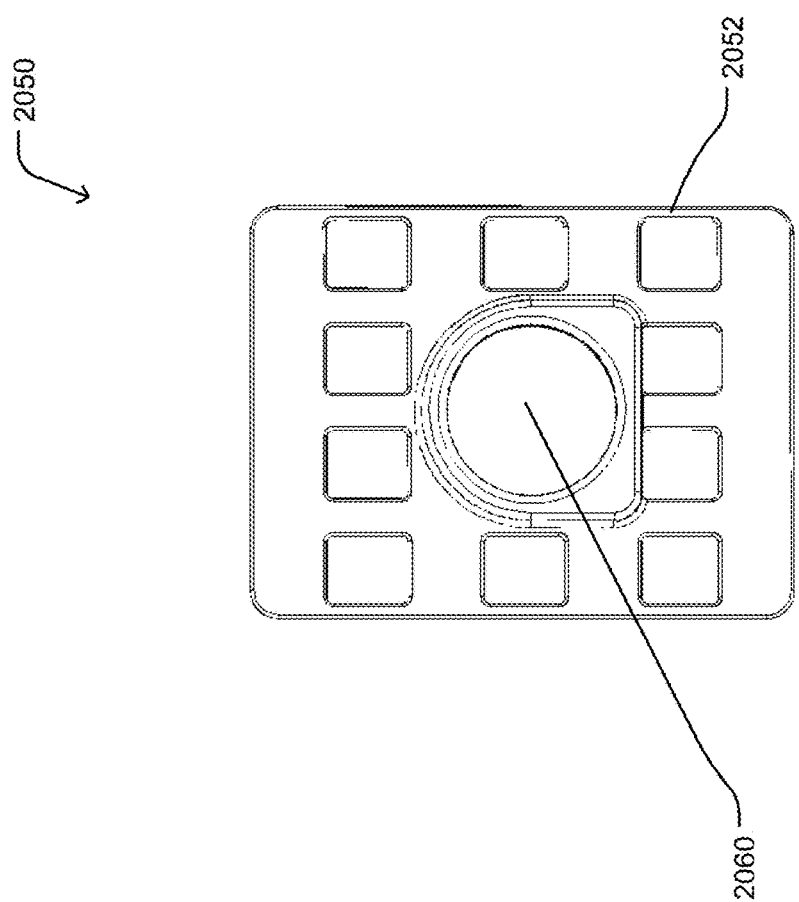
FIG. 45 is a top view of a base of the strap tie assembly of FIG. 40.
Figure 46:
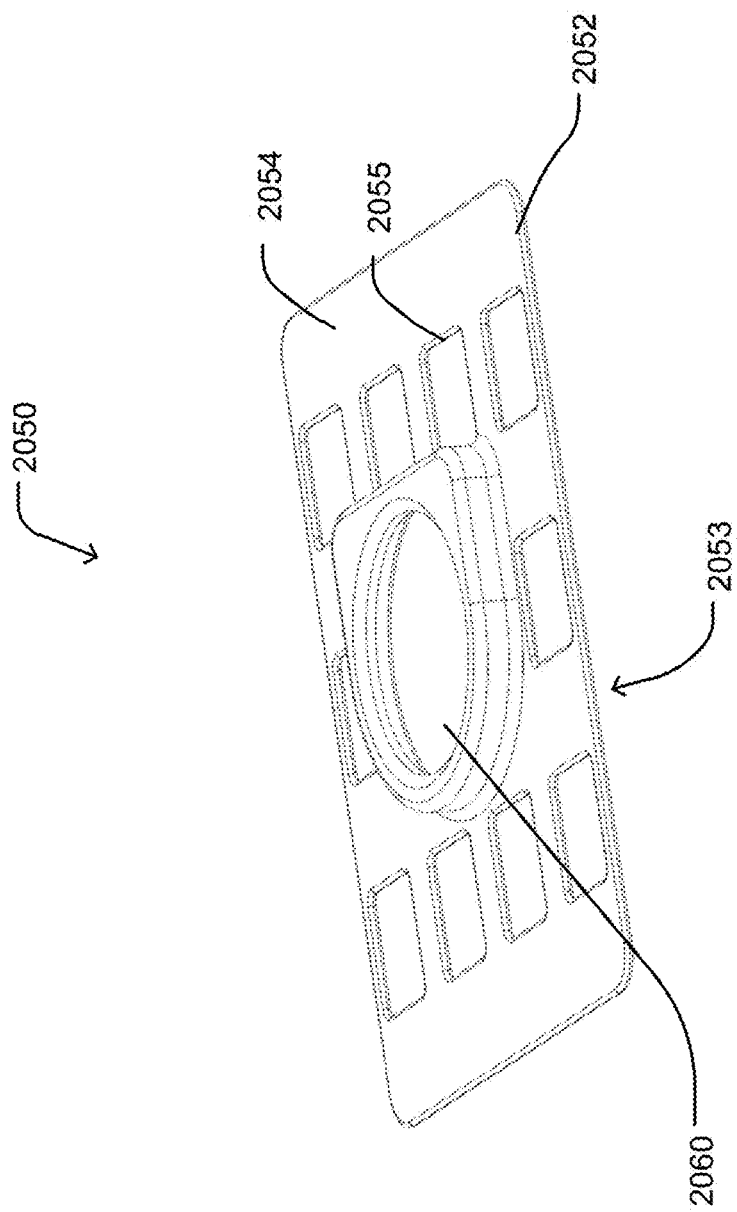
FIG. 46 is a perspective view of the base of the strap tie assembly of FIG. 40.
Figure 47:
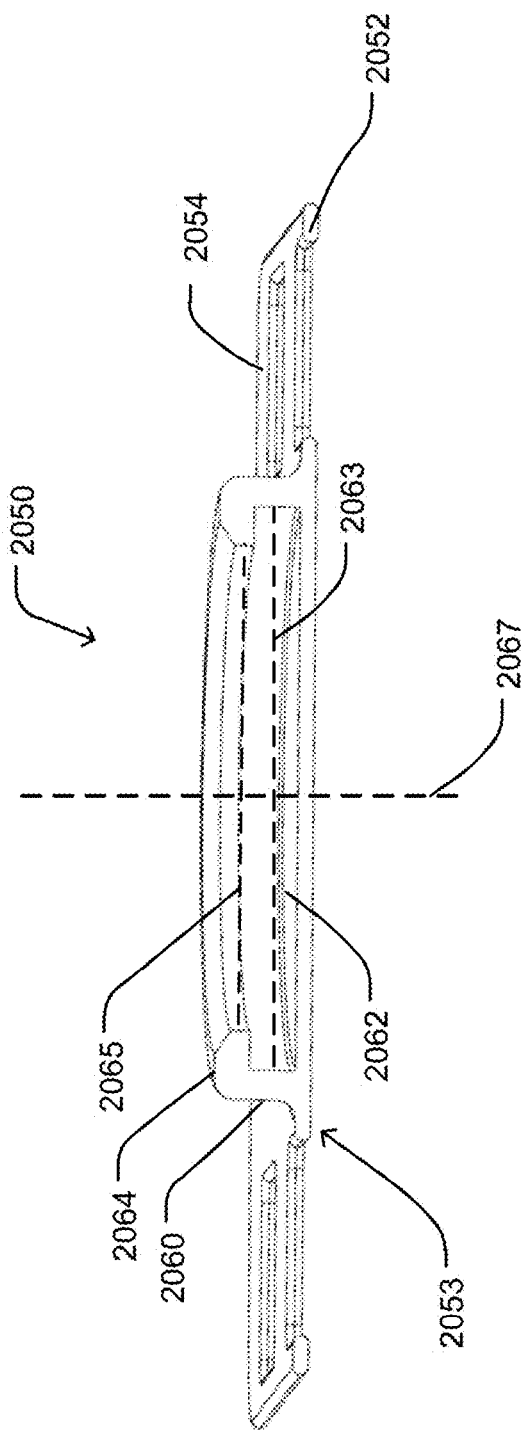
FIG. 47 is a cross-section view of the base of the strap tie assembly of FIG. 40.

Referring further to FIGS. 45-47, the first base 2050 can be similar to the first base 1714. The first base 2050 includes a first base component 2052 configured to be disposed adjacent to a portion of skin (e.g., skin near wound 2001 as shown in FIG. 39). The first base component 2052 can include a first base side 2053 to be disposed adjacent to the skin and a second base side 2054 opposite the first base side 2053. The first base 2050 includes a first body coupler 2060. The first body coupler 2060 can be coupled to the first base 2050 on the second base side 2054. The first body coupler 2060 can extend from the first base 2050.

In some embodiments, the first rotational element 2014 is configured to be removably coupled to the first base 2050, such as to allow the first strap tie 2010 to rotate relative to the first base 2050. For example, the first rotational element 2014 can be coupled to the first body coupler 2060 of the first base 2050. In some embodiments, the first body coupler 2060 includes a first cavity 2062 and a first coupler edge 2064. The first cavity 2062 defines a first diameter 2063. The first coupler edge 2064 defines a second diameter 2065 less than the first diameter 2063. The first cavity 2062 can be configured to receive the rotational element 2014. The first cavity 2062 can define a rotational axis 2067 about which the rotational element 2014 can rotate when received by the first cavity 2062 (e.g., a rotational axis 2067 perpendicular to the first base side 2053). It will be appreciated that when the rotational element 2014 is coupled to the first body coupler 2060, the rotational axis 2017 of the rotational element 2014 may align with the rotational axis 2067 such that the rotational element 2014 rotates about the rotational axis 2067.

Referring further to FIGS. 41-44, the first rotational element 2014 can be coupled to the first body coupler 2060. For example, the first rotational element 2014 may be sized to fit within the first cavity 2062. The first rotational element 2014 may include an outer wall 2016 defining the slot 2018. The outer wall 2016 may be circular, such as to facilitate rotation of the first rotational element 2014 within the first cavity 2062 (e.g., if the diameter of the outer wall 2016 is equal to the first diameter 2063 or equal to the first diameter 2063 minus a threshold diameter difference). The outer wall 2016 may have a smooth surface having a coefficient of friction less than a threshold coefficient such that the rotational element 2014 may rotate while in contact with the first cavity 2062 responsive to forces applied to the rotational element 2014 by the various skin adjustments described herein.

While FIGS. 41-44 illustrate the rotational element 2014 as being attached to and extending outward from the fourth surface 2033, it will be appreciated that in various embodiments, the rotational element 2014 may have various geometries. For example, the rotational element 2014 may include a cavity defined within the fourth surface 2033. The rotational element 2014 may extend outward from the fourth surface 2033 and define a cavity within which the first body coupler 2060 can be received (as opposed to the embodiments illustrated in FIGS. 41-47, in which the rotational element 2014 is received within the first body coupler 2060). The rotational element 2014 may be configured to engage an outer surface of a body coupler (e.g., a body coupler similar to first body coupler 2060 and having a lip or cavity on an outer edge to receive an engagement feature associated with the rotational element 2014).

As described above, the rotational element 2014 defines the first slot 2018. The first slot 2018 can define a first slot width 2019. The first slot 2018 can be defined within the rotational element 2014, e.g., extending into the rotational element 2014.

In some embodiments, the first strap body 2012 includes a first base engagement member 2020. The first base engagement member 2020 can be configured to engage (e.g., attach, secure, couple) the rotational element 2014 of the first strap body 2012 to the first base 2050 (e.g., to the first body coupler 2060 of the first base 2050). The first base engagement member 2020 can be configured to removably (e.g., releasably, semi-permanently) engage the first strap body 2012 to the first base 2050.

In some embodiments, the first base engagement member 2020 includes a first actuator component 2022. The first actuator component 2022 can receive an actuation input (e.g., a force applied to the first actuator component 2022) and change a position of the first engagement member 2020 responsive to the actuation input. As shown in FIGS. 41-44, the first actuator component 2022 is defined along the third surface 2032 between the first surface 2030 and the second surface 2031, and extends a distance away from the third surface 2032. As such, the actuation input may be received by the first actuator component 2022 in a variety of directions (without being spatially restricted by other components of the first strap tie 2010), such as by a manipulation applied to force the first actuator component 2022 inward towards the first strap body 2012. In some embodiments, the first actuator component 2022 includes engagement features such as ridges or high friction surfaces, which may facilitate manipulation of the first actuator component 2022 (as well as identifying the first actuator component 2022 without needing to look at the first actuator component 2022).

In some embodiments, the first base engagement member 2020 includes a first engagement component 2024. The first engagement component 2024 is configured to engage the first base 2050. In some embodiments, the first engagement component 2024 is configured to be received within the first slot 2018 of the rotational element 2014. For example, the first engagement component 2024 may define a first engagement width 2025 less than the slot width 2019, such that the first engagement component 2024 is sized to fit within the slot first 2018. The first engagement component 2024 may include a first engagement wall 2026 and a first tab 2027 extending from an end of the first engagement wall 2026. The first engagement wall 2026 may define the first engagement width 2025. The first engagement wall 2026 may have a curved surface to facilitate rotation of the first strap body 2012 together with the rotational element 2014 while the first engagement component 2024 is received within the first slot 2018.

The first actuator component 2022 can be configured to be moved (e.g., responsive to receiving a force, such as an actuation input) from a first position at which the first engagement component 2024 extends a first distance away from the first slot 2018 (e.g., such that the first engagement wall 2026 extends further outward than the outer wall 2016 from a center of rotation of the rotational element 2014), to a second position at which the first engagement component 2024 extends a second distance less than the first distance away from the first slot 2018 (e.g., such that the first engagement wall 2026 extends a distance no greater than the outer wall 2016 from a center of rotational of the rotational element 2014). The first actuator component 2022 can be coupled to the first engagement component 2024 such that movement of the first actuator component 2022 results in movement of the first engagement component 2024. For example, as shown in FIG. 43, the first actuator component 2022 is integrally formed with the first engagement component 2024; however, in various embodiments, the first actuator component 2022 and first engagement component 2024 may be coupled by various mechanisms, such as linkages, cams, etc., to facilitate movement of the first engagement component 2024 responsive to movement of the first actuator component 2022. In some embodiments, the first actuator component 2022 is configured to be biased to the first position. For example, at least a portion of the first base engagement member 2020 may be made from a flexible material (e.g., rubber) configured to bias the first actuator component 2022 to the first position, which may facilitate retaining the first strap tie 2010 as being coupled to the first base 2050 unless the actuation input is received to move the first actuator component 2022. The first strap body 2012 may include a cavity (not shown) configured to at least partially receive the first base engagement member 2020 in the second position.

While FIGS. 41-44 illustrate the first actuator component 2022 as configured to be moved into or out of the first strap body 2012 responsive to the actuation input (e.g., to be moved into the first strap body 2012 to disengage the rotational element 2014 from the first base coupler 2060 as will be described below) it will be appreciated that in various embodiments, the first base engagement member 2020 can be configured to allow for various directions of movement and/or corresponding biases to enable removable coupling of the first strap tie 2010 to the first base 2050 to allow the first strap tie 2010 to rotate relative to the first base 2050. The first body coupler 2060 of the first base 2050 may be similarly configured in various embodiments to cooperate with the rotational element 2014 and the first base engagement member 2020 to engage the first strap tie 2010 to the first base 2050.

Referring further to FIGS. 43 and 47, the first engagement component 2024 can be configured to removably couple to the first body coupler 2060 of the first base 2050 responsive to movement of the first actuator component 2022. In some embodiments, such as where the first engagement component 2024 includes the tab 2027 and the first body coupler 2060 includes the first coupler edge 2064, the tab 2027 can be configured to be received within the first cavity 2062 and between the first coupler edge 2064 and the wall of the first cavity 2062 opposite the first coupler edge 2064. For example, when the first actuator component 2022 is in the first position, the first engagement component 2024 (e.g., the tab 2027 of the first engagement component 2024) may extend within the first cavity 2062 to a distance greater than the second diameter 2065 of the first coupler edge 2064 and less than the first diameter 2063 of the first cavity 2062, such that a force applied to the first strap tie 2010 perpendicular to the second diameter 2065 does not cause the rotational element 2014 to be released from the first cavity 2062 (e.g., the first coupler edge 2064 restricts movement of the rotational element 2014 in a direction perpendicular to the second diameter 2065). In some embodiments, such as where the first actuator component 2022 is biased to the first position, the first engagement component 2024 is biased to extend within the first cavity to the distance greater than the second diameter 2065.

In some embodiments, the first strap body 2012 includes or defines a second base engagement member 2028. The second base engagement member 2028 can be similar to the first engagement component 2020. The second base engagement member 2028 can be positioned on an opposite surface portion of the first strap body 2012 from the first base engagement member 2020 (e.g., on or adjacent to fourth body surface portion 2033). Locating the second base engagement member 2028 opposite the first base engagement member 2020 may facilitate simultaneous manipulation of both the first and second base engagement members (e.g., a simultaneous actuation input may be provided in which the first engagement member 2020 and second engagement member 2028 are each pushed inward into the first strap body 2012).

In some embodiments, the first base 2050 includes at least one opening 2055 extending through the first base 2050 from the first base side 2053 to the second base side 2054. Similar to the openings of the first base 1714 and various other bases described herein, the at least one opening 2055 is configured to receive a staple or suture to secure the first base 2050 to a portion of skin. The first base 2050 may include an adhesive on the first base side 2053 to secure the first base 2050 to a portion of skin.

As shown in FIG. 46, the first base 2050 may include a plurality of openings 2055, which may be arranged in a grid as shown or in various other arrangements. In some embodiments, the first body coupler 2060 may be configured to be spaced a threshold distance away from each of the openings 2055 such that a staple may be received through the openings 2055 without contacting the strap tie 2010 when coupled to the first body coupler 2060.

As shown in FIGS. 40-47, the strap tie assembly 2000 may be configured such that the rotational element 2014 (and the strap tie body 2012) rotates about the rotational axis 2017, and thus the rotational axis 2067 of the first body coupler 2060 when the rotational element 2014 is coupled to the first body coupler 2060. In various embodiments, at least one of the strap tie body 2012 or the rotational element 2014 is configured to rotate about at least two axes relative to the first body coupler 2060. For example, the rotational element 2014 may define a convex at least partially spherical shape configured to be received by a concave at least partially spherical shape of the first body coupler 2060 (or, the rotational element 2014 may define a concave at least partially spherical shape configured to receive a convex at least partially spherical shape of the first body coupler 2060). The rotational element 2014 may be configured to rotate about at least two of an x-axis, y-axis, or z-axis defined using a Cartesian coordinate system associated with the rotational element 2014 (e.g., originating at a center of rotation of the rotational element 2014). In some embodiments, the rotational element 2014 may include an at least partially spherical component coupled to a stopper component, which may restrict rotation of the rotational element 2014 to two axes (e.g., the spherical component may facilitate rotation about all three axes, while the stopper component may be disposed in an xy-plane associated with the spherical component and thus restrict rotation in at least one of an x-direction or y-direction corresponding to the xy-plane).

Figure 48:
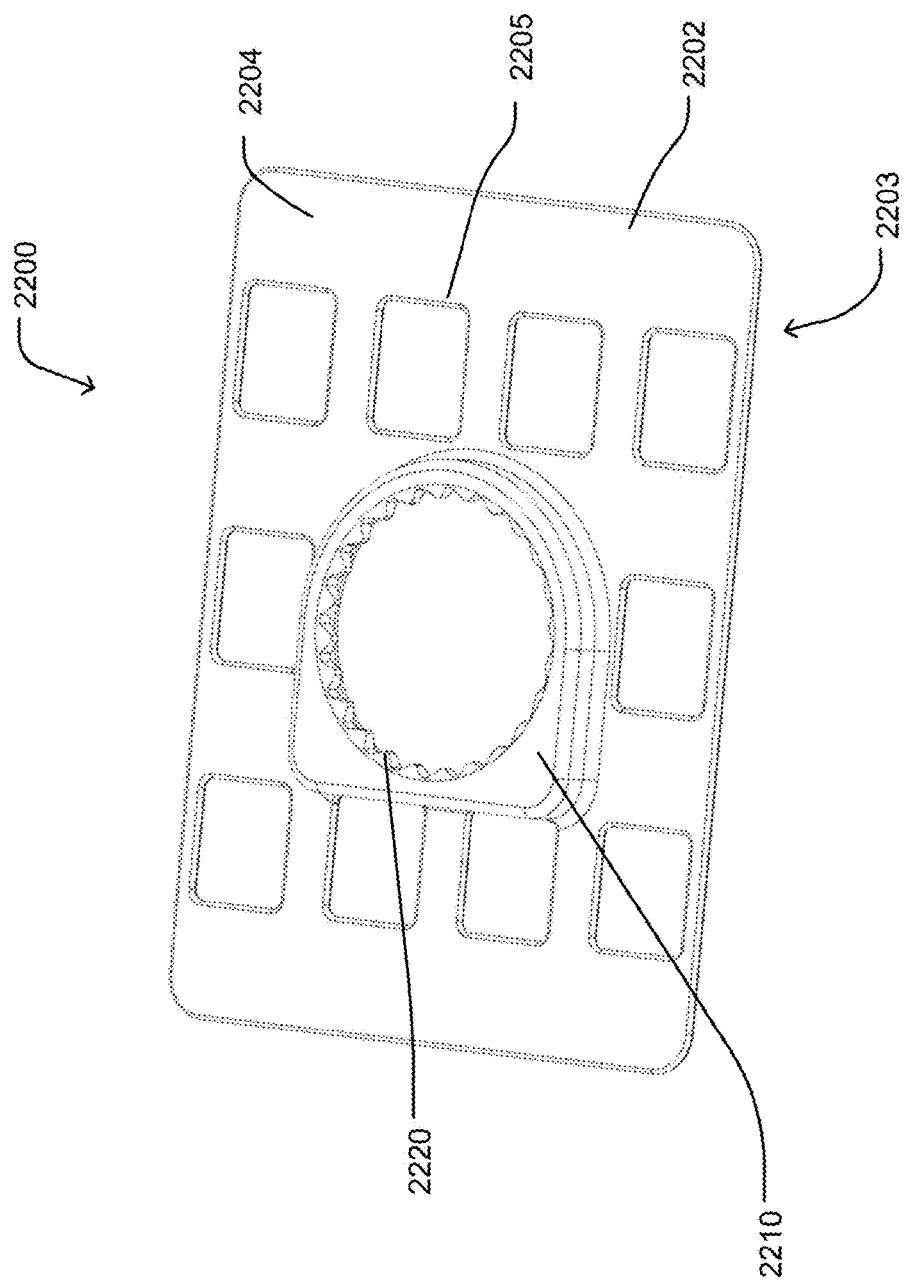
FIG. 48 is a perspective view of an embodiment of a base of a strap tie assembly including frictional engagement features.
Figure 49:
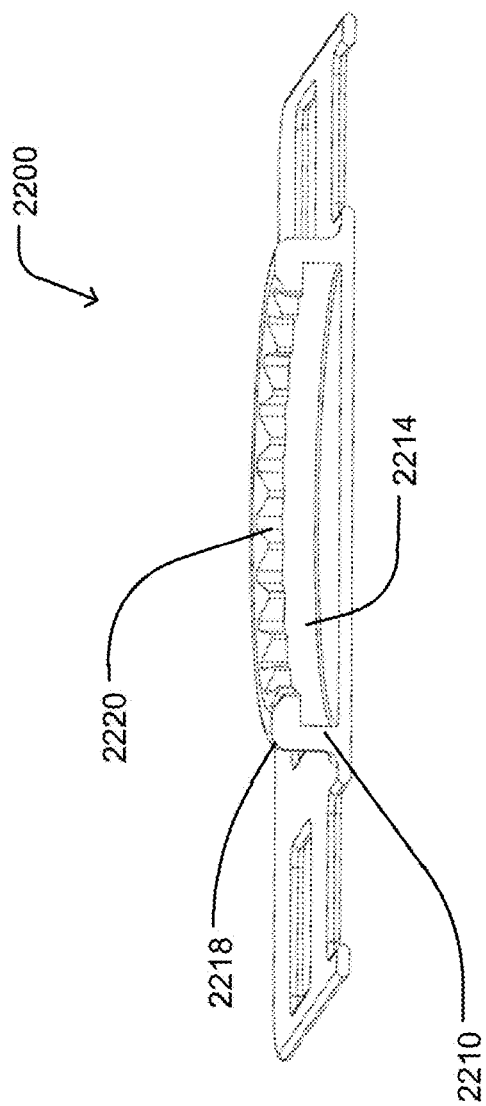
FIG. 49 is a cross-section view of the base of FIG. 48.

Referring now to FIGS. 48-49, an embodiment of a base 2200 is shown. The base 2200 is similar to the first base 2050, with the exception of the frictional engagement features described herein. As shown in FIGS. 48-49, the base 2200 includes a base component 2202 extending from a first base side 2203 to be disposed adjacent to a portion of skin to a second base side 2204 opposite the first base side, at least one opening 2205, and a body coupler 2210. The body coupler 2210 includes a cavity 2214 and a coupler edge 2218.

Similar to the first body coupler 2060, the body coupler 2210 includes a cavity 2212 and a coupler edge 2218. The coupler edge 2218 can be configured to frictionally engage a rotational element of a strap tie. In some embodiments, the rotational element is identical to the rotational element 2014 of the trap tie 2010. In some embodiments, the rotational element includes frictional elements configured to engage with the coupler edge 2218. As shown in FIGS. 48-49, the coupler edge 2218 includes a plurality of frictional engagement elements 2220 (e.g., teeth). The plurality of frictional engagement elements 2220 are configured to restrict rotation of a rotational element relative to the coupler edge 2218. In some embodiments, the plurality of frictional engagement elements 2220 are configured to ratchet (e.g., selectively permit rotation) of a rotational element in at least one of a clockwise or counter-clockwise direction. The plurality of frictional elements engagement 2220 may be configured to permit discrete rotational movements of a rotational element, which may facilitate making specific adjustments to a strap tie assembly. In some embodiments, the plurality of frictional engagement elements 2220 are configured to define a coefficient of friction with a rotational element that is greater than a first threshold coefficient at which forces associated with nominal or unintentional movements of skin adjacent to a wound (e.g., wound 2201 shown in FIG. 39) are insufficient to cause rotation against the coupler edge 2218, and less than a second threshold coefficient at which forces associated with intentional adjustments to a strap tie assembly or skin adjacent to a wound (e.g., adjustments based on forces applied by a surgeon or other user) are insufficient to cause rotation against the coupler edge 2218.

Figure 50:
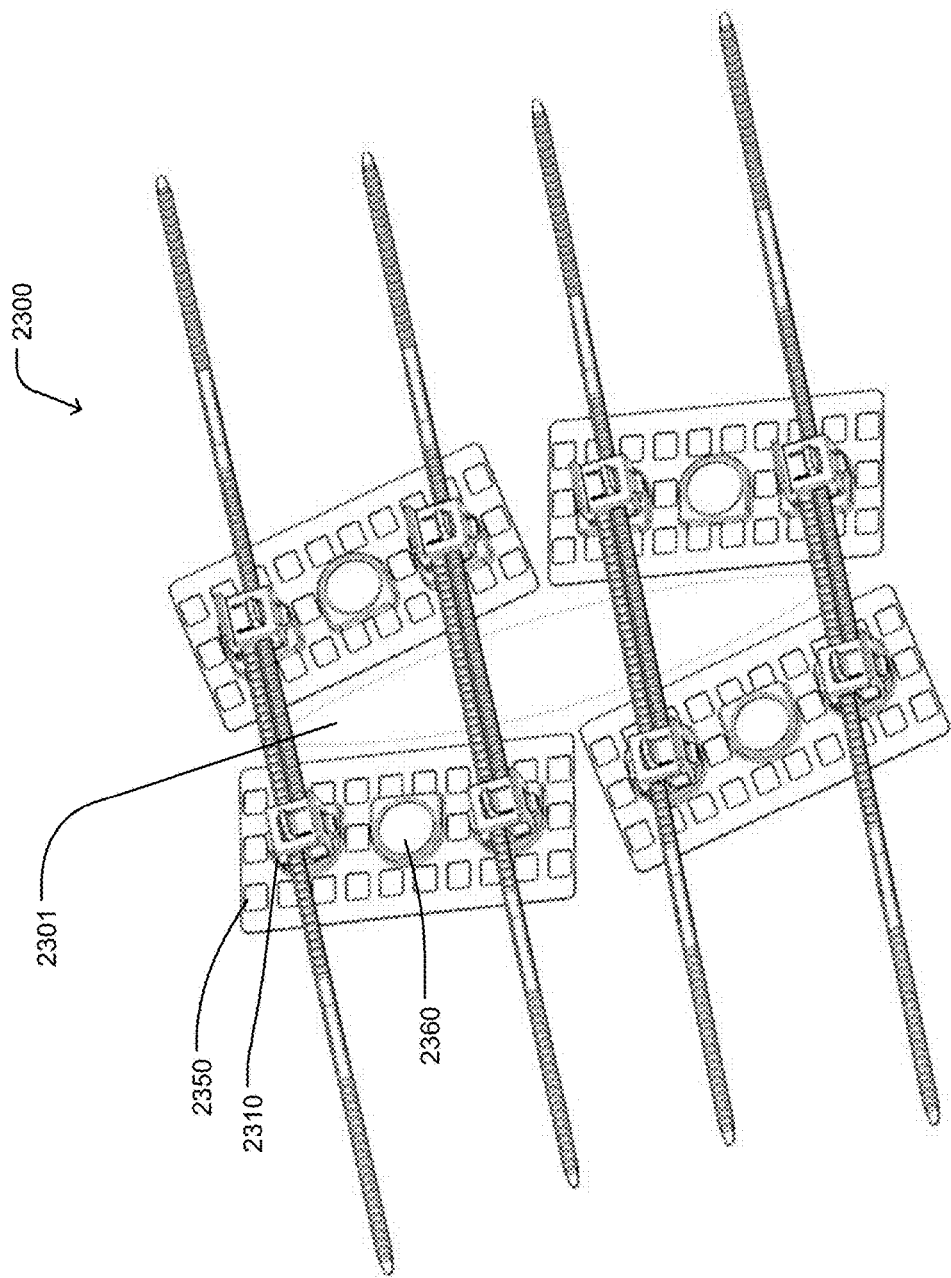
FIG. 50 is a perspective view of an embodiment of a strap tie assembly including a base including multiple body couplers.

Referring now to FIG. 50, an embodiment of a strap tie assembly 2300 is shown. The strap tie assembly 2300 can be similar to the strap tie assembly 2000 shown in FIGS. 39-47. The strap tie assembly 2300 can include one or more strap ties 2310 configured to be positioned about a wound 2301; for example, FIG. 50 illustrates four strap ties 2310 (two strap ties 2310 coupled to each of two bases 2350) on either side of the wound 2301. As shown in FIG. 50, the strap tie assembly 2300 includes a base 2350 including a plurality of body couplers 2360. The plurality of body couplers 2360 may facilitate precise selection of locations for the strap tie 2310 to be secured to the base 2350.

Figure 51:
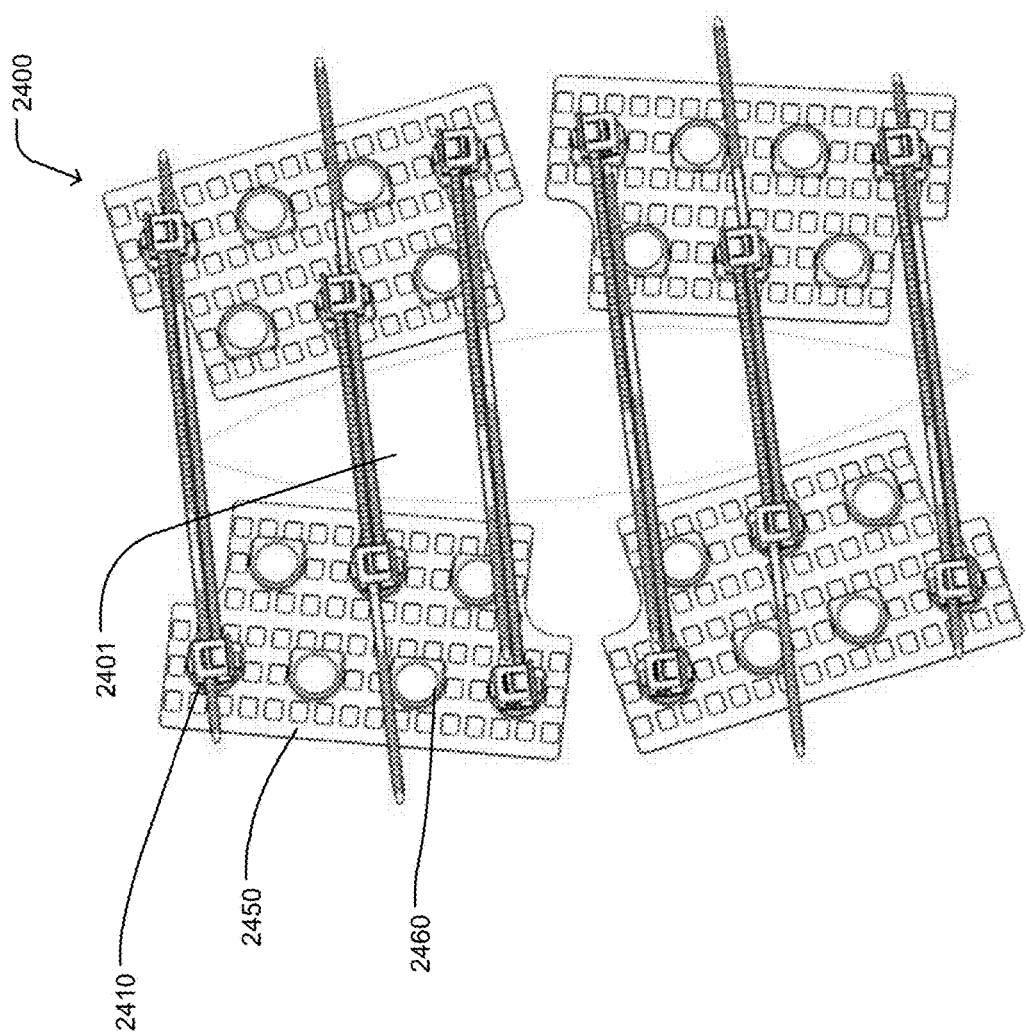
FIG. 51 is a perspective view of an embodiment of a strap tie assembly including a base including multiple body couplers arranged in staggered rows.

Referring now to FIG. 51, an embodiment of a strap tie assembly 2400 is shown. The strap tie assembly 2400 can be similar to the strap tie assemblies 2000, 2300 described above. The strap tie assembly 2400 can include one or more strap ties 2410 configured to be disposed about portions of skin adjacent to a wound 2401. The strap tie assembly 2400 includes at least one base 2450. The base 2450 can be similar to the base 2350, but includes a plurality of body couplers 2450 which are disposed in at least two rows along the base 2450. In some embodiments, as shown in FIG. 51, the rows of body couplers 2450 may be staggered (e.g., a line perpendicular to a row axis defined through the body couplers 2450 of each row does not intersect a body coupler 2450 of an adjacent row).

Figure 52:
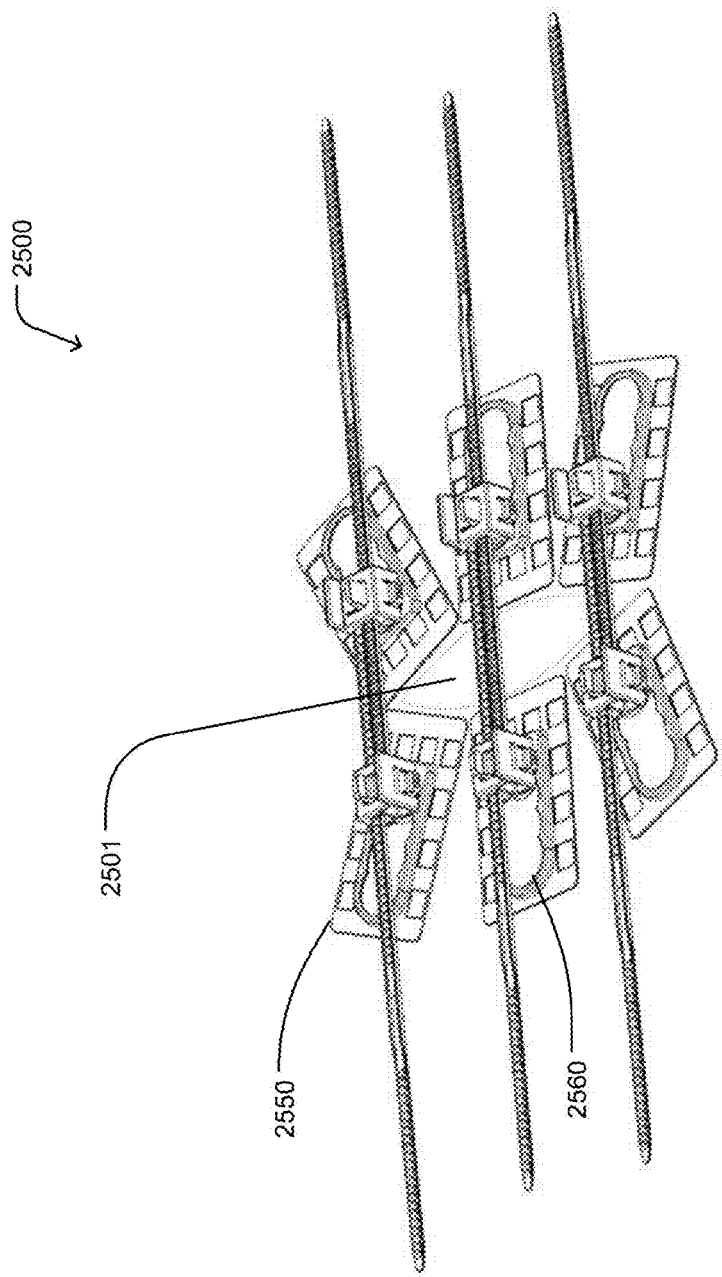
FIG. 52 is a perspective view of an embodiment of a strap tie assembly including a base including connected body couplers.
Figure 53:
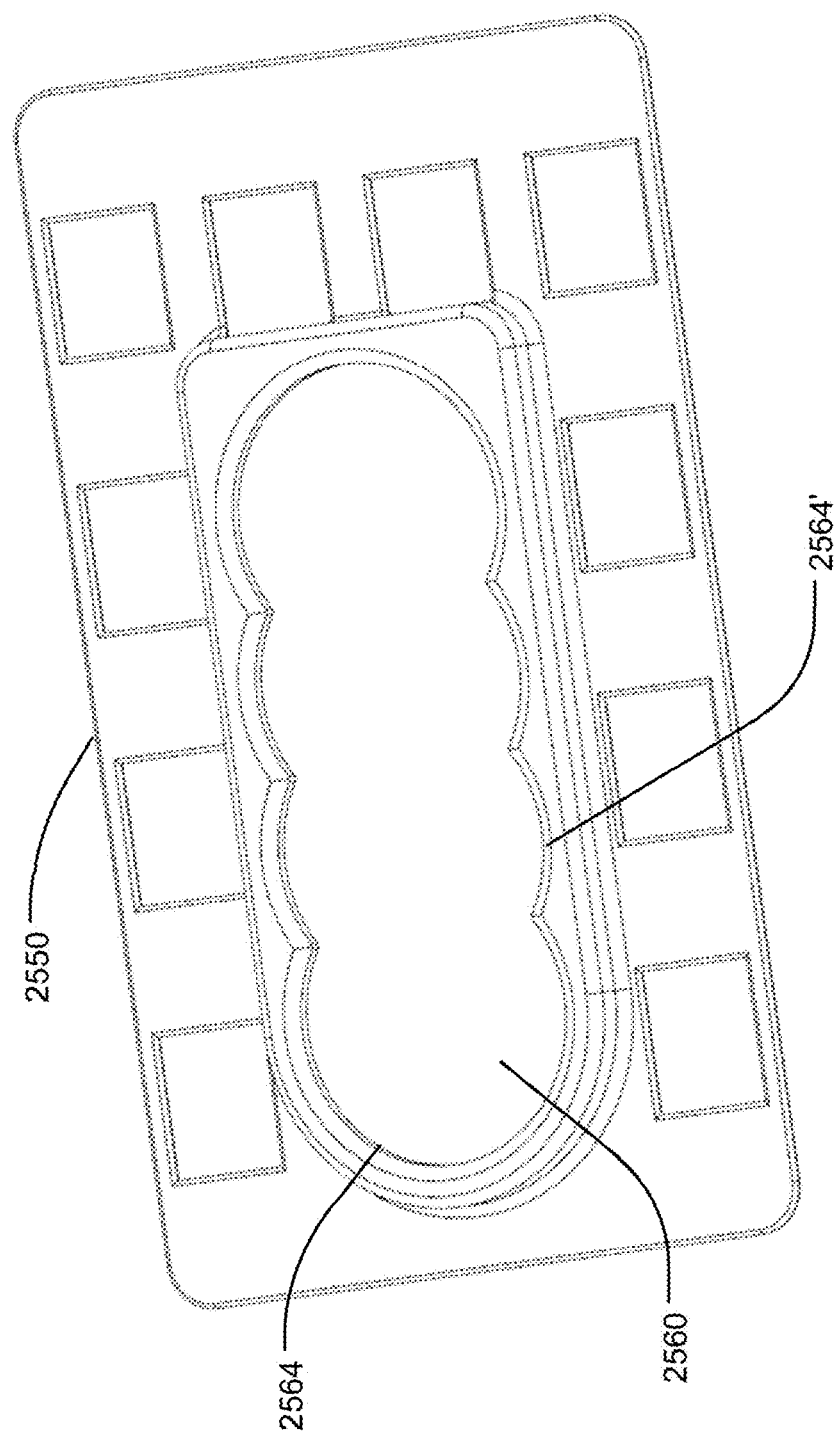
FIG. 53 is a detailed perspective view of the base of FIG. 52.

Referring now to FIGS. 52-53, a strap tie assembly 2500 is shown. The strap tie assembly 2500 can be similar to the strap tie assemblies 2000, 2300, 2400. The strap tie assembly 2500 includes a base 2550 including a plurality of body couplers 2560. Unlike the various body couplers described herein (e.g., first body coupler 2060), which may be formed to be discrete elements, the plurality of body couplers 2560 may be formed to be continuous or connected elements. For example, a first body coupler 2560 may include a first body coupler edge 2564 spaced from a first cavity 2562, and at least one second body coupler 2560 may include a second coupler edge 2564' extending from the first body coupler edge 2564. In some embodiments, the body couplers 2560 may facilitate precise or minute locating or adjustment of locations of strap ties coupled to the base 2550, which may allow for a more compact, low profile configuration of the strap tie assembly 2500.

What is claimed is:

1. A strap tie comprising:
   a body including a receiving channel, a strap engagement member, and a first base engagement member including an actuator component coupled to an engagement component, the actuator component integral to the body, the receiving channel extending through the body, the receiving channel configured to receive a remote strap, the engagement member configured to engage a movement restriction member of the remote strap to prevent translation of the remote strap away from the body;
   a strap extending from a side of the body, the strap having a thickness along the side of the body at a proximal end attached to the body, a distal end opposite the proximal end, and a plurality of movement restriction members extending along a longitudinal axis from the proximal end to the distal end; and
   a rotational element of the body configured to removably couple to a base to allow the strap tie to rotate about a rotational axis relative to the base, the rotational axis extending through the body and perpendicular to the longitudinal axis, the first base engagement member configured to removably couple the rotational element to the base responsive to actuation of the actuator component, the receiving channel extending in a direction perpendicular to the rotational axis.

2. The strap tie of claim 1, wherein:
   the rotational element defines a slot extending into the rotational element; and
   the engagement component is configured to be at least partially received in the slot, the actuator component configured to be moved from a first position at which the engagement component extends a first distance away from the slot to a second position at which the engagement component extends a second distance less than the first distance away from the slot.

3. The strap tie of claim 2, wherein the actuator component is configured to be biased to the first position.

4. The strap tie of claim 2, wherein the rotational element includes a circular wall defining the slot, the slot having a slot width, the engagement component including an engagement wall having an engagement width less than the slot width and a tab extending away from the slot, the tab configured to couple the rotational element to the base.

5. The strap tie of claim 2, further comprising a second base engagement member configured to couple the rotational element to the base, the second base engagement member on an opposite surface portion of the body from the first base engagement member.

6. The strap tie of claim 1, wherein the first engagement member is configured to be moved into a cavity defined within the body to move from a first position to a second position.

7. The strap tie of claim 1, wherein the rotational element is at least one of attached to, defined within, or extended from a first body surface portion of the body.

8. The strap tie of claim 7, wherein the strap engagement member is configured to move within a slot defined on a second body surface portion opposite the first body surface portion.

9. The strap tie of claim 1, wherein the plurality of movement restriction members define a longitudinal axis from the proximal end to the distal end, and the rotational element is disposed in a plane parallel to and spaced from the longitudinal axis.

10. A strap tie assembly, comprising:
    a base including a base component configured to be disposed adjacent to a portion of skin on a first base side of the base component and a first body coupler coupled to a second base side of the base component opposite the first base side; and
    a strap tie including
       a body including a receiving channel, a strap engagement member, and a first base engagement member including an actuator component coupled to an engagement component, the actuator component integral to the body, the receiving channel extending through the body, the receiving channel configured to receive a remote strap, the engagement member configured to engage a movement restriction member of the remote strap to prevent translation of the remote strap away from the body;
       a strap extending from a side of the body, the strap having a thickness along the side of the body at a proximal end attached to the body, a distal end opposite the proximal end, and a plurality of movement restriction members; and
       a rotational element of the body configured to removably couple to the base to allow the strap tie to rotate relative to the base about a rotational axis perpendicular to an axis through the receiving channel, the first base engagement member configured to removably couple the rotational element to the base responsive to actuation of the actuator component, the receiving channel extending in a direction perpendicular to the rotational axis.

11. The strap tie assembly of claim 10, wherein the first body coupler includes a first cavity defining a first diameter and a first coupler edge spaced from the first cavity on an opposite side of the first cavity from the base component, the first coupler edge defining a second diameter less than the first diameter.

12. The strap tie assembly of claim 11, wherein the first coupler edge defines a plurality of teeth configured to restrict rotation of the rotational element relative to the coupler edge.

13. The strap tie assembly of claim 12, wherein the rotational element defines a plurality of edge engagement members configured to engage the plurality of teeth.

14. The strap tie assembly of claim 10, wherein the base defines a plurality of openings, wherein at least two of the plurality of openings are sized and spaced apart from one another to allow a staple to be attached to the portion of skin through the at least two openings.

15. The strap tie assembly of claim 10, wherein the base defines at least one second body coupler coupled to the second base side of the base component, and the rotational element of the body is configured to removably couple to the at least one second body coupler of the base to allow the strap tie to rotate relative to the base.

16. The strap tie assembly of claim 15, wherein the first body coupler includes a first coupler edge spaced from a first cavity on an opposite side of the first cavity from the base component, and the at least one second body coupler includes a second coupler edge extending from the first coupler edge.

17. The strap tie assembly of claim 15, wherein at least two of the first body coupler and the at least one second body coupler are aligned.

18. The strap tie assembly of claim 10, wherein:
the rotational element defines a slot extending into the rotational element; and
the engagement component is configured to be at least partially received in the slot, the actuator component configured to be moved from a first position at which the engagement component extends a first distance away from the slot to a second position at which the engagement component extends a second distance less than the first distance away from the slot.

19. The strap tie assembly of claim 18, wherein the rotational element includes a circular wall defining the slot, the slot having a slot width, the engagement component including an engagement wall having an engagement width less than the slot width and a tab extending away from the slot, the tab configured to be inserted between a first cavity and a first coupler edge.

20. The strap tie assembly of claim 10, wherein the rotational element is at least one of attached to, defined within, or extended from a first body surface portion of the body.

* * * * *